United States Patent
Martin et al.

(10) Patent No.: US 8,466,143 B2
(45) Date of Patent: Jun. 18, 2013

(54) AZEPINE DERIVATIVES AS PHARMACEUTICAL AGENTS

(75) Inventors: Richard Martin, San Diego, CA (US); Tie-Lin Wang, San Diego, CA (US); Brenton T. Flatt, San Diego, CA (US); Xiao-Hui Gu, San Diego, CA (US)

(73) Assignee: Exelixis, Inc., South San Francisco, CA (US)

( * ) Notice: Subject to any disclaimer, the term of this patent is extended or adjusted under 35 U.S.C. 154(b) by 1933 days.

(21) Appl. No.: 10/565,702

(22) PCT Filed: Jul. 23, 2004

(86) PCT No.: PCT/US2004/023745
§ 371 (c)(1),
(2), (4) Date: Sep. 13, 2006

(87) PCT Pub. No.: WO2005/009387
PCT Pub. Date: Feb. 3, 2005

(65) Prior Publication Data
US 2007/0015746 A1    Jan. 18, 2007

Related U.S. Application Data

(60) Provisional application No. 60/489,854, filed on Jul. 23, 2003.

(51) Int. Cl.
*A61P 9/00*    (2006.01)
*A61K 31/55*    (2006.01)
*C07D 223/14*    (2006.01)
*C07D 223/16*    (2006.01)
*C07D 498/00*    (2006.01)
*C07D 513/00*    (2006.01)

(52) U.S. Cl.
USPC .......................................... 514/215; 540/580

(58) Field of Classification Search
USPC .......................................... 514/215; 540/580
See application file for complete search history.

(56) References Cited

U.S. PATENT DOCUMENTS

| | | | | |
|---|---|---|---|---|
| 4,362,739 A | * | 12/1982 | Kuehne | 514/410 |
| 5,461,050 A | * | 10/1995 | Janssens et al. | 514/214.02 |
| 7,485,634 B2 | * | 2/2009 | Martin et al. | 514/215 |
| 7,595,311 B2 | * | 9/2009 | Busch et al. | 514/215 |
| 2009/0203577 A1 | * | 8/2009 | Baik et al. | 514/4 |
| 2010/0173824 A1 | * | 7/2010 | Busch et al. | 514/3 |

FOREIGN PATENT DOCUMENTS

| | | |
|---|---|---|
| CH | 506 543 A | 4/1971 |
| WO | 01/05793 A | 1/2001 |
| WO | WO 03/099821 A1 | 12/2003 |

OTHER PUBLICATIONS

Kuehne et al., Biomimetic Syntheses of Indole Alkaloids. 11. Syntheses of .beta.Carboline and Indoloazepine Intermediates, The Journal of Organic Chemistry, vol. 50, No. 7, pp. 919-924, Apr. 5, 1985.*

* cited by examiner

*Primary Examiner* — Brenda Coleman
(74) *Attorney, Agent, or Firm* — McDonnell Boehnen Hulbert & Berghoff LLP

(57) ABSTRACT

Compounds, compositions and methods are provided for modulating the activity of receptors and for the treatment, prevention, or amelioration of one or more symptoms of disease or disorder related to the activity of the receptors.

43 Claims, No Drawings

AZEPINE DERIVATIVES AS PHARMACEUTICAL AGENTS

This application is a national stage entry under 35 U.S.C. §371 of PCT/US04/23745, filed Jul. 23, 2004 which claims benefit of Provisional Application No. 60/489,854, filed Jul. 23, 2003.

FIELD OF THE INVENTION

Compounds, compositions and methods are provided for modulating the activity of receptors and for the treatment, prevention, or amelioration of one or more symptoms of disease or disorder related to the activity of the receptors.

BACKGROUND OF THE INVENTION

Nuclear Receptors

Nuclear receptors are a superfamily of regulatory proteins that are structurally and functionally related and are receptors for, e.g., steroids, retinoids, vitamin D and thyroid hormones (see, e.g., Evans (1988) *Science* 240:889-895). These proteins bind to cis-acting elements in the promoters of their target genes and modulate gene expression in response to ligands for the receptors.

Nuclear receptors can be classified based on their DNA binding properties (see, e.g., Evans, supra and Glass (1994) *Endocr. Rev.* 15:391-407). For example, one class of nuclear receptors includes the glucocorticoid, estrogen, androgen, progestin and mineralocorticoid receptors which bind as homodimers to hormone response elements (HREs) organized as inverted repeats (see, e.g., Glass, supra). A second class of receptors, including those activated by retinoic acid, thyroid hormone, vitamin $D_3$, fatty acids/peroxisome proliferators (i.e., peroxisome proliferator activated zeceptor (PPAR)) and ecdysone, bind to HREs as heterodimers with a common partner, the retinoid X receptors (i.e., RXRs, also known as the 9-cis retinoic acid receptors; see, e.g., Levin et al. (1992) *Nature* 355:359-361 and Heyman et al. (1992) *Cell* 68:397-406).

RXRs are unique among the nuclear receptors in that they bind DNA as a homodimer and are required as a heterodimeric partner for a number of additional nuclear receptors to bind DNA (see, e.g., Mangelsdorf et al. (1995) *Cell* 83:841-850). The latter receptors, termed the class II nuclear receptor subfamily, include many which are established or implicated as important regulators of gene expression. There are three RXR genes (see, e.g., Mangelsdorf et al. (1992) *Genes Dev.* 6:329-344), coding for RXRα, -β, and -γ, all of which are able to heterodimerize with any of the class II receptors, although there appear to be preferences for distinct RXR subtypes by partner receptors in vivo (see, e.g., Chiba et al. (1997) *Mol. Cell. Biol.* 17:3013-3020). In the adult liver, RXRα is the most abundant of the three RXRs (see, e.g., Mangelsdorf et al. (1992) *Genes Dev.* 6:329-344), suggesting that it might have a prominent role in hepatic functions that involve regulation by class II nuclear receptors. See also, Wan et al. (2000) *Mol. Cell. Biol* 20:4436-4444.

Orphan Nuclear Receptors

Included in the nuclear receptor superfamily of regulatory proteins are nuclear receptors for whom the ligand is known and those which lack known ligands. Nuclear receptors falling in the latter category are referred to as orphan nuclear receptors. The search for activators for orphan receptors has led to the discovery of previously unknown signaling pathways (see, e.g., Levin et al., (1992), supra and Heyman et al., (1992), supra). For example, it has been reported that bile acids, which are involved in physiological processes such as cholesterol catabolism, are ligands for the farnesoid X receptor (infra).

Since it is known that products of intermediary metabolism act as transcriptional regulators in bacteria and yeast, such molecules may serve similar functions in higher organisms (see, e.g., Tomkins (1975) *Science* 189:760-763 and O'Malley (1989) *Endocrinology* 125:1119-1120). For example, one biosynthetic pathway in higher eukaryotes is the mevalonate pathway, which leads to the synthesis of cholesterol, bile acids, porphyrin, dolichol, ubiquinone, carotenoids, retinoids, vitamin D, steroid hormones and famesylated proteins.

Farnesoid X Receptor

The farnesoid X receptor (originally isolated as RIP14 (retinoid X receptor-interacting protein-1 4), see, e.g., Seol et al. (1995) *Mol. Endocrinol.* 9:72-85) is a member of the nuclear hormone receptor superfamily and is primarily expressed in the liver, kidney and intestine (see, e.g., Seol et al., supra and Forman et al. (1995) *Cell* 81:687-693). It functions as a heterodimer with the retinoid X receptor (RXR) and binds to response elements in the promoters of target genes to regulate gene transcription. The farnesoid X receptor-RXR heterodimer binds with highest affinity to an inverted repeat-1 (IR-1) response element, in which consensus receptor-binding hexamers are separated by one nucleotide. The farnesoid X receptor is part of an interrelated process, in that the receptor is activated by bile acids (the end product of cholesterol metabolism) (see, e.g., Makishima et al. (1999) *Science* 284: 1362-1365, Parks et al. (1999) *Science* 284:1365-1368, Wang et a. (1999) *Mol. Cell.* 3:543-553), which serve to inhibit cholesterol catabolism. See also, Urizar et al. (2000) *J. Biol. Chem.* 275:39313-39317.

Nuclear Receptors and Disease

Nuclear receptor activity, including the farnesoid X receptor and/or orphan nuclear receptor activity, has been implicated in a variety of diseases and disorders, including, but not limited to, hyperlipidemia and hypercholesterolemia, and complications thereof, including without limitation coronary artery disease, angina pectoris, carotid artery disease, strokes, cerebral arteriosclerosis and xanthoma, (see, e.g., International Patent Application Publication No. WO 00/57915), osteoporosis and vitamin deficiency (see, e.g., U.S. Pat. No. 6,316,5103), hyperlipoproteinemia (see, e.g., International Patent Application Publication No. WO 01/60818), hypertriglyceridemia, lipodystrophy, peripheral occlusive disease, ischemic stroke, hyperglycemia and diabetes mellitus (see, e.g., International Patent Application Publication No. WO 01/82917), disorders related to insulin resistance including the cluster of disease states, conditions or disorders that make up "Syndrome X" such as glucose intolerance, an increase in plasma triglyceride and a decrease in high-density lipoprotein cholesterol concentrations, hypertension, hyperuricemia, smaller denser low-density lipoprotein particles, and higher circulating levels of plasminogen activator inhibitor-1, atherosclerosis and gallstones (see, e.g., International Patent Application Publication No. WO 00/37077), disorders of the skin and mucous membranes (see, e.g., U.S. Pat. Nos. 6,184, 215 and 6,187,814, and International Patent Application Publication No. WO 98/32444), obesity, acne (see, e.g., International Patent Application Publication No. WO 00/49992), and cancer, cholestasis, Parkinson's disease and Alzheimer's disease (see, e.g., International Patent Application Publication No. WO 00/17334).

The activity of nuclear receptors, including the farnesoid X receptor and/or orphan nuclear receptors, has been implicated in physiological processes including, but not limited to, triglyceride metabolism, catabolism, transport or absorption, bile acid metabolism, catabolism, transport, absorption, re-absorption or bile pool composition, cholesterol metabolism, catabolism, transport, absorption, or re-absorption. The modulation of cholesterol 7α-hydroxylase gene (CYP7A1) transcription (see, e.g., Chiang et a. (2000) *J. Biol. Chem.* 275:10918-10924), HDL metabolism (see, e.g., Urizar et al. (2000) *J. Biol. Chem.* 275:39313-39317), hyperlipidemia, cholestasis, and increased cholesterol efflux and increased expression of ATP binding cassette transporter protein (ABC1) (see, e.g., International Patent Application Publication No. WO 00178972) are also modulated or otherwise affected by the farnesoid X receptor.

Thus, there is a need for compounds, compositions and methods of modulating the activity of nuclear receptors, including the farnesoid X receptor and/or orphan nuclear receptors. Such compounds are useful in the treatment, prevention, or amelioration of one or more symptoms of diseases or disorders in which nuclear receptor activity is implicated.

SUMMARY OF THE INVENTION

Compounds for use in pharmaceutical compositions and methods for modulating the activity of nuclear receptors are provided. In particular, compounds for use in compositions and methods for modulating the farnesoid X receptor, and/or orphan nuclear receptors, are provided. In one embodiment, the compounds provided herein are agonists of the farnesoid X receptor. In another embodiment, the compounds provided herein are antagonists of the farnesoid X receptor. In another embodiment, the compounds provided herein are inverse agonists, partial agonists or partial antagonists of the farnesoid X receptor. Agonists that exhibit low efficacy are, in certain embodiments, antagonists.

In one embodiment, the compounds for use in the compositions and methods provided herein have the formula (I):

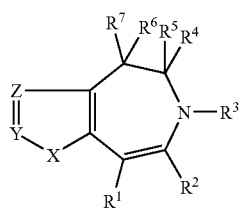

(I)

or a pharmaceutically acceptable derivative thereof, wherein:

X is $NR^9$, O or S(O)$_t$ (where t is 0 to 2);

Y is $CR^{30}$ or N;

Z is $CR^{31}$ or N;

$R^{30}$ and $R^{31}$ are each independently selected from the group consisting of halo, hydrogen, optionally substituted alkyl, optionally substituted alkenyl, optionally substituted alkynyl, optionally substituted aryl, optionally substituted heteroaryl, optionally substituted cycloalkyl, optionally substituted cycloalkylalkyl, optionally substituted heterocyclyl, optionally substituted heterocyclylalkyl, optionally substituted aralkyl, optionally substituted heteroaralkyl, —$OR^{32}$, —$SR^{32}$, —$N(R^{33})R^{34}$, —$N(R^{33})S(O)_2R^{23}$; —$N(R^{35})N(R^{33})R^{34}$, —$N(R^{35})N(R^{33})S(O)_2R^{23}$, —$C(O)R^{36}$, —$C(O)OR^{32}$, —$C(S)OR^{32}$, —$C(O)SR^{32}$, —$C(O)N(R^{33})R^{34}$, —$C(S)N(R^{33})R^{34}$, —$C(O)N(R^{33})S(O)_2R^{23}$, —$C(S)N(R^{33})S(O)_2R^{23}$, —$C(O)N(R^{35})N(R^{33})R^{34}$, —$C(S)N(R^{35})N(R^{33})R^{34}$ and —$C(O)N(R^{35})N(R^{33})S(O)_2R^{23}$; or $R^{30}$ and $R^{31}$ together with the carbon atoms to which they are attached, form an optionally substituted cycloalkyl ring, optionally substituted cycloalkenyl ring, optionally substituted cycloalkynyl ring, optionally substituted heterocyclyl ring, optionally substituted heteroaryl ring or optionally substituted aryl ring with the exception of substituted or unsubstituted phenyl or substituted or unsubstituted naphthyl;

$R^{32}$, $R^{33}$, $R^{34}$, $R^{35}$ and $R^{36}$ are selected as in (a) or (b) as follows: (a) $R^{32}$, $R^{33}$, $R^{34}$, $R^{35}$ and $R^{36}$ are each independently hydrogen, optionally substituted alkyl, optionally substituted alkenyl, optionally substituted alkynyl, optionally substituted cycloalkyl, optionally substituted aryl, optionally substituted aralkyl, optionally substituted heterocyclyl, optionally substituted heteroaryl, or optionally substituted heteroaralkyl; or (b) $R^{33}$ and $R^{34}$, together with the nitrogen atom to which they are attached, form an optionally substituted heterocyclyl ring, or an optionally substituted heteroaryl ring, and the others of $R^{32}$, $R^{33}$, $R^{34}$, $R^{35}$ and $R^{36}$ are selected as in (a) above, $R^1$ and $R^2$ are each independently selected from a group consisting of halo, hydrogen, optionally substituted alkyl, optionally substituted alkenyl, optionally substituted alkynyl, optionally substituted aryl, optionally substituted heteroaryl, optionally substituted cycloalkyl, optionally substituted heterocyclyl, optionally substituted aralkyl, optionally substituted heteroaralkyl, —$OR^4$, —$SR^4$, —$N(R^{15})R^{16}$, —$N(R^{15})S(O)_2R^{23}$; —$N(R^{17})N(R^{15})R^{16}$, —$N(R^{17})N(R^{15})S(O)_2R^{23}$, —$C(O)R^{18}$, —$C(O)OR^{14}$, —$C(S)OR^{14}$, —$C(O)SR^{14}$, —$C(O)N(R^{15})R^{16}$, —$C(O)N(R^{15})S(O)_2R^{23}$, —$C(O)N(R^{15})N=R^{16}$, —$C(O)N(R^{17})N(R^{15})R^{16}$ and —$C(O)N(R^{17})N(R^{15})S(O)_2R^{23}$;

$R^3$ is hydrogen, optionally substituted alkyl, optionally substituted alkenyl, optionally substituted alkynyl, optionally substituted cycloalkyl, optionally substituted aryl, optionally substituted aralkyl, optionally substituted heteroaryl, optionally substituted heterocyclyl, optionally substituted heteroaralkyl, —$C(O)R^{10}$, —$C(O)OR^{10}$, —$S(O)_2R^{10}$, —$C(O)N(R^{11})R^{12}$, —$C(O)N(R^{11})S(O)_2R^{23}$, —$C(O)N(R^{13})N(R^{11})R^{12}$, —$C(O)N(R^{13})N(R^{11})S(O)_2R^{23}$, —$N(R^{13})C(O)R^{10}$, —$N(R^{13})C(O)N(R^{11})R^{12}$, —$N(R^{13})C(O)N(R^{11})S(O)_2R^{23}$, —$N(R^{10})C(O)N(R^{13})N(R^{11})R^{12}$, —$N(R^{10})C(O)N(R^{13})N(R^{11})S(O)_2R^{23}$, —$N(R^{13})C(O)OR^{10}$, —$P(O)OR^{10}$ or —$P(O)(OR^{19})OR^{12}$;

$R^4$, $R^5$, $R^6$ and $R^7$ are each independently selected from a group consisting of hydrogen, halo, optionally substituted alkyl, optionally substituted alkenyl, optionally substituted alkynyl, optionally substituted aryl, optionally substituted heteroaryl, optionally substituted cycloalkyl, optionally substituted heterocyclyl, optionally substituted aralkyl, optionally substituted heteroaralkyl, —$OR^{14}$, —$SR^{14}$, —$S(O)_2R^{14}$, —$N(R^{15})R^{16}$, —$N(R^{15})S(O)_2R^{23}$, —$C(O)R^{18}$, —$C(O)OR^{20}$, —$C(O)N(R^{21})R^{22}$, —$C(O)N(R^{21})S(O)_2R^{23}$; —$C(O)N(R^{24})N(R^{21})R^{22}$ and —$C(O)N(R^{24})N(R^{21})S(O)_2R^{23}$; or $R^4$ and $R^5$ or $R^6$ and $R^7$, together with the carbon atom to which they are attached, form an optionally substituted cycloalkyl ring, optionally substituted heterocyclyl ring, an optionally substituted cycloalkenyl ring or together form a double bond, and the others of $R^4$, $R^5$, $R^6$ and $R^7$ are as described above; or $R^6$ and $R^7$ together form an oxo, thioxo, optionally substituted imino, optionally substituted oxime or an optionally substituted hydrazone, or $R^6$ and $R^7$, together with the carbon atom to which they are attached, form an optionally substituted exocyclic double bond, and $R^4$ and $R^5$ are as described above;

$R^9$ is hydrogen, optionally substituted alkyl, —$C(O)R^{18}$, —$C(O)OR^{20}$ or —$S(O)_2R^{23}$;

$R^{10}$, $R^{11}$, $R^{12}$, $R^{13}$ and $R^{19}$ are selected as in (a) or (b) as follows: (a) $R^{10}$, $R^{11}$, $R^{12}$, $R^{13}$ and $R^{19}$ each independently hydrogen, optionally substituted alkyl, optionally substituted alkenyl, optionally substituted alkynyl, optionally substituted cycloalkyl, optionally substituted aryl, optionally substituted aralkyl, optionally substituted heterocyclyl, optionally substituted heteroaryl, or optionally substituted heteroaralkyl; or (b) $R^{11}$ and $R^{12}$ or $R^{12}$ and $R^{19}$, together with the atoms to which they are attached, form an optionally substituted heterocyclyl ring or an optionally substituted heteroaryl ring; and the others of $R^{10}$, $R^{11}$, $R^{12}$, $R^{13}$ and $R^{19}$ are selected as in (a), above;

$R^{14}$, $R^{15}$, $R^{16}$, $R^{17}$ and $R^{18}$ are selected as in (a) or (b) as follows: (a) $R^{14}$, $R^{15}$, $R^{16}$, $R^{17}$ and $R^{18}$ are each independently hydrogen, optionally substituted alkyl, optionally substituted alkenyl, optionally substituted alkynyl, optionally substituted cycloalkyl, optionally substituted aryl, optionally substituted aralkyl, optionally substituted heterocyclyl, optionally substituted heteroaryl, or optionally substituted heteroaralkyl; or (b) $R^{15}$ and $R^{16}$, together with the nitrogen atom to which they are attached, form an optionally substituted heterocyclyl ring, or an optionally substituted heteroaryl ring, and the others of $R^{14}$, $R^{15}$, $R^{16}$, $R^{17}$ and $R^{18}$ are selected as in (a) above;

$R^{20}$, $R^{21}$, $R^{22}$ and $R^{24}$ are selected as in (a) or (b) as follows: (a) $R^{20}$, $R^{21}$, $R^{22}$ and $R^{24}$ are each independently hydrogen, optionally substituted alkyl, optionally substituted alkenyl, optionally substituted alkynyl, optionally substituted cycloalkyl, optionally substituted aryl, optionally substituted aralkyl, optionally substituted heterocyclyl, optionally substituted heteroaryl, or optionally substituted heteroaralkyl; or (b) $R^{21}$ and $R^{22}$, together with the nitrogen atom to which they are attached, form an optionally substituted heterocyclyl ring, or an optionally substituted heteroaryl ring, and the others of $R^{20}$, $R^{21}$, $R^{22}$ and $R^{24}$ are selected as in (a) above;

$R^{23}$ is optionally substituted alkyl, optionally substituted alkenyl, optionally substituted alkynyl, optionally substituted cycloalkyl, optionally substituted aryl, optionally substituted aralkyl, optionally substituted heterocyclyl, optionally substituted heteroaryl, or optionally substituted heteroaralkyl;

each of $R^1$-$R^{24}$ and $R^{31}$-$R^{36}$, when substituted, are substituted with one or more substituents, each independently selected from $Q^1$;

each $Q^1$ is independently selected from halo, pseudohalo, oxo, thioxo, cyano, thiocyano, isocyano, nitro, azido, alkyl, haloalkyl, alkenyl containing 1 to 2 double bonds, alkynyl containing 1 to 2 triple bonds, cycloalkyl, cycloalkenyl, cycloalkynyl, cycloalkylalkyl, heterocyclyl, heterocyclylalkyl, aryl, heteroaryl, aralkyl, aralkenyl, aralkynyl, heteroarylalkyl, alkylidene, arylalkylidene, aryloxyarylcarbonylamino, hydroxycarbonylalkylthio, halosulfonyl, —$OR^{70}$, —$SR^{70}$, —$R^{60}$—C(J )$R^{71}$, —$R^{60}$—N($R^{70}$)C(J)$R^{71}$, —OC(O)$R^{71}$, —$R^{60}$—N($R^{75}$)($R^{76}$), —$N^{+(R^{77})}{}_3$, —P($R^{78}$)$_2$, —P(O)($R^{78}$)$_2$, —OP(O)($R^{78}$)$_2$, —N($R^{70}$)S(O)$_2R^{71}$, —S(O)$_2R^{71}$,—S(O)$R^{82}$,—OS(O)$R^{83}$,—OS(O)$_2R^{83}$ or —Si($R^{83}$)$_3$;

two $Q^1$ groups, which substitute atoms in a 1,2 or 1,3 arrangement, together with the carbon atoms to which they are attached form a cycloalkyl ring, cycloalkenyl ring, cycloalkynyl ring or heterocyclyl ring; or each $Q^1$ is independently substituted or unsubstituted with one or more substituents each independently selected from $Q^2$;

each $Q^2$ is independently selected from halo, pseudohalo, oxo, thioxo, cyano, thiocyano, isocyano, nitro, azido, alkyl, haloalkyl, alkenyl containing 1 to 2 double bonds, alkynyl containing 1 to 2 triple bonds, cycloalkyl, cycloalkenyl, cycloalkynyl, cycloalkylalkyl, heterocyclyl, heterocyclylalkyl, aryl, heteroaryl, aralkyl, aralkenyl, aralkynyl, heteroarylalkyl, alkylidene, arylalkylidene, aryloxyarylcarbonylamino, hydroxycarbonylalkylthio, halosulfonyl, —$OR^{70}$, —$SR^{70}$, —$R^{60}$—C(J )$R^{71}$, —$R^{60}$—N($R^{70}$)C(J)$R^{71}$, —OC(O)$R^{71}$, —$R^{60}$—N($R^{75}$)($R^{76}$), —$N^{+(R^{77})}{}_3$, —P($R^{78}$)$_2$, —P(O)($R^{78}$)$_2$, —OP(O)($R^{78}$)$_2$, —N($R^{70}$)S(O)$_2R^{71}$, —S(O)$_2R^{71}$,—S(O)$R^{82}$,—OS(O)$R^{83}$,—OS(O)$_2R^{83}$ or —Si($R^{83}$)$_3$;

two $Q^2$ groups, which substitute atoms in a 1,2 or 1,3 arrangement, together with the carbon atoms to which they are attached form a cycloalkyl ring, cycloalkenyl ring, cycloalkynyl ring or heterocyclyl ring;

each J is independently O, S or —$NR^{70}$;

each $R^{60}$ is independently a direct bond or alkylene;

each $R^{70}$ is independently hydrogen, alkyl, alkenyl, alkynyl, cycloalkyl, heterocyclyl, aryl, heteroaryl, aralkyl, haloalkyl, heterocyclylalkyl or heteroaralkyl;

each $R^{71}$ is independently hydrogen, alkyl, alkenyl, alkynyl, cycloalkyl, heterocyclyl, aryl, heteroaryl, aralkyl, haloalkyl, heterocyclylalkyl, heteroaralkyl, —$OR^{72}$ or —N($R^{73}$)$R^{74}$;

$R^{72}$, $R^{73}$ and $R^{74}$ are each independently hydrogen, alkyl, alkenyl, alkynyl, cycloalkyl, heterocyclyl, aryl, heteroaryl, aralkyl or heteroaralkyl; or $R^{73}$ and $R^{74}$, together with the nitrogen atom to which they are attached, form a heterocyclyl ring or heteroaryl ring;

$R^{75}$ and $R^{76}$ are each independently hydrogen, alkyl, alkenyl, alkynyl, aryl, aralkyl, heteroaryl, heteroaralkyl, heterocyclyl or heterocyclylalkyl; or $R^{75}$ and $R^{76}$, together with the nitrogen atom to which they are attached, form a heterocyclyl ring or heteroaryl ring;

each $R^{77}$ is independently alkyl, alkenyl, cycloalkyl, heterocyclyl, aryl, heteroaryl, aralkyl or heteroaralkyl;

$R^{78}$ is alkyl, heteroaryl, heterocyclyl, aryl, —$OR^{79}$ or —N($R^{80}$)$R^{81}$;

$R^{79}$ is hydrogen, alkyl, alkenyl, cycloalkyl, heterocyclyl, aryl, heteroaryl, aralkyl or heteroaralkyl;

$R^{80}$ and $R^{81}$ are each independently hydrogen, alkyl, alkenyl, alkynyl, cycloalkyl, heterocyclyl, aryl, heteroaryl, aralkyl or heteroaralkyl; or $R^{80}$ and $R^{81}$, together with the nitrogen atom to which they are attached, form a heterocyclyl ring or heteroaryl ring;

$R^{82}$ is alkyl, alkenyl, cycloalkyl, heterocyclyl, aryl, heteroaryl, aralkyl, heteroaralkyl or —$OR^{83}$; and each $R^{83}$ is independently alkyl, alkenyl, cycloalkyl, heterocyclyl, aryl, heteroaryl, aralkyl or heteroaralkyl.

Also provided are methods for treatment, prevention, or amelioration of one or more symptoms of diseases or disorders mediated by, or in which nuclear receptor activity, including the farnesoid X receptor and/or orphan nuclear receptor activity, is implicated, comprising administering a claimed compound or composition to a subject in need thereof. Such methods include methods of treatment, prevention and amelioration of one or more symptoms of hypercholesterolemia, hyperlipoproteinemia, hypertriglyceridemia, lipodystrophy, hyperglycemia, diabetes mellitus, dyslipidemia, atherosclerosis, gallstone disease, acne vulgaris, acneiform skin conditions, diabetes, Parkinson's disease, cancer, Alzheimer's disease, inflammation, immunological disorders, lipid disorders, obesity, conditions characterized by a perturbed epidermal barrier function, hyperlipidemia, cholestasis, peripheral occlusive disease, ischemic stroke, conditions of disturbed differentiation or excess proliferation of the epidermis or mucous membrane, or cardiovascular disorders, using one or more of the compounds provided herein, or pharmaceutically acceptable derivatives thereof.

Methods of modulating the activity of nuclear receptors, including the farnesoid X receptor and/or orphan nuclear receptors, using the compounds and compositions provided herein are also provided. The compounds and compositions provided herein are active in assays that measure the activity of nuclear receptors, including the farnesoid X receptor and/or orphan nuclear receptors, including the assays provided herein. These methods include inhibiting and up-regulating the activity of nuclear receptors, including the farnesoid X receptor and/or orphan nuclear receptors.

Also contemplated herein is combination therapy using more or more compounds or compositions provided herein, or a pharmaceutically acceptable derivative thereof, in combination with one or more of the following: antihyperlipidemic agents, plasma HDL-raising agents, antihypercholesterolemic agents, cholesterol biosynthesis inhibitors (such as HMG CoA reductase inhibitors, such as lovastatin, simvastatin, pravastatin, fluvastatin, atorvastatin and rivastatin), acyl-coenzyme A: cholesterol acytransferase (ACAT) inhibitors, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, anti-oxidant vitamins, β-blockers, anti-diabetes agents, angiotensin II antagonists, angiotensin converting enzyme inhibitors, platelet aggregation inhibitors, fibrinogen receptor antagonists, LXR α or β agonists, antagonists or partial agonists, aspirin or fibric acid derivatives. The compound or composition provided herein, or pharmaceutically acceptable derivative thereof, is administered simultaneously with, prior to, or after administration of one or more of the above agents. Pharmaceutical compositions containing a compound provided herein and one or more of the above agents are also provided.

In practicing the methods, effective amounts of the compounds or compositions containing therapeutically effective concentrations of the compounds, which are formulated for systemic delivery, including parenteral, oral, or intravenous delivery, or for local or topical application for the treatment of nuclear receptor, including the farnesoid X receptor and/or orphan nuclear receptor, mediated diseases or disorders, or diseases or disorders in which nuclear receptor activity, including the farnesoid X receptor and/or orphan nuclear receptor activity, is implicated, including, but not limited to, hypercholesterolemia, hyperlipoproteinemia, hypertriglyceridemia, lipodystrophy, hyperglycemia, diabetes mellitus, dyslipidemia, atherosclerosis, gallstone disease, acne vulgaris, acneiform skin conditions, diabetes, Parkinson's disease, cancer, Alzheimer's disease, inflammation, immunological disorders, lipid disorders, obesity, conditions characterized by a perturbed epidermal barrier function, hyperlipidemia, cholestasis, peripheral occlusive disease, ischemic stroke, conditions of disturbed differentiation or excess proliferation of the epidermis or mucous membrane, or cardiovascular disorders, are administered to an individual exhibiting the symptoms of these diseases or disorders. The amounts are effective to ameliorate or eliminate one or more symptoms of the diseases or disorders.

Articles of manufacture containing packaging material, a compound or composition, or pharmaceutically acceptable derivative thereof, provided herein, which is effective for modulating the activity of nuclear receptors, including the farnesoid X receptor and/or orphan nuclear receptors, or for treatment, prevention or amelioration of one or more symptoms of nuclear receptor, including the farnesoid X receptor and/or orphan nuclear receptor mediated diseases or disorders, or diseases or disorders in which nuclear receptor activity, including the farnesoid X receptor and/or orphan nuclear receptor activity, is implicated, within the packaging material, and a label that indicates that the compound or composition, or pharmaceutically acceptable derivative thereof, is used for modulating the activity of nuclear receptors, including the farnesoid X receptor and/or orphan nuclear receptors, or for treatment, prevention or amelioration of one or more symptoms of nuclear receptor, including the farnesoid X receptor and/or orphan nuclear receptor, mediated diseases or disorders, or diseases or disorders in which nuclear receptor activity, including the farnesoid X receptor and/or orphan nuclear receptor activity, is implicated, are provided.

DETAILED DESCRIPTION OF THE INVENTION

A. Definitions

Unless defined otherwise, all technical and scientific terms used herein have the same meaning as is commonly understood by one of ordinary skill in the art to which this invention belongs. All patents, applications, published applications and other publications are incorporated by reference in their entirety. In the event that there are a plurality of definitions for a term herein, those in this section prevail unless stated otherwise.

As used herein, a nuclear receptor is a member of a superfamily of regulatory proteins that are receptors for, e.g., steroids, retinoids, vitamin D and thyroid hormones. These proteins bind to cis-acting elements in the promoters of their target genes and modulate gene expression in response to a ligand therefor. Nuclear receptors may be classified based on their DNA binding properties. For example, the glucocorticoid, estrogen, androgen, progestin and mineralocorticoid receptors bind as homodimers to hormone response elements (HREs) organized as inverted repeats. Another example are receptors, including those activated by retinoic acid, thyroid hormone, vitamin $D_3$, fatty acids/peroxisome proliferators and ecdysone, that bind to HREs as heterodimers with a common partner, the retinoid X receptor (RXR). Among the latter receptors is the farnesoid X receptor.

As used herein, an orphan nuclear receptor is a gene product that embodies the structural features of a nuclear receptor that was identified without any prior knowledge of their association with a putative ligand and/or for which the natural ligand is unknown. Under this definition, orphan nuclear receptors include, without limitation, farnesoid X receptors, liver X receptors (LXR α & β), retinoid X receptors (RXRα, β & γ), and peroxisome proliferator activator receptors (PPAR α, β, & γ) (see, Giguere, *Endocrine Reviews* (1999), Vol. 20, No. 5: pp. 689-725).

As used herein, farnesoid X receptor refers to all mammalian forms of such receptor including, for example, alternative splice isoforms and naturally occurring isoforms (see, e.g. Huber et al, *Gene* (2002), Vol. 290, pp.:35-43). Representative farnesoid X receptor species include, without limitation the rat (GenBank Accession No. NM_021745), mouse (Genbank Accession No. NM_009108), and human (GenBank Accession No. NM_005123) forms of the receptor.

As used herein, pharmaceutically acceptable derivatives of a compound include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, aryl, heteroaryl, aralkyl, heteroaralkyl, cycloalkyl or heterocyclyl. Pharmaceutically acceptable enol esters include, but are not limited to, derivatives of formula C=C(OC(O)R) where R is hydrogen, alkyl, alkenyl, alkynyl, aryl, heteroaryl, aralkyl, heteroaralkyl, cycloalkyl or heterocyclyl. Pharmaceutically acceptable solvates and hydrates are complexes of a compound with one or more solvent or water molecules, or 1 to about 100, or 1 to about 10, or one to about 2, 3 or 4, solvent or water molecules.

As used herein, treatment means any manner in which one or more of the symptoms of a disease or disorder are ameliorated or otherwise beneficially altered. Treatment also encompasses any pharmaceutical use of the compositions herein, such as use for treating a nuclear receptor mediated diseases or disorders, or diseases or disorders in which nuclear receptor activity, including the farnesoid X receptor or orphan nuclear receptor activity, is implicated.

As used herein, amelioration of the symptoms of a particular disorder by administration of a particular compound or pharmaceutical composition refers to any lessening, whether permanent or temporary, lasting or transient that can be attributed to or associated with administration of the composition.

As used herein, $IC_{50}$ refers to an amount, concentration or dosage of a particular test compound that achieves a 50% inhibition of a maximal response, such as modulation of nuclear receptor, including the farnesoid X receptor, activity, in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

As used herein, a prodrug is a compound that, upon in vivo administration, is metabolized by one or more steps or processes or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach,* Oxford University Press, New York, pages 388-392).

When the compounds described herein contain olefinic double bonds or other centers of geometric asymmetry, and unless specified otherwise, it is intended that the compounds include both E and Z geometric isomers. Likewise, all tautomeric forms are also intended to be included.

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. In the case of amino acid residues, such residues may be of either the L- or D-form. The configuration for naturally occurring amino acid residues is generally L. When not specified the residue is the L form. As used herein, the term "amino acid" refers to α-amino acids which are racemic, or of either the D- or L-configuration. The designation "d" preceding an amino acid designation (e.g., dAla, dSer, dVal, etc.) refers to the D-isomer of the amino acid. The designation "dl" preceding an amino acid designation (e.g., dlpip) refers to a mixture of the L- and D-isomers of the amino acid. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

Optically active (+) and (−), (R)- and (S)-, or (Dy and (L)-isomers may be prepared using chiral synthons or chiral reagents, or resolved using conventional techniques, such as reverse phase HPLC.

As used herein, substantially pure means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein, alkyl, alkenyl and alkynyl carbon chains, if not specified, contain from 1 to 20 carbons, or 1 or 2 to 16 carbons, and are straight or branched. Alkenyl carbon chains of from 2 to 20 carbons, in certain embodiments, contain 1 to 8 double bonds and alkenyl carbon chains of 2 to 16 carbons, in certain embodiments, contain 1 to 5 double bonds. Alkynyl carbon chains of from 2 to 20 carbons, in certain embodiments, contain 1 to 8 triple bonds, and the alkynyl carbon chains of 2 to 16 carbons, in certain embodiments, contain 1 to 5 triple bonds. Exemplary alkyl, alkenyl and alkynyl groups herein include, but are not limited to, methyl, ethyl, propyl, isopropyl, isobutyl, n-butyl, sec-butyl, tert-butyl, isopentyl, neopentyl, tert-pentyl, isohexyl, allyl (propenyl) and propargyl (propynyl). As used herein, lower alkyl, lower alkenyl, and lower alkynyl refer to carbon chains having from about 1 or about 2 carbons up to about 6 carbons. As used herein, "alk(en)(yn)yl" refers to an alkyl group containing at least one double bond and at least one triple bond.

As used herein, "cycloalkyl" refers to a saturated mono- or multi-cyclic ring system, in certain embodiments of 3 to 10 carbon atoms, in other embodiments of 3 to 6 carbon atoms; cycloalkenyl and cycloalkynyl refer to mono- or multicyclic ring systems that respectively include at least one double bond and at least one triple bond. Cycloalkenyl and cycloalkynyl groups may, in certain embodiments, contain 3 to 10 carbon atoms, with cycloalkenyl groups, in further embodiments, containing 4 to 7 carbon atoms and cycloalkynyl groups, in further embodiments, containing 8 to 10 carbon atoms. The ring systems of the cycloalkyl, cycloalkenyl and cycloalkynyl groups may be composed of one ring or two or more rings which may be joined together in a fused, bridged or spiro-connected fashion. "Cycloalk(en)(yn)yl" refers to a cycloalkyl group containing at least one double bond and at least one triple bond.

As used herein, "aryl" refers to aromatic monocyclic or multicyclic groups containing from 6 to 19 carbon atoms. Aryl groups include, but are not limited to groups such as unsubstituted or substituted fluorenyl, unsubstituted or substituted phenyl, and unsubstituted or substituted naphthyl.

As used herein, "heteroaryl" refers to a monocyclic or multicyclic aromatic ring system, in certain embodiments, of about 5 to about 15 members where one or more, in one embodiment 1 to 3, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrimidinyl, tetrazolyl, thienyl, pyridyl, pyrrolyl, thiazolyl, isothiazolyl, oxazolyl, isoxazolyl, triazolyl, quinolinyl and isoquinolinyl.

As used herein, a "heteroarylium" group is a heteroaryl group that is positively charged on one or more of the heteroatoms.

As used herein, "heterocyclyl" refers to a stable 3- to 18-membered ring radical which consists of carbon atoms and from one to five heteroatoms selected from the group consisting of nitrogen, oxygen and sulfur. For purposes of this invention, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be aromatic or partially or fully saturated. Examples of such heterocyclyl radicals include, but are not limited to, azepinyl, acridinyl, benzimidazolyl, benzthiazolyl, benzindolyl, benzothiadiazolyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl; carbazolyl, cinnolinyl, dioxolanyl, dibenzofuranyl, decahydroisoquinolyl, furanyl, furanonyl, isothiazolyl, imidazolyl, imidazolinyl, imidazolidinyl, isothiazolidinyl, indolyl, indazolyl, isoindolyl, indolinyl, isoindolinyl, indolizinyl, isoxazolyl, isoxazolidinyl, morpholinyl, naphthyridinyl, oxadiazolyl, octahydroindolyl, octahydroisoindolyl, 2-oxopiperazinyl, 2-oxopiperidinyl, 2-oxopyrrolidinyl, 2-oxoazepinyl, oxazolyl, oxazolidinyl, oxiranyl, piperidinyl, piperazinyl, 4-piperidonyl, phenazinyl, phenothiazinyl, phenoxazinyl, phthalazinyl, pteridinyl, purinyl, pyrrolyl, pyrrolidinyl, pyrazolyl, pyrazolidinyl, pyridinyl, pyrazinyl, pyrimidinyl, pyridazinyl, quinazolinyl, quinoxalinyl, quinolinyl, quinuclidinyl, isoquinolinyl, thiazolyl, thiazolidinyl, thiadiazolyl, triazolyl, tetrazolyl, tetrahydrofuryl, triazinyl, tetrahydropyranyl, thiophenyl, thiamorpholinyl, thiamorpholinyl sulfoxide, and thiamorpholinyl sulfone.

As used herein, "oxacyclohexyl" refers to a cyclohexyl ring wherein one carbon in the ring is replaced by an oxygen, e.g. tetrahydropyranyl.

As used herein, "dioxacyclohexyl" refers to a cyclohexyl ring wherein two carbons in the ring are replaced by two oxygen atoms, one example of which is teterahydrodioxanyl.

As used herein, "azacyclohexyl" refers to a cyclohexyl ring wherein one carbon in the ring is replaced by a nitrogen, e.g. tetrahydropiperidinyl.

As used herein, "diazacyclohexyl" refers to a cyclohexyl ring wherein two carbons in the ring are replaced by two nitrogen atoms, one example of which is piperazinyl.

As used herein, "oxa-azacyclohexyl" refers to a cyclohexyl ring wherein two carbons in the ring are replaced by a nitrogen atom and an oxygen atom, two such examples being morpholinyl or oxazinyl.

As used herein, "thia-azacyclohexyl" refers to a cyclohexyl ring wherein two carbons in the ring are replaced by a nitrogen atom and an oxygen atom, one such example being thiazinyl.

As used herein, "thiacyclohexyl" refers to a cyclohexyl ring wherein one carbon in the ring is replaced by one sulfur atom, one example of which is tetrahydrothiopyranyl.

As used herein, "dithiacyclohexyl" refers to a cyclohexyl ring wherein two carbons in the ring are replaced by two sulfur atoms.

As used herein, "aralkyl" refers to an alkyl group in which one of the hydrogen atoms of the alkyl is replaced by an aryl group.

As used herein, "heteroaralkyl" refers to an alkyl group in which one of the hydrogen atoms of the alkyl is replaced by a heteroaryl group.

As used herein, "halo", "halogen" or "halide" refers to F, Cl, Br or I.

As used herein, pseudohalides or pseudohalo groups are groups that behave substantially similar to halides. Such compounds can be used in the same manner and treated in the same manner as halides. Pseudohalides include, but are not limited to, cyanide, cyanate, thiocyanate, selenocyanate, trifluoromethoxy, and azide.

As used herein, "haloalkyl" refers to an alkyl group in which one or more of the hydrogen atoms are replaced by halogen. Such groups include, but are not limited to, chloromethyl, trifluoromethyl and 1-chloro-2-fluoroethyl.

As used herein, "haloalkoxy" refers to RO— in which R is a haloalkyl group.

As used herein, "sulfinyl" or "thionyl" refers to —S(O)—. As used herein, "sulfonyl" or "sulfuryl" refers to —S(O)$_2$—. As used herein, "sulfo" refers to —S(O)$_2$O—. As used herein, "halosulfonyl" refers to —S(O)$_2$—R in which R is a halo group, preferably fluoro.

As used herein, "carboxy" refers to a divalent radical, —C(O)O—.

As used herein, "carbamoyl" or "aminocarbonyl" refers to —C(O)NH$_2$.

As used herein, "alkylaminocarbonyl" refers to —C(O)NHR in which R is alkyl, including lower alkyl. As used herein, "dialkylaminocarbonyl" refers to —C(O)NR'R in which R' and R are independently alkyl, including lower alkyl; "carboxamide" refers to groups of formula —NR'COR in which R' and R are independently alkyl, including lower alkyl.

As used herein, "diarylaminocarbonyl" refers to —C(O)NRR' in which R and R' are independently selected from aryl, including lower aryl, such as phenyl.

As used herein, "arylalkylaminocarbonyl" refers to —C(O)NRR' in which one of R and R' is aryl, including lower aryl, such as phenyl, and the other of R and R' is alkyl, including lower alkyl.

As used herein, "arylaminocarbonyl" refers to —C(O)NHR in which R is aryl, including lower aryl, such as phenyl.

As used herein, "hydroxycarbonyl" refers to —COOH.

As used herein, "alkoxycarbonyl" refers to —C(O)OR in which R is alkyl, including lower alkyl.

As used herein, "aryloxycarbonyl" refers to —C(O)OR in which R is aryl, including lower aryl, such as phenyl.

As used herein, "alkoxy" and "alkylthio" refer to RO— and RS—, in which R is alkyl, including lower alkyl.

As used herein, "aryloxy" and "arylthio" refer to RO— and RS—, in which R is aryl, including lower aryl, such as phenyl.

As used herein, "alkylene" refers to a straight, branched or cyclic, in certain embodiments straight or branched, divalent aliphatic hydrocarbon group, in one embodiment having from 1 to about 20 carbon atoms, in another embodiment having from 1 to 12 carbons. In a further embodiment alkylene includes lower alkylene. There may be optionally inserted along the alkylene group one or more oxygen, sulfur, including $S(O)$ and $S(O)_2$ groups, or optionally substituted nitrogen atoms, including —NR— and —N$^+$RR— groups, where the nitrogen substituent(s) is(are) alkyl, aryl, aralkyl, heteroaryl, heteroaralkyl or COR', where R' is alkyl, aryl, aralkyl, heteroaryl, heteroaralkyl, —OY or —NYY, where Y is hydrogen, alkyl, aryl, heteroaryl, cycloalkyl or heterocyclyl. Alkylene groups include, but are not limited to, methylene (—CH$_2$—), ethylene (—CH$_2$CH$_2$—), propylene (—(CH$_2$)$_3$—), methylenedioxy (—O—CH$_2$—O—) and ethylenedioxy (—O—CH$_2$)$_2$—O—). The term "lower alkylene" refers to alkylene groups having 1 to 6 carbons. In certain embodiments, alkylene groups are lower alkylene, including alkylene of 1 to 3 carbon atoms.

As used herein, "azaalkylene" refers to —(CRR)$_n$—NR—(CRR)$_m$—, where n and m are each independently an integer from 0 to 4. As used herein, "oxaalkylene" refers to —(CRR)$_n$—O—(CRR)$_m$—, where n and m are each independently an integer from 0 to 4. As used herein, "thiaalkylene" refers to —(CRR)$_n$—S—(CRR)$_m$—, —(CRR)$_n$—S(O)—(CRR)$_m$—, and —(CRR)$_n$—S(O)$_2$—(CRR)$_m$—, where n and m are each independently an integer from 0 to 4.

As used herein, "alkenylene" refers to a straight, branched or cyclic, in one embodiment straight or branched, divalent aliphatic hydrocarbon group, in certain embodiments having from 2 to about 20 carbon atoms and at least one double bond, in other embodiments 1 to 12 carbons. In further embodiments, alkenylene groups include lower alkenylene. There may be optionally inserted along the alkenylene group one or more oxygen, sulfur or optionally substituted nitrogen atoms, where the nitrogen substituent is alkyl. Alkenylene groups include, but are not limited to, —H=CH—CH=CH— and —CH=CH—CH$_2$—. The term "lower alkenylene" refers to alkenylene groups having 2 to 6 carbons. In certain embodiments, alkenylene groups are lower alkenylene, including alkenylene of 3 to 4 carbon atoms.

As used herein, "alkynylene" refers to a straight, branched or cyclic, in certain embodiments straight or branched, divalent aliphatic hydrocarbon group, in one embodiment having from 2 to about 20 carbon atoms and at least one triple bond, in another embodiment 1 to 12 carbons. In a further embodiment, alkynylene includes lower alkynylene. There may be optionally inserted along the alkynylene group one or more oxygen, sulfur or optionally substituted nitrogen atoms, where the nitrogen substituent is alkyl. Alkynylene groups include, but are not limited to, —C≡C—C≡C—, —C≡C— and —C≡C—CH$_2$—. The term "lower alkynylene" refers to alkynylene groups having 2 to 6 carbons. In certain embodiments, alkynylene groups are lower alkynylene, including alkynylene of 3 to 4 carbon atoms.

As used herein, "alk(en)(yn)ylene" refers to a straight, branched or cyclic, in certain embodiments straight or branched, divalent aliphatic hydrocarbon group, in one embodiment having from 2 to about 20 carbon atoms and at least one triple bond, and at least one double bond; in another embodiment 1 to 12 carbons. In further embodiments, alk(en)(yn)ylene includes lower alk(en)(yn)ylene. There may be optionally inserted along the alkynylene group one or more oxygen, sulfur oroptionally substituted nitrogen atoms, where the nitrogen substituent is alkyl. Alk(en)(yn)ylene groups include, but are not limited to, —C=C—(CH$_2$)$_m$—C≡C—, where n is 1 or 2. The term "lower alk(en)(yn)ylene" refers to alk(en)(yn)ylene groups having up to 6 carbons. In certain embodiments, alk(en)(yn)ylene groups have about 4 carbon atoms.

As used herein, "cycloalkylene" refers to a divalent saturated mono- or multicyclic ring system, in certain embodiments of 3 to 10 carbon atoms, in other embodiments 3 to 6 carbon atoms; cycloalkenylene and cycloalkynylene refer to divalent mono- or multicyclic ring systems that respectively include at least one double bond and at least one triple bond. Cycloalkenylene and cycloalkynylene groups may, in certain embodiments, contain 3 to 10 carbon atoms, with cycloalkenylene groups in certain embodiments containing 4 to 7 carbon atoms and cycloalkynylene groups in certain embodiments containing 8 to 10 carbon atoms. The ring systems of the cycloalkylene, cycloalkenylene and cycloalkynylene groups may be composed of one ring or two or more rings which may be joined together in a fused, bridged or spiro-connected fashion. "Cycloalk(en)(yn)ylene" refers to a cycloalkylene group containing at least one double bond and at least one triple bond.

As used herein, "arylene" refers to a monocyclic or polycyclic, in certain embodiments monocyclic, divalent aromatic group, in one embodiment having from 5 to about 20 carbon atoms and at least one aromatic ring, in another embodiment 5 to 12 carbons. In further embodiments, arylene includes lower arylene. Arylene groups include, but are not limited to, 1,2-, 1,3- and 1,4-phenylene. The term "lower arylene" refers to arylene groups having 6 carbons.

As used herein, "heteroarylene" refers to a divalent monocyclic or multicyclic aromatic ring system, in one embodiment of about 5 to about 15 atoms in the ring(s), where one or more, in certain embodiments 1 to 3, of the atoms in the ring system is a heteroatom, that is, an element other than carbon, including but not limited to, nitrogen, oxygen or sulfur. The term "lower heteroarylene" refers to heteroarylene groups having 5 or 6 atoms in the ring.

As used herein, "heterocyclylene" refers to a divalent monocyclic or multicyclic non-aromatic ring system, in certain embodiments of 3 to 10 members, in one embodiment 4 to 7 members, in another embodiment 5 to 6 members, where one or more, including 1 to 3, of the atoms in the ring system is a heteroatom, that is, an element other than carbon, including but not limited to, nitrogen, oxygen or sulfur.

As used herein, "substituted alkyl," "substituted alkenyl," "substituted alkynyl," "substituted cycloalkyl," "substituted cycloalkenyl," "substituted cycloalkynyl," "substituted aryl," "substituted heteroaryl," "substituted heterocyclyl," "substituted alkylene," "substituted alkenylene," "substituted alkynylene," "substituted cycloalkylene," "substituted cycloalkenylene," "substituted cycloalkynylene," "substituted arylene," "substituted heteroarylene" and "substituted heterocyclylene" refer to alkyl, alkenyl, alkynyl, cycloalkyl, cycloalkenyl, cycloalkynyl, aryl, heteroaryl, heterocyclyl, alkylene, alkenylene, alkynylene, cycloalkylene, cycloalkenylene, cycloalkynylene, arylene, heteroarylene and heterocyclylene groups, respectively, that are substituted with one or more substituents, in certain embodiments one, two, three or four substituents, where the substituents are as defined herein, in one embodiment selected from $Q^1$.

As used herein, "alkylidene" refers to a divalent group, such as =CR'R", which is attached to one atom of another group, forming a double bond. Alkylidene groups include, but are not limited to, methylidene (=CH$_2$) and ethylidene (=CHCH$_3$). As used herein, "arylalkylidene" refers to an alkylidene group in which either R' or R" is an aryl group. "Cycloalkylidene" groups are those where R' and R" are linked to form a carbocyclic ring. "Heterocyclylid-ene" groups are those where at least one of R' and R" contain a heteroatom in the chain, and R' and R" are linked to form a heterocyclic ring.

As used herein, "amido" refers to the divalent group —C(O)NH—. "Thioamido" refers to the divalent group —C(S)NH—. "Oxyamido" refers to the divalent group —OC(O)NH—. "Thiaamido" refers to the divalent group —SC(O)NH—. "Dithiaamido" refers to the divalent group —SC(S)NH—. "Ureido" refers to the divalent group —HNC(O)NH—. "Thioureido" refers to the divalent group —HNC0(S)NH—.

As used herein, "semicarbazide" refers to —NHC(O)NHNH—. "Carbazate" refers to the divalent group —OC(O)NHNH—. "Isothiocarbazate" refers to the divalent group —SC(O)NHNH—. "Thiocarbazate" refers to the divalent group —OC(S)NHNH—. "Sulfonylhydrazide" refers to the divalent group —SO2NHNH—. "Hydraziden refers to the divalent group —C(O)NHNH—. "Azo" refers to the divalent group —N=N—. "Hydrazinyl" refers to the divalent group —NH—NH—.

Where the number of any given substituent is not specified (e.g., haloalkyl), there may be one or more substituents present. For example, "haloalkyl" may include one or more of the same or different halogens. As another example, "$C_{1-3}$alkoxyphenyl" may include one or more of the same or different alkoxy groups containing one, two or three carbons.

As used herein, the abbreviations for any protective groups, amino 10 acids and other compounds, are, unless indicated otherwise, in accord with their common usage, recognized abbreviations, or the IUPAC-IUB Commission on Biochemical Nomenclature (see, (1972) Biochem. 11:942-944).

As employed herein, the following terms have their accepted meaning in the chemical literature.

| | |
|---|---|
| AcOH | acetic acid |
| CDI | carbodiimide |
| CHCl$_3$ | chloroform |
| conc | concentrated |
| DBU | 1,8-diazabicyclo[5.4.0]undec-7-ene |
| DCM | dichloromethane |
| DDQ | 2,3-dichloro-5,6-dicyano-1,4-benzoquninone |
| DIEA | diisopropyl ethylamine |
| DMAP | 4-(dimethylamino) pyridine |
| DME | 1,2-dimethoxyethane |
| DMF | N,N-dimethylformamide |
| DMSO | dimethylsulfoxide |
| ELSD | Evaporative light scattering detector |
| EtOAc | ethyl acetate |
| EtOH | ethanol (100%) |
| Et$_2$O | diethyl ether |

-continued

| | |
|---|---|
| HBTU | 1-H-Benzotriazolium, 1-[bis(dimethylamino)methylene]-hexafluorophosphate(1-),3-oxide O-(Benzotriazol-1-yl)-N,N,N',N' tetramethyluronium hexafluorophosphate |
| Hex | hexanes |
| H$_2$SO$_4$ | sulfuric acid |
| LDA | Lithium di(iso-propyl)amide |
| MeCN | acetonitrile |
| MeOH | methanol |
| NaBH$_3$CN | sodium cyanoborohydride |
| Pd/C | palladium on activated carbon |
| TEA | triethylamine |
| THF | tetrahydrofuran |
| TFA | trifluoroacetic acid |

B. Preferred Embodiments of the Compounds of the Invention

Compounds for use in compositions and methods for modulating the activity of nuclear receptors are provided. In particular, compounds for use in compositions and methods for modulating the farnesoid X receptor) and/or orphan nuclear receptors are provided.

In certain embodiments, the compounds of the invention, as described above in the Summary of the Invention, are compounds of formula (I):

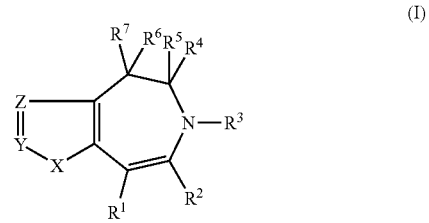

(I)

wherein:
X is NR$^9$, O or S(O)$_t$ (where t is 0 to 2);
Y is CR$^{30}$ or N;
Z is CR$^{31}$ or N;
wherein R$^{30}$ and R$^{31}$ are independently selected from 1a), 1b), 1c),1d), 1e), 1f) and 1g); R$^1$ is independently selected from 2a), 2b), 2c), 2d), 2e), 2f), 2g), 2h), 2i), 2j) 2k) and l); R$^2$ is independently selected from 3a), 3b), 3c), 3d), 3e), 3f), 3g), 3h), 3i) and 3j); R$^3$ is independently selected from 4a), 4b), 4c), 4d), 4e), 4f), 4g), 4h), 4i), 4j), 4k), 4l), 4m), 4n), 4o), 4p) and 4q); R$^9$ when present is independently selected from 5a), 5b), 5c) and 5d); R$^4$, R$^5$, R$^6$ and R$^7$ are each independently selected from 6a)6y).

1 a) R$^{30}$ and R$^{31}$ together with the carbon atoms to which they are attached, form an optionally substituted cycloalkyl ring, optionally substituted cycloalkenyl ring, optionally substituted cycloalkynyl ring, optionally substituted heterocyclyl ring, optionally substituted heteroaryl ring or optionally substituted aryl ring with the exception of substituted or unsubstituted phenyl and substituted or unsubstituted naphthyl;

1 b) R$^{30}$ and R$^{31}$ together with the carbon atoms to which they are attached, form an optionally substituted cycloalkyl ring, optionally substituted cycloalkenyl ring, optionally substituted cycloalkynyl ring, optionally substituted heterocyclyl ring, optionally substituted heteroaryl ring or optionally substituted aryl ring, provided, however, that aryl cannot be phenyl or naphthyl;

1 c) R$^{30}$ and R$^{31}$ together with the carbon atoms to which they are attached, form an optionally substituted cycloalkyl ring, optionally substituted cycloalkenyl ring, optionally substituted cycloalkynyl ring, optionally substituted heterocyclyl ring or optionally substituted heteroaryl ring;

1d) where said cycloalkyl ring, said cycloalkenyl ring, said cycloalkynyl ring, said heterocyclyl ring, said heteroaryl ring in 1c), when substituted, is substituted with substituents selected from the group consisting of halo, pseudohalo, alkyl, haloalkyl, cycloalkyl, heterocyclyl, cycloalkylalkyl, aryl, heteroaryl, aralkyl, heteroaralkyl, halosulfonyl, nitro, —$OR^{70}$, —$SR^{70}$, —$R^{60}$—C(=J)$R^{71}$, —$R^{60}$—N($R^{70}$)C(O)$R^{71}$, —OC(O)$R^{71}$, —$R^{60}$—N($R^{75}$)($R^{76}$), —N($R^{70}$)S(O)$_2R^{71}$ and —S(O)$_2R^{71}$;

each $R^{60}$ is independently a direct bond or alkylene;

each $R^{70}$ is independently hydrogen, alkyl, alkenyl, alkynyl, cycloalkyl, heterocyclyl, aryl, heteroaryl, aralkyl, haloalkyl, heterocyclylalkyl or heteroaralkyl;

each $R^{71}$ is independently hydrogen, alkyl, alkenyl, alkynyl, cycloalkyl, heterocyclyl, aryl, heteroaryl, aralkyl, haloalkyl, heterocyclylalkyl, heteroaralkyl, —$OR^{72}$ or —N($R^{73}$)$R^{74}$;

$R^{72}$, $R^{73}$ and $R^{74}$ are each independently hydrogen, alkyl, alkenyl, alkynyl, cycloalkyl, heterocyclyl, aryl, heteroaryl, aralkyl or heteroaralkyl; or $R^{73}$ and $R^{74}$, together with the nitrogen atom to which they are attached, form a heterocyclyl ring or heteroaryl ring; and $R^{75}$ and $R^{76}$ are each independently hydrogen, alkyl, alkenyl, alkynyl, aryl, aralkyl, heteroaryl, heteroaralkyl, heterocyclyl or heterocyclylalkyl; or $R^{75}$ and $R^{76}$, together with the nitrogen atom to which they are attached, form a heterocyclyl ring or heteroaryl ring;

1e) $R^{30}$ and $R^{31}$ together with the carbon atoms to which they are attached, form a cyclopentyl, cyclohexyl, cycloheptyl or cyclooctyl; and f) $R^{30}$ and $R^{31}$ together with the carbon atoms to which they are attached, form pyrrolidinyl, tetrahydrothiophenyl, tetrahydorfuranyl, oxacyclohexyl, oxacyclohexyl, dioxacyclohexyl, azacyclohexyl, diazacyclohexyl, oxa-azacyclohexyl, thia-azacyclohexyl, thiacyclohexyl or dithiacyclohexyl; and 1g) $R^{30}$ and $R^{31}$ together with the carbon atoms to which they are attached, is pyridazinyl, pyrimidinyl, pyrazinyl, 1,2,3-triazinyl or 1,2,4-triazinyl;

wherein $R^1$ is selected from 2a), 2b), 2c), 2d), 2e), 2f), 2g), 2h), 2i), 2j) 2k) and 1):

2a) $R^1$ is optionally substituted alkyl, optionally substituted aryl, optionally substituted heteroaryl, —C(O)$R^{18}$, —C(O)O$R^{14}$, —C(O)N($R^{15}$)$R^{16}$, or —C(O)N($R^{17}$)N($R^{15}$)$R^{16}$; where $R^{14}$, $R^{15}$, $R^{16}$, $R^{17}$ and $R^{18}$ are each as defined above in the Summary of the Invention; and X,Y,Z, $R^2$—$R^7$ and $R^9$ are each as defined above in the Summary of the Invention;

2b) $R^1$ is independently selected from halo, hydrogen, optionally substituted alkyl, optionally substituted alkenyl, optionally substituted alkynyl, optionally substituted aryl, optionally substituted heteroaryl, optionally substituted cycloalkyl, optionally substituted heterocyclyl, optionally substituted aralkyl, optionally substituted heteroaralkyl, —$OR^{14}$, —$SR^{14}$, —N($R^{15}$)$R^{16}$, —N($R^{15}$)S(O)$_2R^{23}$; —N($R^{17}$)N($R^{15}$)$R^{16}$, —N($R^{17}$)N($R^{15}$)S(O)$_2R^{23}$, —C(O)$R^{18}$, —C(O)$R^{14}$, —C(S)O$R^{14}$, —C(O)S$R^{14}$, —C(O)N($R^{15}$)$R^{16}$, —C(O)N($R^{15}$)S(O)$_2R^{23}$, —C(O)N($R^{15}$)N=$R^{16}$, —C(O)N($R^{17}$)N($R^{15}$)$R^{16}$ and —C(O)N($R^{17}$)N($R^{15}$)S(O)$_2R^{23}$, where $R^{14}$, $R^{15}$, $R^{16}$, $R^{17}$ and $R^{18}$ are selected as described above in the Summary of the Invention 2c) $R^1$ is optionally substituted alkynyl, optionally substituted aryl, optionally substituted heteroaryl, optionally substituted cycloalkyl, optionally substituted heterocyclyl, optionally substituted aralkyl, optionally substituted heteroaralkyl, —$OR^{14}$, —N($R^{15}$)$R^{16}$, —N($R^{17}$)N($R^{15}$)$R^{16}$, —C(O)$R^1$, —C(O)O$R^{14}$, —C(O)N($R^{15}$)$R^{16}$, or —C(O)N($R^{17}$)N($R^{15}$)$R^{16}$; where $R^{14}$, $R^{15}$, $R^{16}$, $R^{17}$ and $R^{18}$ are as described above in the Summary of the Invention;

2d) $R^1$ is —$OR^{14}$, —$SR^{14}$, —N($R^{15}$)$R^{16}$, —N($R^{15}$)S(O)$_2R^{23}$; —N($R^{17}$)N($R^{15}$)$R^{16}$, —N($R^{17}$)N($R^{15}$)S(O)$_2R^{23}$, —C(O)$R^{18}$, —C(O)O$R^{14}$, —C(S)O$R^{14}$, —C(O)S$R^{14}$, —C(O)N($R^{15}$)$R^{16}$, —C(O)N($R^{15}$)S(O)$_2R^{23}$, —C(O)N($R^{15}$)N=$R^{16}$, —C(O)N($R^{17}$)N($R^{15}$)$R^{16}$ or —C(O)N($R^{17}$)N($R^{15}$)S(O)$_2R^{23}$;2e) $R^1$ is —C(O)$R^{18}$, —C(O)O$R^{14}$, —C(S)O$R^{14}$, —C(O)S$R^{14}$, —C(O)N($R^{15}$)$R^{16}$, —C(O)N($R^{15}$)S(O)$_2R^{23}$, —C(O)N($R^{15}$)N=$R^{16}$, —C(O)N($R^{17}$)N($R^{15}$)$R^{16}$ or —C(O)N($R^{17}$)N($R^{15}$)S(O)$_2R^{23}$;

2f) $R^1$ is selected from optionally substituted alkyl, optionally substituted aryl, optionally substituted heteroaryl, —C(O)$R^{18}$, —C(O)O$R^{14}$, —C(O)N($R^{17}$)N$R^{15}R^{16}$ or —C(O)N($R^{15}$)$R^{16}$;

2g) $R^{18}$ in 2e) is optionally substituted alkyl, optionally substituted cycloalkyl, optionally substituted heterocyclyl, or optionally substituted aralkyl and $R^{15}$ and $R^{16}$ are as described above in the Summary of the Invention;

2h) $R^{15}$ in 2e) is optionally substituted alkyl or optionally substituted cycloalkyl;

2i) $R^{15}$ in 2e) is alkyl or cycloalkyl and $R^{16}$ is hydrogen;

2j) $R^1$ is selected from —C(O)$R^{18}$, —C(O)O$R^{14}$, —C(O)N($R^{17}$)N$R^{15}R^{16}$ or —C(O)N($R^{15}$)$R^{16}$ where $R^{14}$, $R^{15}$ and $R^{16}$ are each independently hydrogen, optionally substituted alkyl, optionally substituted cycloalkyl, or optionally substituted heterocyclyl and $R^{18}$ is optionally substituted alkyl;

2k) $R^1$ is —C(O)OCH$_2$CH$_3$, —C(O)OCH$_3$, —C(O)OCH(CH$_3$)$_2$, —C(O)OH, —C(O)OCH$_2$CH$_2$CH$_3$, methylaminocarbonyl, ethylaminocarbonyl, isopropylaminocarbonyl, cyclopropylaminocarbonyl, cyclopentylaminocarbonyl, 2-butylaminocarbonyl, or cyclopropyl methylaminocarbonyl; and 2l) R is —C(O)O$R^{14}$, —C(O)N($R^{15}$)$R^{16}$ and $R^{14}$, $R^{15}$ and $R^{16}$ are each independently hydrogen, optionally substituted alkyl or optionally substituted cycloalkyl;

wherein $R^2$ is selected from 3a), 3b), 3c), 3d), 3e), 3f), 3g), 3h), 3i) and 3j):

3a) $R^2$ is selected from optionally substituted alkyl, optionally substituted aryl, optionally substituted heteroaryl, —(CO)O-(optionally substituted alkyl), —C(O)OH, or —C(O)N($R^{15}$)$R^{16}$, where $R^{15}$ and $R^{16}$ are as described above in the Summary of the Invention;

3b) $R^{15}$ in 3a) is optionally substituted alkyl; and

3c) $R^{15}$ in 3a) is alkyl and $R^{16}$ is hydrogen;

3d) $R^2$ is —C(O)OCH$_2$CH$_3$, —C(O)OCH$_3$, —C(O)OCH(CH$_3$)$_2$, —C(O)OH, —C(O)OCH$_2$CH$_2$CH$_3$, methylaminocarbonyl, ethylaminocarbonyl, isopropylaminocarbonyl, cyclopropylaminocarbonyl, cyclopentylaminocarbonyl, 2-butylaminocarbonyl, or cyclopropyl methylaminocarbonyl.

3e) $R^2$ is hydrogen, halo, optionally substituted alkyl, optionally substituted alkenyl or optionally substituted alkynyl;

3f) $R^2$ is hydrogen, halo or optionally substituted alkyl. In another embodiment;

3g) $R^2$, when substituted, is substituted with halo, pseudohalo, alkyl, alkoxy, alkylenedioxy, haloalkyl, nitro, cyano, alkoxycarbonyl, aryl, halosulfonyl, or haloalkoxy;

3h) $R^2$ is hydrogen or alkyl;

3i) $R^2$ is hydrogen; and

3j) $R^2$ is independently selected from halo, hydrogen, optionally substituted alkyl, optionally substituted alkenyl, optionally substituted alkynyl, optionally substituted aryl, optionally substituted heteroaryl, optionally substituted cycloalkyl, optionally substituted heterocyclyl, optionally substituted aralkyl, optionally substituted heteroaralkyl, —OR$^{14}$, —SR$^{14}$, —N(R$^{15}$)R$^{16}$, —N(R$^{15}$)S(O)$_2$R$^{23}$; —N(R$^{17}$)N(R$^{15}$)R$^{16}$, —N(R$^{17}$)N(R$^{15}$)S(O)$_2$R$^{23}$, —C(O)R$^{18}$, —C(O)OR$^{14}$, —C(S)OR$^{14}$, —C(O)SR$^{14}$, —C(O)N(R$^{15}$)R$^{16}$, —C(O)N(R$^{15}$)S(O)$_2$R$^{23}$, —C(O)N(R$^{15}$)N=R$^{16}$, —C(O)N(R$^{17}$)N(R$^{15}$)R$^{16}$ and —C(O)N(R$^{17}$)N(R$^{15}$)S(O)$_2$R$^{23}$, where R$^{14}$, R$^{15}$, R$^{16}$, R$^{17}$ and R$^{18}$ are selected as described above in the Summary of the Invention;

wherein R$^3$ is selected from 4a), 4b), 4c), 4d), 4e), 4f), 4g), 4h), 4i), 4j), 4k), 4l), 4m), 4n), 4o), 4p) and 4q):

4a) R$^3$ is hydrogen, optionally substituted alkyl, optionally substituted alkenyl, optionally substituted alkynyl, optionally substituted cycloalkyl, optionally substituted aryl, optionally substituted aralkyl, optionally substituted heteroaryl, optionally substituted heterocyclyl, optionally substituted heteroaralkyl, —C(O)R$^{10}$, —C(O)OR$^{10}$, —S(O)$_2$R$^{10}$, —C(O)N(R$^{11}$)R$^{12}$, —C(O)N(R$^{11}$)S(O)$_2$R$^{23}$, —C(O)N(R$^{13}$)N(R$^{11}$)R$^{12}$, —C(O)N(R$^{13}$)N(R$^{11}$)S(O)$_2$R$^{23}$, —N(R$^{13}$)C(O)R$^{10}$, —N(R$^{13}$)C(O)N(R$^{11}$)R$^{12}$, —N(R$^{13}$)C(O)N(R$^{11}$)S(O)$_2$R$^{23}$, —N(R$^{10}$)C(O)N(R$^{13}$)N(R$^{11}$)R$^{12}$, —N(R$^{10}$)C(O)N(R$^{13}$)N(R$^{11}$)S(O)$_2$R$^{23}$, —N(R$^{13}$)C(O)R$^{10}$, —P(O)OR$^{10}$ or —P(O)(OR$^{19}$)OR$^{12}$, where R$^{10}$, R$^{11}$, R$^{12}$, R$^{13}$, R$^{19}$ and R$^{19}$ are as described in the Summary of the Invention;

4b) R$^3$ is —C(O)R$^{10}$, —C(O)OR$^{10}$, —S(O)$_2$R$^{10}$, —C(O)N(R$^{11}$)R$^{12}$, —C(O)N(R$^{11}$)S(O)$_2$R$^{23}$, —C(O)N(R$^{13}$)N(R$^{11}$)R$^{12}$, —C(O)N(R$^{13}$)N(R$^{11}$)S(O)$_2$R$^{23}$, —N(R$^{13}$)C(O)R$^{10}$, —N(R$^{13}$)C(O)N(R$^{11}$)R$^{12}$, —N(R$^{13}$)C(O)N(R$^{11}$)S(O)$_2$R$^{23}$, —N(R$^{10}$)C(O)N(R$^{13}$)N(R$^{11}$)R$^{12}$, —N(R$^{10}$)C(O)N(R$^{13}$)N(R$^{11}$)S(O)$_2$R$^{23}$, —N(R$^{13}$)C(O)OR$^{10}$, —P(O)OR$^{10}$ or —P(O)(OR$^{19}$)OR$^{12}$;

4c) R$^3$ is optionally substituted alkyl, optionally substituted alkenyl, optionally substituted alkynyl, optionally substituted aryl, optionally substituted heteroaryl, optionally substituted cycloalkyl, optionally substituted heterocyclyl, optionally substituted aralkyl, optionally substituted heteroaralkyl, —C(O)R$^{10}$, —C(O)OR$^{10}$, —SO$_2$R$^{10}$, —C(O)N(R$^{11}$)R$^{12}$, —C(O)N(R$^{13}$)N(R$^{11}$)R$^{12}$, —N(R$^{13}$)C(O)R$^{10}$, —N(R$^{13}$)C(O)N(R$^{11}$)R$^{12}$, —N(R$^{10}$)C(O)N(R$^{13}$)N(R$^{11}$)R$^{12}$, —N(R$^{13}$)C(O)OR$^{10}$, —P(O)OR$^{10}$, or —P(O)(OR$^{19}$)OR$^{12}$; where R$^{10}$, R$^{11}$, R$^{12}$, R$^{13}$ and R$^{19}$ are selected as described in the Summary of the Invention.;

4d) R$^3$ is hydrogen, —C(O)R$^{10}$, —C(O)OR$^{10}$, —S(O)$_2$R$^{10}$ or —C(O)N(R$^{11}$)R$^{12}$; where R$^{10}$, R$^{11}$ and R$^{12}$ are as described in the Summary of the Invention;

4e) R$^{10}$ in 4d) is optionally substituted aryl, optionally substituted heteroaryl, optionally substituted alkyl, or optionally substituted aralkyl;

4e) R$^{10}$ in 4e), when substituted, is substituted with halo, pseudohalo, alkyl, alkoxy, alkylenedioxy, haloalkyl, nitro, cyano, halosulfonyl, aryl, or —C(O)OR$^{72}$, where R$^{72}$ is alkyl. In another embodiment, R$^{11}$ and R$^{12}$ are each independently hydrogen, optionally substituted alkyl, optionally substituted cycloalkyl, or optionally substituted heterocyclyl; or R$^{11}$ and R$^{12}$, together with the atoms to which they are attached, form an optionally substituted heterocyclyl ring or an optionally substituted heteroaryl ring;

4f) R$^{11}$ in 4d) is hydrogen, or optionally substituted alkyl;

4g) R$^{11}$ in 4d) is hydrogen or alkyl;

4h) R$^{11}$ in 4d) is hydrogen;

4i) R$^3$ is —C(O)-(optionally substituted aryl), —C(O)-(optionally substituted heteroaryl), —C(O)-(optionally substituted alkyl), hydrogen, —SO$_2$-(optionally substituted aryl), —C(O)(CH$_2$)$_r$-(optionally substituted aryl) where r is an integer from 1-4, —C(O)O-(optionally substituted aryl), or —C(O)N(H)-(optionally substituted aryl).

4j) R$^3$ is —C(O)-(optionally substituted aryl) where the substituents, when present, are halo, pseudohalo, alkyl, alkoxy, alkylenedioxy, haloalkyl, nitro, cyano, —C(O)O-alkyl, aryl or —SO$_2$F. In another embodiment, R$^3$ is —C(O)-heteroaryl;

4k) R$^3$ is —C(O)-alkyl;

4l) R$^3$ is hydrogen;

4m) R$^3$ is —SO$_2$-(optionally substituted aryl), where the substituents, when present, are alkyl, halo, alkoxy or haloalkoxy;

4n) R$^3$ is —C(O)-(CH$_2$)$_r$-aryl where r is 1 or 2;

4o) R$^3$ is —C(O)—O-(optionally substituted aryl), where the substituents; when present, are halo, alkoxy or alkyl;

4p) R$^3$ is —C(O)N(H)-(optionally substituted aryl), where the substituents, when present, are halo, alkoxy or alkyl; and 4q) R$^3$ is selected from hydrogen, —C(O)-(4-chlorophenyl), —C(O)-(4-fluorophenyl), —C(O)-(2-furyl), —C(O)-(2,4-dichlorophenyl), —C(O)-(3-nitrophenyl), —C(O)-(phenyl), —C(O)(methyl), —C(O)-(4-tert-butylphenyl), —SO$_2$(4-methylphenyl), —SO$_2$-(4-tert-butylphenyl), —C(O)42-methoxyphenyl), —C(O)-(3-methoxyphenyl), —C(O)-(4-methoxyphenyl), —C(O)-(benzyl), —C(O)O-phenyl, —C(O)O-(4-chlorophenyl), —C(O)O-(4-methoxyphenyl), —C(O)O4-methylphenyl), —C(O)N(H)-phenyl, —C(O)N(H)-(4-chlorophenyl), —C(O)N(H)-(2,4-dichlorophenyl), —C(O)N(H)-(4-methoxyphenyl), —C(O)N(H)-(4-methylphenyl), —C(O)-(3,4-methylenedioxyphenyl), —C(O)-n-octyl, —C(O)—CH$_2$CH$_2$phenyl, —SO$_2$-(4-chlorophenyl), —SO$_2$-(4-methoxyphenyl), —SO$_2$-(3,4-dimethoxyphenyl), —SO$_2$-(4-trifluoromethoxyphenyl), —C(O)-(2,3-difluorophenyl), —C(O)-(2,4-difluorophenyl), —C(O)-(2,5-difluorophenyl), —C(O)-(2,6-difluorophenyl), —C(O)-(3,4-difluorophenyl), —C(O)-(3,5-difluorophenyl), —C(O)-(2,3,4trifluorophenyl), —C(O)-(2,3,6-trifluorophenyl), —C(O)-(2,4,5-trifluorophenyl), —C(O)-(2,3,4,5-tetrafluorophenyl), —C(O)-(2,3,4,5,6-pentafluorophenyl), —C(O)-(2,5-bis(trifluoromethyl)phenyl), —C(O)-(3,5-bis(trifluoromethyl)-phenyl), —C(O)-(2-trifluoromethylphenyl), —C(O)-(3-trifluoromethylphenyl), —C(O)-(4-trifluoromethylphenyl), —C(O)-(2-fluorophenyl), —C(O)-(3-fluorophenyl), —C(O)-(4-nitrophenyl), —C(O)-(3-nitro-4-methylphenyl), —C(O)-(4-methoxycarbonylphenyl), —C(O)-(3-pyridyl), —C(O)-(4-pyridyl), —C(O)-(3-cyanophenyl), —C(O)-(3,4-dimethoxyphenyl), —C(O)-(2-methylphenyl), —C(O)-(4-methylphenyl), —C(O)-(2-chlorophenyl), —C(O)-(2-naphthyl), —C(O)-(4-biphenyl), —C(O)-(4-fluorosulfonylphenyl), —C(O)-(3-methylphenyl), and —C(O)-(3-chlorophenyl);

wherein R$^9$ is selected from 5a), 5b), 5c) and 5d):

5a) R$^9$ is hydrogen or optionally substituted alkyl;

5b) R$^9$ is optionally substituted alkyl which, when substituted, is substituted with halo, pseudohalo, alkyl, alkoxy, alkylenedioxy, haloalkyl, nitro, cyano, alkoxycarbonyl, aryl, halosulfonyl, or haloalkoxy;

5c) In another embodiment, R$^9$ is hydrogen, optionally substituted alkyl, or —S(O)$_2$R$^{43}$; wherein R$^{43}$ is as defined in the Summary of the Invention; and 5d) R$^9$ is hydrogen;

wherein R$^4$, R$^5$, R$^6$ and R$^7$ are each independently selected from 6a)-6y):6a) R$^4$, R$^5$, R$^6$ and R$^7$ are each independently selected from a group consisting of hydrogen, halo, optionally substituted alkyl, optionally substituted alkenyl, optionally substituted alkynyl, optionally substituted aryl, optionally substituted heteroaryl, optionally substituted cycloalkyl, optionally substituted heterocyclyl, optionally substituted aralkyl, optionally substituted heteroaralkyl, —OR$^{14}$, —SR$^{14}$, —S(O)$_2$R$^{14}$, —N(R$^{15}$)R$^{16}$, —N(R$^{15}$)S(O)$_2$R$^{23}$, —N(R$^{15}$)C(O)R$^{23}$, —C(O)R$^{18}$, —C(O)OR$^{20}$, —C(O)N(R$^{21}$)R$^{22}$, —C(O)N(R$^{21}$)S(O)$_2$R$^{23}$; —C(O)N(R$^{24}$)N(R$^{21}$)

$R^{22}$ and —C(O)N($R^{24}$)N($R^{21}$)S(O)$_2R^{23}$ where $R^{14}$, $R^{15}$, $R^{16}$, $R^{18}$, $R^{20}$, $R^{21}$, $R^{22}$, $R^{23}$ and $R^{24}$ are as described in the Summary of the Invention;

6b) $R^4$, $R^5$, $R^6$ and $R^7$ are independently selected from hydrogen, halo, optionally substituted alkyl, —C(O)OH, —C(O)O-alkyl, or —C(O)N($R^{21}$)$R^{22}$; where $R^{21}$ and $R^{22}$ are each independently hydrogen, optionally substituted alkyl, or together with the nitrogen atom to which they are attached, form an optionally substituted heterocyclic or heteroaryl ring.

6c) $R^4$, $R^5$, $R^6$ and $R^7$ are independently selected from hydrogen, halo, optionally substituted alkyl, —C(O)OH, —C(O)—O-alkyl, or —C(O)N($R^{21}$)$R^{22}$; where $R^{21}$ and $R^{22}$ are each independently hydrogen or alkyl, or together with the nitrogen atom to which they are attached, form a heterocyclic ring.

6d) $R^4$, $R^5$, $R^6$ and $R^7$ are independently selected from hydrogen, halo, methyl, ethyl, —C(O)OH, —C(O)OCH$_2$CH$_3$, —C(O)—N(H)CH$_2$CH$_3$, —C(O)-piperidin-1-yl, or —CH$_2$OC(O)-(4-fluorophenyl).

6e) $R^4$ and $R^5$ or $R^6$ and $R^7$, together with the carbon atom to which they are attached, form an optionally substituted cycloalkyl, optionally substituted heterocyclyl, an optionally substituted cycloalkenyl ring, or together form a double bond and the others of $R^4$, $R^5$, $R^6$ and $R^7$ are as described above; or $R^6$ and $R^7$, together form an oxo, thioxo, optionally substituted imino, optionally substituted oxime or an optionally substituted hydrazone, or $R^6$ and $R^7$, together with the carbon atom to which they are attached, form an optionally substituted exocyclic double bond, and $R^4$ and $R^5$ are as described above;

6f) $R^4$ and $R^5$ together with the carbon atom to which they are attached, form an optionally substituted cycloalkyl or optionally substituted cycloalkenyl and $R^6$ and $R^7$ together, with the carbon atom to which they are attached, form an optionally substituted cycloalkyl or optionally substituted cycloalkenyl.;

6g) $R^4$, $R^5$, $R^6$ and $R^7$ are each independently hydrogen, halo or optionally substituted alkyl;

6h) $R^4$, $R^5$, $R^6$ and $R^7$ are each optionally substituted alkyl;

6i) $R^4$ and $R^5$ are each hydrogen or optionally substituted alkyl and $R^6$ and $R^7$ are each optionally substituted alkyl;

6j) $R^4$ and $R^5$ are each hydrogen and $R^6$ and $R^7$ are each optionally substituted alkyl;

6k) In another embodiment, $R^6$ and $R^7$ are each independently hydrogen or optionally substituted alkyl and $R^4$ and $R^5$ are each optionally substituted alkyl;

6l) $R^6$ and $R^7$ are each hydrogen and $R^4$ and $R^5$ are each optionally substituted alkyl;

6m) $R^4$ and $R^5$ are each hydrogen or optionally substituted alkyl and $R^6$ and $R^7$ together with the carbon atom to which they are attached, form an optionally substituted cycloalkyl or optionally substituted cycloalkenyl ring;

6n) $R^4$ and $R^5$ are each hydrogen and $R^6$ and $R^7$ together with the carbon atom to which they are attached, form an optionally substituted cycloalkyl or optionally substituted cycloalkenyl ring;

6o) $R^4$ and $R^5$ are each optionally substituted alkyl and $R^6$ and $R^7$ together with the carbon atom to which they are attached, form an optionally substituted cycloalkyl or optionally substituted cycloalkenyl ring;

6p) $R^6$ and $R^7$ are each hydrogen or optionally substituted alkyl and $R^4$ and $R^5$ together with the carbon atom to which they are attached, form an optionally substituted cycloalkyl or optionally substituted cycloalkenyl ring;

6q) $R^6$ and $R^7$ are each hydrogen and $R^4$ and $R^5$ together with the carbon atom to which they are attached, form an optionally substituted cycloalkyl or optionally substituted cycloalkenyl ring;

6r) $R^6$ and $R^7$ are each optionally substituted alkyl and $R^4$ and $R^5$ together with the carbon atom to which they are attached, form an optionally substituted cycloalkyl or optionally substituted cycloalkenyl ring;

6s) $R^4$ and $R^5$ are optionally substituted alkyl, or $R^4$ and $R^5$ together with the carbon atom to which they are attached, form cycloalkyl, and $R^6$ and $R^7$ are each hydrogen;

6t) $R^4$ and $R^5$ are hydrogen and $R^6$ and $R^7$ are each optionally substituted alkyl, or $R^6$ and $R^7$ together with the carbon atom to which they are attached, independently form an optionally substituted cycloalkyl, optionally substituted heterocyclyl, optionally substituted cycloalkenyl ring, or $R^6$ and $R^7$, together form an optionally substituted imino, optionally substituted thioxo, optionally substituted oxo, optionally substituted oxime or an optionally substituted hydrazone; or $R^6$ and $R^7$, together with the carbon atom to which they are attached, form an endocyclic or an optionally substituted exocyclic double bond;

6u) $R^4$ and $R^5$ are hydrogen and $R^6$ and $R^7$ are each optionally substituted lower alkyl or $R^6$ and $R^7$ together with the carbon atom to which they are attached form cycloalkyl;

6v) $R^4$ is hydrogen, optionally substituted alkyl, —C(O)OR$^{20}$ or —C(O)N($R^{21}$)$R^{22}$, where $R^{20}$ is hydrogen, alkyl and $R^{21}$ and $R^{22}$ are each independently hydrogen, optionally substituted alkyl, or together with the nitrogen atom to which they are attached, form an optionally substituted heterocyclyl ring or heteroaryl ring. In another embodiment, $R^4$, $R^{20}$, $R^{21}$, and $R^{22}$, when substituted, are independently substituted with halo, pseudohalo, alkoxy, alkylenedioxy, haloalkyl, nitro, cyano, alkoxycarbonyl, aryl, halosulfonyl, or haloalkoxy; and 6w) $R^4$ is —C(O)N($R^{21}$)$R^{22}$ and $R^{21}$ and $R^{22}$, together with the nitrogen atom to which they are attached, form an optionally substituted heterocyclyl ring or heteroaryl ring optionally substituted with halo, pseudohalo, alkyl, alkoxy, alkylenedioxy, haloalkyl, nitro, cyano, alkoxycarbonyl, aryl, halosulfonyl or haloalkoxy; 6x) $R^6$ and $R^7$ are independently hydrogen, optionally substituted alkyl, —OR$^{14}$, or $R^6$ and $R^7$ together form an optionally substituted cycloalkyl ring, optionally substituted heterocyclyl ring or an optionally substituted cycloalkenyl ring; and 6y) $R^4$, $R^5$, $R^6$ and $R^7$, when substituted, is independently substituted with halo, pseudohalo, alkyl, alkoxy, alkylenedioxy, haloalkyl, nitro, cyano, alkoxycarbonyl, aryl, halosulfonyl, or haloalkoxy.

In another embodiment, Y is CR$^{30}$ and $R^{30}$ is as defined above in the Summary of the Invention. In another embodiment, Y is CR$^{30}$ and Z is CR$^{31}$, and $R^{30}$ and $R^{31}$ are defined as defined above in the Summary of the Invention. In another embodiment, $R^{30}$ and $R^{31}$ are each independently selected from the group consisting of halo, hydrogen, optionally substituted alkyl, optionally substituted alkenyl, optionally substituted alkynyl, optionally substituted aryl, optionally substituted heteroaryl, optionally substituted cycloalkyl, optionally substituted heterocyclyl, optionally substituted aralkyl, optionally substituted heteroaralkyl, —OR$^{32}$, —SR$^{32}$, —N($R^{33}$)$R^{34}$, —N($R^{33}$)S(O)$_2$ $R^{23}$; —N($R^{35}$)N($R^{33}$)$R^{34}$, —N($R^{35}$)N($R^{33}$)S(O)$_2R^{23}$, —C(O)R$^{36}$, —C(O)OR$^{32}$, —C(S)OR$^{32}$, —C(O)SR$^{32}$, —C(O)N($R^{33}$)$R^{34}$, —C(O)N($R^{33}$)S(O)$_2R^{23}$ and —C(O)N($R^{35}$)N($R^{33}$)$R^{34}$ or —C(O)N($R^{35}$)N($R^{33}$)S(O)$_2$ $R^{23}$.

Preferred embodiments are those compounds wherein X is —N($R^9$); Y is CR$^{30}$ and Z is CR$^{31}$. A further preferred embodiment are those compounds where X is —N($R^9$); Y is $CR^{30}$; Z is $CR^{31}$; $R^1$ is —C(O)O$R^{14}$, —C(S)O$R^{14}$, —C(O)S$R^{14}$, —C(O)N($R^{15}$)$R^{16}$, —C(O)N($R^{15}$)S(O)$R^{23}$, —C(O)N($R^{15}$)N=$R^{16}$, —C(O)N($R^{17}$)N($R^{15}$)$R^{16}$ or —C(O)N($R^{17}$)N($R^{15}$)S(O)$_2$$R^{23}$; $R^2$ is hydrogen, halo or alkyl; $R^3$ is —C(O)$R^{10}$;

$R^4$, $R^5$, $R^6$ and $R^7$ are each independently selected from a group consisting of hydrogen, halo, optionally substituted alkyl, optionally substituted alkenyl, optionally substituted alkynyl;

$R^6$ and $R^7$ together with the carbon atom to which they are attached, form an optionally substituted cycloalkyl ring, optionally substituted heterocyclyl ring or an optionally substituted cycloalkenyl ring, and $R^4$ and $R^5$ are as described above;

$R^9$ is hydrogen, optionally substituted alkyl, —C(O)$R^{18}$, —C(O)O$R^{20}$ or —S(O)$_2$$R^{23}$; $R^{10}$ is an optionally substituted aryl or an optionally substituted heteroaryl;

$R^{14}$, $R^{15}$, $R^{16}$, $R^{17}$ $R^{20}$ and $R^{23}$ are as described above in the Summary of the Invention.

$R^{30}$ and $R^{31}$ together with the carbon atoms to which they are attached, form an optionally substituted cycloalkyl ring, optionally substituted cycloalkenyl ring, optionally substituted cycloalkynyl ring, optionally substituted heterocyclyl ring, optionally substituted heteroaryl ring or optionally substituted aryl ring, provided, however, that aryl cannot be phenyl.

Other preferred embodiments are those compounds wherein X is —N($R^9$); Y is $CR^{30}$; Z is $CR^{31}$; $R^1$ is —C(O)O$R^{14}$ or —C(O)N($R^{15}$)$R^{16}$; $R^2$ is hydrogen, halo or optionally substituted alkyl; $R^3$ is —C(O)$R^{10}$; $R^4$ is hydrogen, halo, optionally substituted alkyl, optionally substituted alkenyl, optionally substituted alkynyl, —C(O)N($R^{21}$)$R^{22}$ or —C(O)O$R^{20}$; $R^5$, $R^6$ and $R^7$ are each independently hydrogen, halo, optionally substituted alkyl, optionally substituted alkenyl, optionally substituted alkynyl, or $R^6$ and $R^7$, together with the carbon to which they are attached, form a heterocyclyl ring, an optionally substituted cycloalkyl ring or an optionally substituted cycloalkenyl ring and $R^5$ is as described above; $R^9$ is hydrogen, optionally substituted alkyl, —C(O)$R^{18}$, —C(O)O$R^{20}$ or —S(O)$_2$$R^{23}$; $R^{10}$ is independently optionally substituted aryl or optionally substituted heteroaryl; $R^{14}$, $R^{15}$ and $R^{16}$ are each independently hydrogen, optionally substituted alkyl or optionally substituted cycloalkyl; $R^{20}$, $R^{21}$ and $R^{22}$ is as described above in the Summary of the Invention; $R^{30}$ and $R^{31}$ together with the carbon atoms to which they are attached, form a cycloalkyl ring.

A preferred compound of this embodiment is 3-(4-Fluorobenzoyl)-1,1-dimethyl-1,2,3,6,7,8,9,10-octahydro-azepino[4,5-b]indole-5-carboxylic acid ethyl ester.

Other preferred embodiments are those compounds wherein X is —N($R^9$); Y is $CR^{30}$; Z is C $R^{31}$; $R^1$ is —C(O)O$R^{14}$ or —C(O)N($R^{15}$)$R^{16}$; $R^2$ is hydrogen, halo or optionally substituted alkyl; $R^3$ is —C(O)$R^{10}$; $R^4$ is hydrogen, halo, optionally substituted alkyl, optionally substituted alkenyl, optionally substituted alkynyl, —C(O)N($R^{21}$)$R^{22}$ or —C(O)O$R^{20}$; $R^5$, $R^6$ and $R^7$ are each independently hydrogen, halo, optionally substituted alkyl, optionally substituted alkenyl, optionally substituted alkynyl, or $R^6$ and $R^7$, together with the carbon to which they are attached, form a heterocyclyl ring, an optionally substituted cycloalkyl ring or an optionally substituted cycloalkenyl ring and $R^5$ is as described above; $R^9$ is hydrogen, optionally substituted alkyl, —C(O)$R^{18}$, —C(O)O$R^{20}$ or —S(O)$_2$$R^{23}$; $R^{10}$ is independently optionally substituted aryl or optionally substituted heteroaryl; $R^{14}$, $R^{15}$ and $R^{16}$ are each independently hydrogen, optionally substituted alkyl or optionally substituted cycloalkyl; $R^{20}$, $R^{21}$ and $R^{22}$ is as described above in the Summary of the Invention; $R^{30}$ and $R^{31}$ together with the carbon atoms to which they are attached, form a cycloalkyl ring substituted with halo, pseudohalo, alkyl, haloalkyl, cycloalkyl, heterocyclyl, cycloalkylalkyl, aryl, heteroaryl, aralkyl, heteroaralkyl, halosulfonyl, nitro, —O$R^{70}$, —S$R^{70}$, —$R^{60}$—C(=J)$R^{71}$, —$R^{60}$—N($R^{70}$)C(O)$R^{17}$, —OC(O)$R^{71}$, —$R^{60}$—N($R^{75}$)($R^{76}$), —N($R^{70}$)S(O)$_2$$R^{71}$ and —S(O)$_2$$R^{71}$;

each $R^{60}$ is independently a direct bond or alkylene;

each $R^{70}$ is independently hydrogen, alkyl, alkenyl, alkynyl, cycloalkyl, heterocyclyl, aryl, heteroaryl, aralkyl, haloalkyl, heterocyclylalkyl or heteroaralkyl;

each $R^{71}$ is independently hydrogen, alkyl, alkenyl, alkynyl, cycloalkyl, heterocyclyl, aryl, heteroaryl, aralkyl, haloalkyl, heterocyclylalkyl, heteroaralkyl, —O$R^{72}$ or —N($R^{73}$)$R^{74}$;

$R^{72}$, $R^{73}$ and $R^{74}$ are each independently hydrogen, alkyl, alkenyl, alkynyl, cycloalkyl, heterocyclyl, aryl, heteroaryl, aralkyl or heteroaralkyl; or $R^{73}$ and $R^{74}$, together with the nitrogen atom to which they are attached, form a heterocyclyl ring or heteroaryl ring; and $R^{75}$ and $R^{76}$ are each independently hydrogen, alkyl, alkenyl, alkynyl, aryl, aralkyl, heteroaryl, heteroaralkyl, heterocyclyl or heterocyclylalkyl; or $R^{75}$ and $R^{76}$, together with the nitrogen atom to which they are attached, form a heterocyclyl ring or heteroaryl ring.

Other preferred embodiments are those compounds wherein X is —N($R^9$); Y is $CR^{30}$; Z is $CR^{31}$; $R^1$ is —C(O)O$R^{14}$ or —C(O)N($R^{15}$)$R^{16}$; $R^2$ is hydrogen, halo or optionally substituted alkyl; $R^3$ is —C(O)$R^{10}$; $R^4$ is hydrogen, halo, optionally substituted alkyl, optionally substituted alkenyl, optionally substituted alkynyl, —C(O)N($R^{21}$)$R^{22}$ or —C(O)O$R^{20}$; $R^5$, $R^6$ and $R^7$ are each independently hydrogen, halo, optionally substituted alkyl, optionally substituted alkenyl, optionally substituted alkynyl, or $R^6$ and $R^7$, together with the carbon to which they are attached, form a heterocyclyl ring, an optionally substituted cycloalkyl ring or an optionally substituted cycloalkenyl ring and $R^5$ is as described above; $R^9$ is hydrogen, optionally substituted alkyl, —C(O)$R^{18}$, —C(O)O$R^{20}$ or —S(O)$_2$$R^{23}$; $R^{10}$ is independently optionally substituted aryl or optionally substituted heteroaryl; $R^{14}$, $R^{15}$ and $R^{16}$ are each independently hydrogen, optionally substituted alkyl or optionally substituted cycloalkyl; $R^{20}$, $R^{21}$ and $R^{22}$ is as described above in the Summary of the Invention; $R^{30}$ and $R^{31}$ together with the carbon atoms to which they are attached, form a heterocyclyl ring.

Other preferred embodiments are those compounds wherein X is —N($R^9$); Y is $CR^{30}$; Z is $CR^{31}$; $R^1$ is —C(O)O$R^{14}$ or —C(O)N($R^{15}$)$R^{16}$; $R^2$ is hydrogen, halo or optionally substituted alkyl; $R^3$ is —C(O)$R^{10}$; $R^4$ is hydrogen, halo, optionally substituted alkyl, optionally substituted alkenyl, optionally substituted alkynyl, —C(O)N($R^{21}$)$R^{22}$ or —C(O)O$R^{20}$; $R^5$, $R^6$ and $R^7$ are each independently hydrogen, halo, optionally substituted alkyl, optionally substituted alkenyl, optionally substituted alkynyl, or $R^6$ and $R^7$, together with the carbon to which they are attached, form a heterocyclyl ring, an optionally substituted cycloalkyl ring or an optionally substituted cycloalkenyl ring and $R^5$ is as described above; $R^9$ is hydrogen, optionally substituted alkyl, —C(O)$R^{18}$, 13 C(O)O$R^{20}$ or —S(O)$_2$$R^{23}$; $R^{10}$ is independently optionally substituted aryl or optionally substituted heteroaryl; $R^{14}$, $R^{15}$ and $R^{16}$ are each independently hydrogen, optionally substituted alkyl or optionally substituted cycloalkyl; $R^{20}$, $R^{21}$ and $R^{22}$ is as described above in the Summary of the Invention; $R^{30}$ and $R^{31}$ together with the carbon atoms to which they are attached, form a heterocyclyl ring substituted with halo, pseudohalo, alkyl, haloalkyl, cycloalkyl, heterocyclyl, cycloalkylalkyl, aryl, heteroaryl, aralkyl, heteroaralkyl, halosulfonyl, nitro, —OR⁷⁰, —SR⁷⁰, —R⁶⁰—C(=J)R⁷¹, —R⁶⁰—N(R⁷⁰)C(O)R⁷¹, —OC(O)R⁷¹, —R⁶⁰—N(R⁷⁵)(R⁷⁶), —N(R⁷⁰)S(O)₂R⁷¹ and —S(O)₂R⁷¹;

each R⁶⁰ is independently a direct bond or alkylene;

each R⁷⁰ is independently hydrogen, alkyl, alkenyl, alkynyl, cycloalkyl, heterocyclyl, aryl, heteroaryl, aralkyl, haloalkyl, heterocyclylalkyl or heteroaralkyl;

each R⁷¹ is independently hydrogen, alkyl, alkenyl, alkynyl, cycloalkyl, heterocyclyl, aryl, heteroaryl, aralkyl, haloalkyl, heterocyclylalkyl, heteroaralkyl, —OR⁷² or —N(R⁷³)R⁷⁴;

R⁷², R⁷³ and R⁷⁴ are each independently hydrogen, alkyl, alkenyl, alkynyl, cycloalkyl, heterocyclyl, aryl, heteroaryl, aralkyl or heteroaralkyl; or R⁷³ and R⁷⁴, together with the nitrogen atom to which they are attached, form a heterocyclyl ring or heteroaryl ring; and R⁷⁵ and R⁷⁶ are each independently hydrogen, alkyl, alkenyl, alkynyl, aryl, aralkyl, heteroaryl, heteroaralkyl, heterocyclyl or heterocyclylalkyl; or R⁷⁵ and R⁷⁶, together with the nitrogen atom to which they are attached, form a heterocyclyl ring or heteroaryl ring.

Other preferred embodiments are those compounds wherein X is —N(R⁹); Y is CR³⁰; Z is CR³¹; R¹ is —C(O)OR¹⁴ or —C(O)N(R¹⁵)R¹⁶; R² is hydrogen, halo or optionally substituted alkyl; R³ is —C(O)R¹⁰; R⁴ is hydrogen, halo, optionally substituted alkyl, optionally substituted alkenyl, optionally substituted alkynyl, —C(O)N(R²¹)R²² or —C(O)OR²⁰; R⁵, R⁶ and R⁷ are each independently hydrogen, halo, optionally substituted alkyl, optionally substituted alkenyl, optionally substituted alkynyl, or R⁶ and R⁷, together with the carbon to which they are attached, form a heterocyclyl ring, an optionally substituted cycloalkyl ring or an optionally substituted cycloalkenyl ring and R⁵ is as described above; R⁹ is hydrogen, optionally substituted alkyl, —C(O)R¹⁸, —C(O)OR²⁰ or —S(O)₂R²³; R¹⁰ is independently optionally substituted aryl or optionally substituted heteroaryl; R¹⁴, R¹⁵ and R¹⁶ are each independently hydrogen, optionally substituted alkyl or optionally substituted cycloalkyl; R²⁰, R²¹ and R²² is as described above in the Summary of the Invention; R³⁰ and R³¹ together with the carbon atoms to which they are attached, form a heteroaryl ring.

Other preferred embodiments are those compounds wherein X is —N(R⁹); Y is CR³⁰; Z is CR³¹; R¹ is —C(O)OR¹⁴ or —C(O)N(R¹⁵)R¹⁶; R² is hydrogen, halo or optionally substituted alkyl; R³ is —C(O)R¹⁰; R⁴ is hydrogen, halo, optionally substituted alkyl, optionally substituted alkenyl, optionally substituted alkynyl, —C(O)N(R²¹)R²² or —C(O)OR²⁰; R⁵, R⁶ and R⁷ are each independently hydrogen, halo, optionally substituted alkyl, optionally substituted alkenyl, optionally substituted alkynyl, or R⁶ and R⁷, together with the carbon to which they are attached, form a heterocyclyl ring, an optionally substituted cycloalkyl ring or an optionally substituted cycloalkenyl ring and R⁵ is as described above; R⁹ is hydrogen, optionally substituted alkyl, —C(O)R¹⁸, —C(O)OR²⁰ or —S(O)₂R²³; R¹⁰ is independently optionally substituted aryl or optionally substituted heteroaryl; R¹⁴, R¹⁵ and R¹⁶ are each independently hydrogen, optionally substituted alkyl or optionally substituted cycloalkyl; R²⁰, R²¹ and R²² is as described above in the Summary of the Invention; R³⁰ and R³¹ together with the carbon atoms to which they are attached, form a heteroaryl ring substituted with halo, pseudohalo, alkyl, haloalkyl, cycloalkyl, heterocyclyl, cycloalkylalkyl, aryl, heteroaryl, aralkyl, heteroaralkyl, halosulfonyl, nitro, —OR⁷⁰, —SR⁷⁰, —R⁶⁰—C(=J)R⁷¹, —R⁶⁰—N(R⁷⁰)C(O)R⁷¹, —OC(O)R⁷¹, —R⁶⁰—N(R⁷⁵)(R⁷⁶), —N(R⁷⁰)S(O)₂R⁷¹ and —S(O)₂R⁷¹;

each R⁶⁰ is independently a direct bond or alkylene;

each R⁷⁰ is independently hydrogen, alkyl, alkenyl, alkynyl, cycloalkyl, heterocyclyl, aryl, heteroaryl, aralkyl, haloalkyl, heterocyclylalkyl or heteroaralkyl;

each R⁷¹ is independently hydrogen, alkyl, alkenyl, alkynyl, cycloalkyl, heterocyclyl, aryl, heteroaryl, aralkyl, haloalkyl, heterocyclylalkyl, heteroaralkyl, —OR⁷² or —N(R⁷³)R⁷⁴;

R⁷², R⁷³ and R⁷⁴ are each independently hydrogen, alkyl, alkenyl, alkynyl, cycloalkyl, heterocyclyl, aryl, heteroaryl, aralkyl or heteroaralkyl; or R⁷³ and R⁷⁴, together with the nitrogen atom to which they are attached, form a heterocyclyl ring or heteroaryl ring; and R⁷⁵ and R⁷⁶ are each independently hydrogen, alkyl, alkenyl, alkynyl, aryl, aralkyl, heteroaryl, heteroaralkyl, heterocyclyl or heterocyclylalkyl; or R⁷⁵ and R⁷⁶, together with the nitrogen atom to which they are attached, form a heterocyclyl ring or heteroaryl ring.

Another embodiment is a compound having the formula (III):

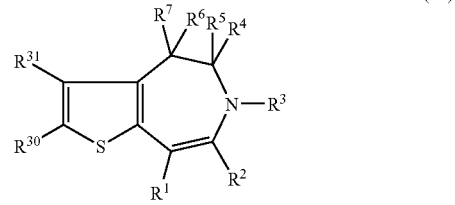

or a pharmaceutically acceptable derivative thereof, wherein:

R¹ is —C(O)OR¹⁴, —C(S)OR¹⁴, —C(O)SR¹⁴, —C(O)N(R¹⁵)R¹⁶, —C(O)N(R¹⁵)S(O)R²³, —C(O)N(R¹⁵)N=R¹⁶, —C(O)N(R¹⁷)N(R¹⁵)R¹⁶ or —C(O)N(R¹⁷)N(R¹⁵)S(O)₂R²³;

R² is hydrogen, halo or alkyl;

R³ is —C(O)R¹⁰;

R⁴ is selected from a group consisting of hydrogen, halo, optionally substituted alkyl, optionally substituted alkenyl, optionally substituted alkynyl, —C(O)OR²⁰ and —C(O)N(R¹¹)R¹²;

R⁵, R⁶ and R⁷ are each independently selected from a group consisting of hydrogen, halo, optionally substituted alkyl, optionally substituted alkenyl and optionally substituted alkynyl; or R⁶ and R⁷ together with the carbon atom to which they are attached, form an optionally substituted cycloalkyl, optionally substituted heterocyclyl or an optionally substituted cycloalkenyl ring, and R⁵ is as described above;

R⁹ is hydrogen, optionally substituted alkyl, —C(O)R¹⁸, —C(O)OR²⁰ or —S(O)₂R²³; and R¹⁰ is an optionally substituted aryl or an optionally substituted heteroaryl; and R³⁰ and R³¹ are each independently selected from a group consisting of optionally substituted aryl, optionally substituted aralkyl, optionally substituted heteroaryl, optionally substituted heteroaralkyl, optionally substituted cycloalkyl, optionally substituted heterocyclyl, —C(O)R³⁶, —C(O)OR³², —C(S)OR³², —C(O)SR³², —C(O)N(R³³)R³⁴, —C(O)N(R³³)S(O)₂R²³, —C(O)N(R³⁵)N(R³³)R³⁴ and —C(O)N(R³⁵)N(R³³)S(O)₂R²³; or $R^{30}$ and $R^{31}$ together with the carbon atoms to which they are attached, form an optionally substituted cycloalkyl ring, optionally substituted cycloalkenyl ring, optionally substituted cycloalkynyl ring, optionally substituted heterocyclyl ring, optionally substituted heteroaryl ring or optionally substituted aryl ring, provided, however, that aryl cannot be phenyl.

In another embodiment, the invention comprises a pharmaceutical composition comprising a compound of the invention, and at least one additional active agent(s) selected from antihyperlipidemic agents, plasma HDL-raising agents, antihypercholesterolemic agents, cholesterol biosynthesis inhibitors, HMG CoA reductase inhibitors, acyl-coenzyme A:cholesterol acytransferase (ACAT) inhibitors, probucol, raloxifene, nicotinic acid, niacinamide, cholesterol absorption inhibitors, bile acid sequestrants, low density lipoprotein receptor inducers, clofibrate, fenofibrate, benzofibrate, cipofibrate, gemfibrizol, vitamin $B_6$, vitamin $B_{12}$, vitamin C, vitamin E, β-blockers, anti-diabetes agents, sulfonylureas, biguanides, thiazolidinediones; activators of PPARα, PPARβ and PPARγ, dehydroepiandrosterone, antiglucocorticoids, TNFα inhibitors, α-glucosidase inhibitors, pramlintide, amylin, insulin, angiotensin II antagonists, angiotensin converting enzyme inhibitors, platelet aggregation inhibitors, fibrinogen receptor antagonists, LXR α agonists, partial agonists or antagonists, LXR β agonists, partial agonists or antagonists, phenylpropanolamine, phentermine, diethylpropion, mazindol, fenfluramine, dexfenfluramine, phentiramine, $β_3$ adrenoceptor agonist agents, sibutramine, gastrointestinal lipase inhibitors, neuropeptide Y, enterostatin, cholecytokinin, bombesin, amylin, histamine $H_3$ receptor agonists or antagonists, dopamine $D_2$ receptor agonists or antagonists, melanocyte stimulating hormone, corticotrophin releasing factor, leptin, galanin or gamma amino butyric acid (GABA), aspirin or fibric acid derivatives, simultaneously with, prior to, or after administration of the compound of the invention.

Another embodiment of the invention is a method which comprises administering at least one additional active agent selected from antihyperlipidemic agents, plasma HDL-raising agents, antihypercholesterolemic agents, cholesterol biosynthesis inhibitors, HMG CoA reductase inhibitors, acyl-coenzyme A: cholesterol acytransferase (ACAT) inhibitors, probucol, raloxifene, nicotinic acid, niacinamide, cholesterol absorption inhibitors, bile acid sequestrants, low density lipoprotein receptor inducers, clofibrate, fenofibrate, benzofibrate, cipofibrate, gemfibrizol, vitamin $B_6$, vitamin $B_{12}$, antioxidant vitamins, β-blockers, anti-diabetes agents, angiotensin II antagonists, angiotensin converting enzyme inhibitors, platelet aggregation inhibitors, fibrinogen receptor antagonists, aspirin, LXR α agonists, partial agonists or antagonists, LXR β agonists, partial agonists or antagonists, or fibric acid derivatives, simultaneously with, prior to, or after administration of the compound of the invention.

Another embodiment of the invention is a method which comprises administering at least one additional active agent selected from sulfonylureas, biguanides, thiazolidinediones; activators of PPARα, PPARβ, and PPARγ; agonists, LXR α agonists, partial agonists or antagonists, LXR β agonists, partial agonists or antagonists, dehydroepiandrosterone; antiglucocorticoids; TNF α inhibitors; α-glucosidase inhibitors, pramlintide, amylin, insulin or insulin, simultaneously with, prior to, or after administration of the compound of the invention.

Another embodiment of the invention is a method administering at least one additional active agent selected from phenylpropanolamine, phentermine, diethylpropion, mazindol, fenfluramine, dexfenfluramine, phentiramine, $β_3$ adrenoceptor agonist agents, sibutramine, gastrointestinal lipase inhibitors, LXR α agonists, partial agonists or antagonists, LXR β agonists, partial agonists or antagonists, neuropeptide Y, enterostatin, cholecytokinin, bombesin, amylin, histamine $H_3$ receptor agonists or antagonists, dopamine $D_2$ receptor agonists or antagonists, melanocyte stimulating hormone, corticotrophin releasing factor, leptins, galanin or gamma amino butyric acid (GABA) simultaneously with, prior to, or after administration of the compound of the invention.

Another embodiment of the invention is a method of preventing or reducing the risk of occurrence of, or complications arising from, hyperlipidemia, hypercholesterolemia, hypertriglyceridemia, dyslipidemia, lipodystrophy, atherosclerosis, atherosclerotic disease, atherosclerotic disease events, atherosclerotic cardiovascular disease, Syndrome X diabetes mellitus, type II diabetes, insulin insensitivity, hyperglycemia, cholestasis and obesity in a subject, comprising administering a prophylactically effective amount of a compound of the invention.

Another embodiment of the invention is a method of reducing plasma cholesterol levels, in a subject in need thereof, comprising administering an effective amount of a compound of the invention.

Another embodiment of the invention is a method of reducing plasma triglyceride levels in a subject in need thereof, comprising administering an effective amount of a compound of the invention. Another embodiment of the invention is a method of treating, preventing, or ameliorating one or more symptoms of a disease or disorder which is affected by abnormal cholesterol, triglyceride, or bile acid levels, comprising administering to a subject in need thereof an effective amount of a compound of the invention. Another embodiment of the invention is a method of modulating cholesterol metabolism, catabolism; synthesis, absorption, re-absorption, secretion or excretion in a mammal, comprising administering an effective amount of a compound of the invention.

Another embodiment of the invention is a method of modulating triglyceride metabolism, catabolism, synthesis, absorption, re-absorption, secretion or excretion in a mammal comprising administering an effective amount of a compound of the invention.

Another embodiment of the invention is a method of modulating bile acid metabolism, catabolism, synthesis, absorption, re-absorption, secretion, excretion or bile acid pool composition in a mammal comprising administering an effective amount of a compound of the invention.

Another embodiment of the invention is a method of treating, preventing, or ameliorating one or more symptoms of a disease or disorder in which nuclear receptor activity is implicated, comprising administering to a subject in need thereof an effective amount of a compound of the invention. In another embodiment, the disease or disorder is selected from hyperlipidemia, hypercholesterolemia, hypertriglyceridemia, dyslipidemia, lipodystrophy, atherosclerosis, atherosclerotic disease, atherosclerotic disease events, atherosclerotic cardiovascular disease, Syndrome X, diabetes mellitus, type II diabetes, insulin insensitivity, hyperglycemia, cholestasis and obesity.

In another embodiment, the disease or disorder is selected from the group consisting of hyperlipidemia, hypertriglyceridemia, hypercholesterolemia and dyslipidemia. In another embodiment, the disease or disorder is selected from the group consisting of atherosclerosis, atherosclerotic disease, atherosclerotic disease events and atherosclerotic cardiovascular disease.

In another embodiment, the disease or disorder is selected from the group consisting of Syndrome X, diabetes mellitus, type II diabetes, insulin insensitivity and hyperglycemia.

In another embodiment, the disease or disorder is hyperlipidemia. In another embodiment, the disease or disorder is hypertriglyceridemia. In another embodiment, the disease or disorder is hypercholesterolemia. In another embodiment, the disease or disorder is obesity. In another embodiment, the disease or disorder is cholestasis.

In another embodiment of the invention, the compound of the invention is a farnesoid X receptor agonist, partial agonist, partial antagonist or antagonist. Another embodiment of the invention is a method of treating, preventing, or ameliorating one or more symptoms of a disease or disorder in which farnesoid X receptor activity is implicated, comprising administering to a subject in need thereof an effective amount of a compound of the invention. Another embodiment of the invention is a method which further comprises administering at least one additional active agent selected from antihyperlipidemic agents, plasma HDL-raising agents, antihypercholesterolemic agents, cholesterol biosynthesis inhibitors, HMG CoA reductase inhibitors, acyl-coenzyme A:cholesterol acytransferase (ACAT) inhibitors, probucol, raloxifene, nicotinic acid, niacinamide, cholesterol absorption inhibitors, bile acid sequestrants, low density lipoprotein receptor inducers, clofibrate, fenofibrate, benzofibrate, cipofibrate, gemfibrizol, vitamin $B_6$, vitamin $B_{12}$, vitamin C, vitamin E, β-blockers, anti-diabetes agents, sulfonylureas, biguanides, thiazolidinediones; activators of PPARα, PPARβ and PPARγ, dehydroepiandrosterone, antiglucocorticoids, TNFα inhibitors, α-glucosidase inhibitors, pramlintide, amylin, insulin, angiotensin II antagonists, angiotensin converting enzyme inhibitors, platelet aggregation inhibitors, fibrinogen receptor antagonists, LXR α agonists, partial agonists or antagonists, LXR β agonists, partial agonists or antagonists, phenylpropanolamine, phentermine, diethylpropion, mazindol, fenfluramine, dexfenfluramine, phentiramine, $β_3$ adrenoceptor agonist agents, sibutramine, gastrointestinal lipase inhibitors, neuropeptide Y, enterostatin, cholecytokinin, bombesin, amylin, histamine $H_3$ receptor agonists or antagonists, dopamine $D_2$ receptor agonists or antagonists, melanocyte stimulating hormone, corticotrophin releasing factor, leptin, galanin or gamma amino butyric acid (GABA), aspirin or fibric acid derivatives, simultaneously with, prior to, or after administration of the compound of the invention. Another embodiment of the invention is a method which further comprises administering at least one additional active agent selected from antihyperlipidemic agents, plasma HDL-raising agents, antihypercholesterolemic agents, cholesterol biosynthesis inhibitors, HMG CoA reductase inhibitors, acyl-coenzyme A:cholesterol acytransferase (ACAT) inhibitors, probucol, raloxifene, nicotinic acid, niacinamide, cholesterol absorption inhibitors, bile acid sequestrants, low density lipoprotein receptor inducers, clofibrate, fenofibrate, benzofibrate, cipofibrate, gemfibrizol, vitamin $B_6$, vitamin $B_{12}$, antioxidant vitamins, β-blockers, anti-diabetes agents, angiotensin II antagonists, angiotensin converting enzyme inhibitors, platelet aggregation inhibitors, fibrinogen receptor antagonists, aspirin, LXR α agonists, partial agonists or antagonists, LXR β agonists, partial agonists or antagonists, or fibric acid derivatives, simultaneously with, prior to, or after administration of the compound of the invention.

Another embodiment of the invention is a method which further comprises administering at least one additional active agent selected from sulfonylureas, biguanides, thiazolidinediones; activators of PPARα, PPARβ, and PPARγ; agonists, LXR α agonists, partial agonists or antagonists, LXR β agonists, partial agonists or antagonists, dehydroepiandrosterone; antiglucocorticoids; TNF α inhibitors; α-glucosidase inhibitors, pramlintide, amylin, insulin or insulin, simultaneously with, prior to, or after administration of the compound of the invention.

Another embodiment of the invention is a method which further comprises administering at least one additional active agent selected from phenylpropanolamine, phentermine, diethylpropion, mazindol, fenfluramine, dexfenfluramine, phentiramine, $β_3$ adrenoceptor agonist agents, sibutramine, gastrointestinal lipase inhibitors, LXR α agonists, partial agonists or antagonists, LXR β agonists, partial agonists or antagonists, neuropeptide Y, enterostatin, cholecytokinin, bombesin, amylin, histamine $H_3$ receptor agonists or antagonists, dopamine $D_2$ receptor agonists or antagonists, melanocyte stimulating hormone, corticotrophin releasing factor, leptins, galanin or gamma amino butyric acid (GABA) simultaneously with, prior to, or after administration of the compound of the invention.

Another embodiment of the invention is a method of preventing or reducing the risk of occurrence of, or complications arising from, hyperlipidemia, hypercholesterolemia, hypertriglyceridemia, dyslipidemia, lipodystrophy, atherosclerosis, atherosclerotic disease, atherosclerotic disease events, atherosclerotic cardiovascular disease, Syndrome X diabetes mellitus, type II diabetes, insulin insensitivity, hyperglycemia, cholestasis and obesity in a subject, comprising administering a prophylactically effective amount of a compound of the invention.

Another embodiment of the invention is a method of reducing plasma cholesterol levels, in a subject in need thereof, comprising administering an effective amount of a compound of the invention. Another embodiment of the invention is a method of reducing plasma triglyceride levels in a subject in need thereof, comprising administering an effective amount of a compound of the invention. Another embodiment of the invention is a method of treating, preventing, or ameliorating one or more symptoms of a disease or disorder which is affected by abnormal cholesterol, triglyceride, or bile acid levels, comprising administering to a subject in need thereof an effective amount of a compound of the invention.

Another embodiment of the invention is a method of modulating cholesterol metabolism, catabolism, synthesis, absorption, re-absorption, secretion or excretion in a mammal, comprising administering an effective amount of a compound of the invention.

Another embodiment of the invention is a method of modulating triglyceride metabolism, catabolism, synthesis, absorption, re-absorption, secretion or excretion in a mammal comprising administering an effective amount of a compound of the invention.

Another embodiment of the invention is a method of modulating bile acid metabolism, catabolism, synthesis, absorption, re-absorption, secretion, excretion or bile acid pool composition in a mammal comprising administering an effective amount of a compound of the invention.

C. Preparation of the Compounds of the Invention

Starting materials in the synthesis examples provided herein are either available from commercial sources or via literature procedures (e.g., March *Advanced Organic Chemistry: Reactions, Mechanisms, and Structure,* (1992) 4th Ed.; Wiley Interscience, New York). All commercially available compounds were used without further purification unless otherwise indicated. $CDCl_3$ (99.8% D, Cambridge Isotope Laboratories) was used in all experiments as indicated. Proton ($^1$H) nuclear magnetic resonance (NMR) spectra were recorded on a Bruker Avance 400 MHz NMR spectrometer. Significant peaks are tabulated and typically include: number of protons, and multiplicity (s, singlet; d, double; t, triplet; q, quartet; m, multiplet; br s, broad singlet). Chemical shifts are reported as parts per million (δ) relative to tetramethylsilane. Low resolution mass spectra (MS) were obtained as electrospray ionization (ESI) mass spectra, which were recorded on a Perkin-Elmer SCIEX HPLC/MS instrument using reverse-phase conditions (acetonitrile/water, 0.05% trifluoroacetic acid). Flash chromatography was performed using Merck Silica Gel 60 (230-400 mesh) following standard protocol (Still et al. (1978) *J. Org. Chem.* 43:2923).

It is understood that in the following description, combinations of substituents and/or variables of the depicted formulae are permissible only if such contributions result in stable compounds.

It will also be appreciated by those skilled in the art that in the process described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (e.g., t-butyidimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R (where R is alkyl, aryl or aralkyl), p-methoxybenzyl, trityl and the like. Suitable protecting groups for carboxylic acid include alkyl, aryl or aralkyl esters.

Protecting groups may be added or removed in accordance with standard techniques, which are well-known to those skilled in the art and as described herein. The use of protecting groups is described in detail in Green, T. W. and P. G. M. Wutz, *Protective Groups in Organic Synthesis* (1991), 2nd Ed., Wiley-Interscience.

In the following Schemes, unless otherwise noted, the various R substituents and the symbols X, Y and Z are as defined above in the Summary of the Invention, and A is halo. One of ordinary skill in the art could easily ascertain which choices for each substituent are possible for the reaction conditions of each Scheme. Moreover, the substituents are selected from components as indicated in the specification heretofore, and may be attached to starting materials, intermediates, and/or final products according to schemes known to those of ordinary skill in the art.

Also it will be apparent that many of the products could exist as one or more isomers, that is E/Z isomers, enantiomers and/or diastereomers.

Provisional application No.60/383,574, filed on May 24, 2002, and its corresponding non-provisional application, Ser. No. 10/447,302, filed May 27, 2003, which describe in additional detail certain background information, procedures, compounds and/or compositions, are hereby incorporated by reference in their entirety.

Scheme 1 depicts the general synthesis of compounds of formula I. In general, heteroar-3-yl-2-ethylamines (1) are condensed with haloketones (2) (or haloaldehydes) and undergo subsequent rearrangement to give azepines (3), which then can react with electrophiles to afford products (4) of formula I. In particular, heteroar-3-yl-2-ethylamines (1) (where $R^4$-$R^7$ are described above in the Summary of the Invention) can consist of optionally substituted imidazol-4-ylethylamines ($X=NR^9$, $Y=CR^{30}$, $Z=N$), optionally substituted pyrrole-3-yl-2-ethylamines ($X=NR^9$, $Y=CR^{30}$, $Z=CR^{31}$) or thiophene-3-yl-2-ethylamines ($X=S$, $Y=CR^{30}$, $Z=CR^{31}$). By example, a haloketone (2) can be chloro- or bromopyruvate ($R^1=CO_2R$ and $R^2=H$) and the electrophiles can be acyl or sulfonyl chlorides, chloroformates, isocyanates or isothiocyanates ($R^3=COR$, $SO_2R$, $CO_2R$, CONRR' and CSNRR', respectively).

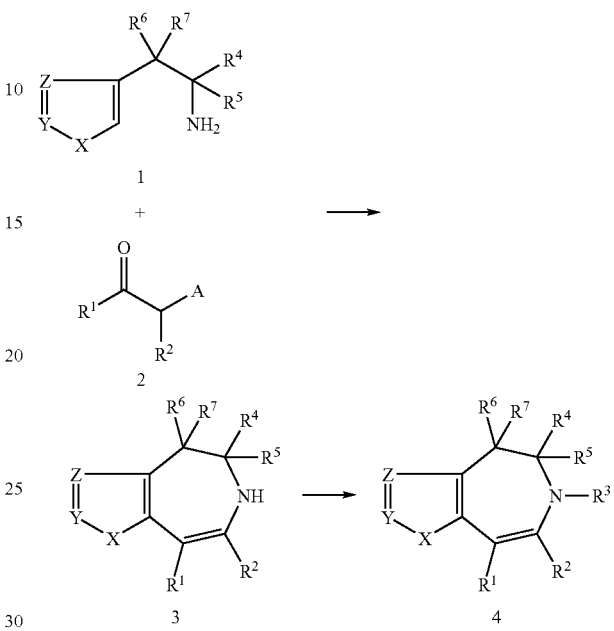

SCHEME 1

As depicted in Scheme 2, commercially unavailable ethylamines (1a) can be prepared from commercially available material such as compounds 5-10. There are a variety of approaches to the syntheses of compounds 5 (Katritzky, *Comprehensive Heterocyclic Chemistry*, Elsevier Science, 1997; Joule et al. *Heterocyclic Chemistry*, 3$^{rd}$ Ed., Chapman & Hall, 1995). Aldehydes (6) can be prepared from compounds 5 via formylation, e.g., with dichloromethyl methyl ether and aluminum chloride (Carter et al. *J. Am. Chem. Soc.* 1987, 109, 2711-2717). Reduction of aldehydes (6) with sodium borohydride can afford alcohols (7) (Ladduwahetty et al. *J. Med. Chem.* 1996, 39, 2907-2914). Alcohols (7) can be transformed into halides (8) (Turner et al. *J. Am. Chem. Soc.* 1949, 71, 2801; Michailow et al. *Zh. Obshch. Khim.* 1957, 27, 726). Substitution of halides (8) with cyanide can afford acetonitriles (9) (Potvin et al. *Tetrahedron Asymmetry*, 1996, 10, 2821-24; Madronero et al. *Eur. J. Med. Chem. Chim. Ther.* 1974, 9, 445-448). Optional alkylation of 9 can be followed by reduction, e.g. with lithium aluminum hydride, to give heteroar-3-yl-2-ethylamines (1a).

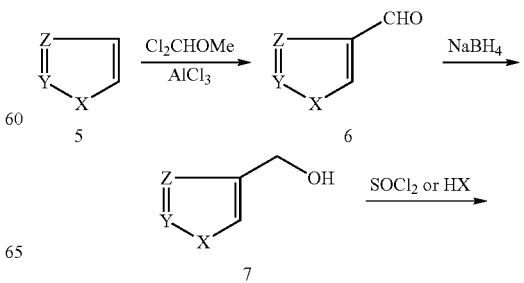

SCHEME 2

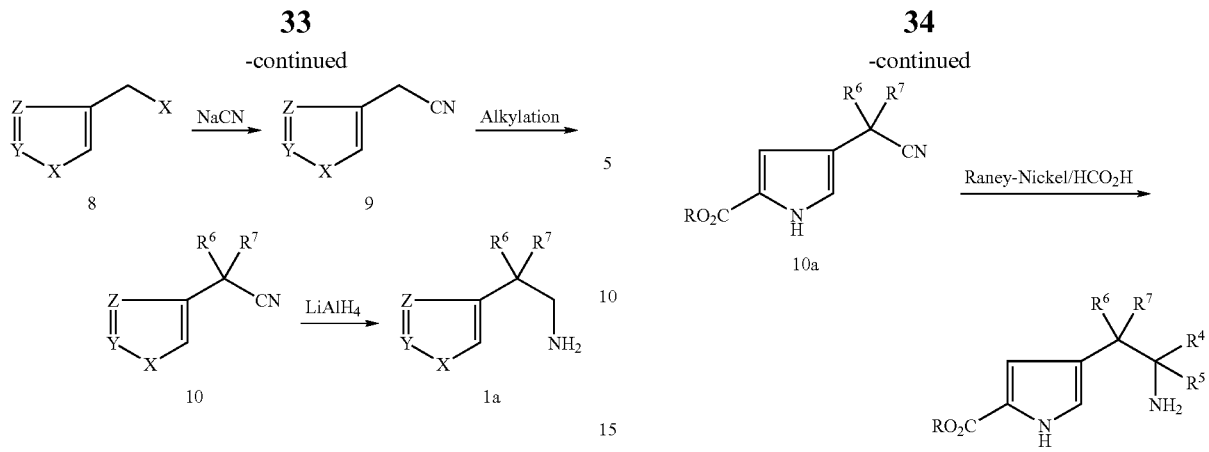

A more specific example of a compound of structure (1a) (3-(2-minoethyl)pyrrole-2-carboxylate) can also be synthesized via dimethylaminomethylpyrrole intermediate 7a as shown in Scheme 2a. Aldehydes (6a) can be prepared from compounds 5 via formylation with dichloromethyl methyl ether and aluminum chloride. Reductive amination of aldehydes (6a) with dimethylamine/sodium borohydride can afford dimethylamines (7a) (Ladduwahetty et al. J. Med. Chem. 1996, 39, 2907-2914). Dimethylamines (7a) can be transformed into a quaternary ammonium salt (8a) Substitution of the trimethylammonium salt of (8a) with cyanide can afford acetonitriles (9a). Protection of nitrogen atom of 9a with a Boc group can be followed with optional alkylation and deprotection to afford 10a. Reduction of nitrile 10a with Raney-nickel in formic acid can afford 3-(2-aminoethyl)pyrrole-2-carboxylate (1a).

As depicted in Scheme 3, ethylamines (1b) can be prepared from nitroolefins (11). Condensation of nitroalkanes with aldehydes (6) in the presence of a base affords nitroolefins (11) (Hamdan et al. *Synth. Commun.* 1985, 15, 71-74; Arnold et al. *J. Heterocycl. Chem.* 1990, 27,1169-1171), which can be reduced with lithium aluminum hydride to give ethylamines (1b).

SCHEME 2A

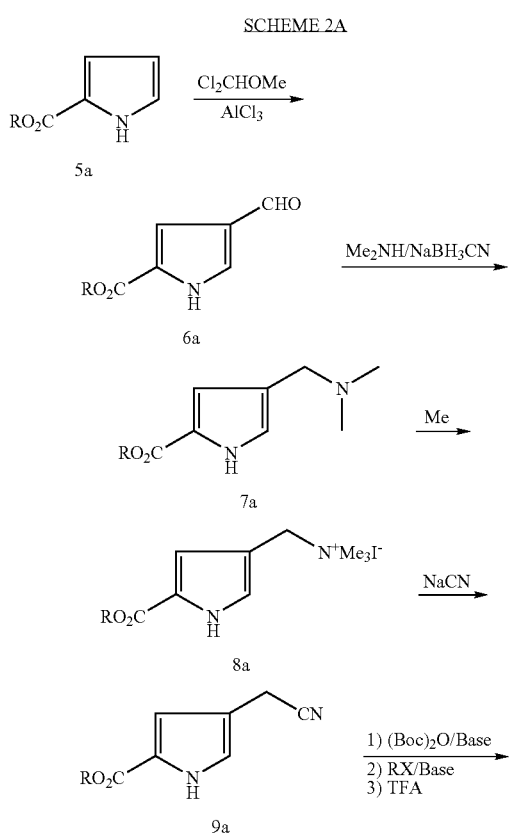

SCHEME 3

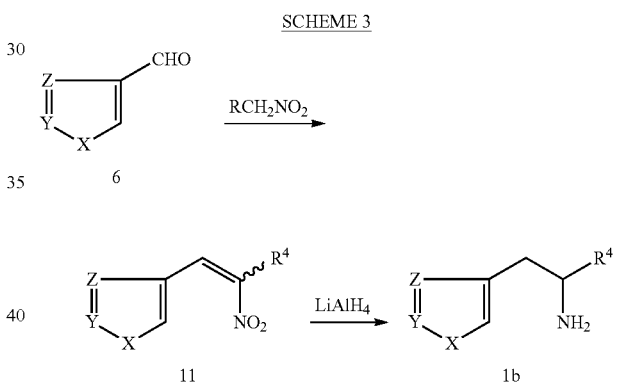

As depicted in Scheme 4, the formation of the azepine ring can be achieved by a Pictet-Spengler reaction and a subsequent rearrangement. Amines (1) (with HCl added in situ) or their hydrochloride salts can react with 3-halopyruvates (2a) in the corresponding alcohols under reflux to afford piperidine derivatives (12), which are then heated under basic conditions, i.e. with TEA or in pyridine, to give azepine compounds (13). Subsequent treatment of 13 with electrophiles, i.e. acyl or sulfonyl chlorides, isocyanates and chloroformates, in the presence of a base, e.g. TEA, affords final products 14 (Kuehne et al. (1985) *J. Org. Chem.* 50:919-924).

SCHEME 4

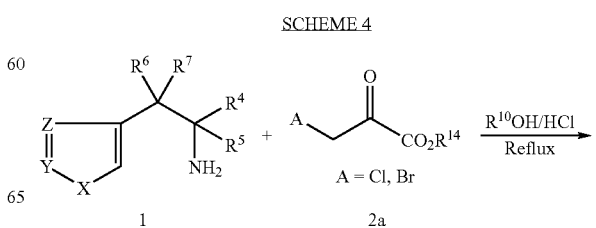

-continued

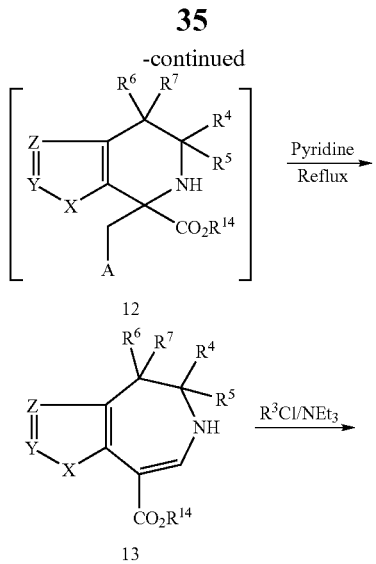

Likewise, other haloketones (2) (e.g. $R^1$=alkyl or aryl) can undergo a similar reaction sequence to afford the corresponding azepines (15), as depicted in Scheme 5.

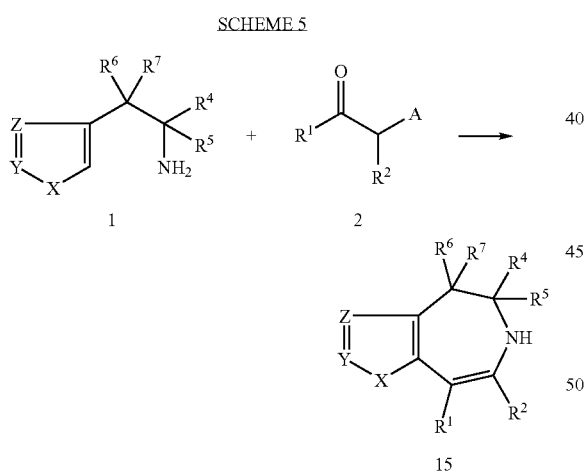

As depicted in Scheme 6, indole benzene ring can be reduced selectively to give a saturated ring. Formation of indoleazepine ring can be achieved by a Pictet-Spengler reaction and a subsequent rearrangement. Thus, for example, tryptamines (1c, X=$NR^9$) can react with a haloketone such as 3-halopyruvates (2a) to afford β-carboline intermediates (16), which are then heated under basic conditions, i.e. with TEA or in pyridine, to give azepines (17) (Kuehne et al. (1985) *J. Org. Chem.* 50:919-924) where $R^8$ is as defined in U.S. non-provisional application, Ser. No. 10/447,302. Subsequent treatment of 17 with electrophiles, i.e. acyl or sulfonyl chlorides, isocyanates and chloroformates, in the presence of a base, e.g. TEA, affords final products 18. In addition, azepino[4,5-b]benzofurans (18, X=O) and azepino[4,5-b]benzothiophenes (18, X=S) can be prepared in a similar manner from the respective heteroar-3-yl-2-ethylamines (1c, X=O or S). The benzene ring of the azepinoindole can be reduced by hydrogenation mediated by Adam's catalyst under 40 psi hydrogen (Boekelheide & Liu, *J. Am. Chem. Soc.* 1952, 74, 4920-4922) to give compound 19, which can be transformed into compound 20, e.g., via oxidation with tert-butyl hypochlorite to reinstall the double bond (Kuehne et al. (1985) *J. Org. Chem.* 50:919-924). When the hydrogenation mediated by Adam's catalyst was carried out at hydrogen atmosphere, compound 18 was selectively reduced to give compound 20.

Scheme 6

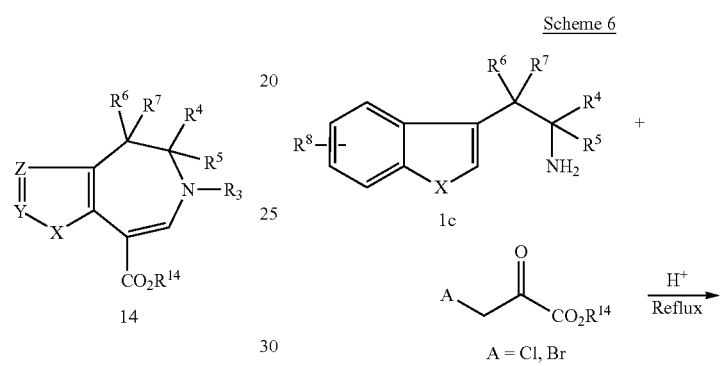

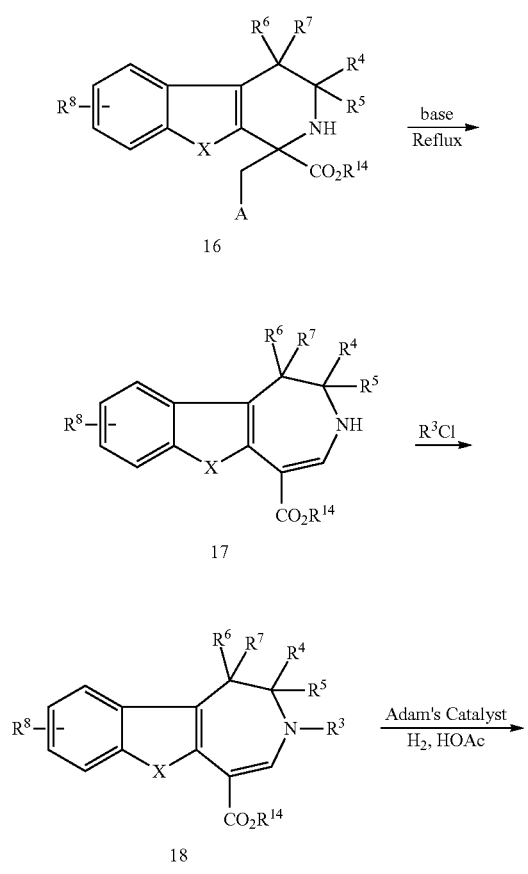

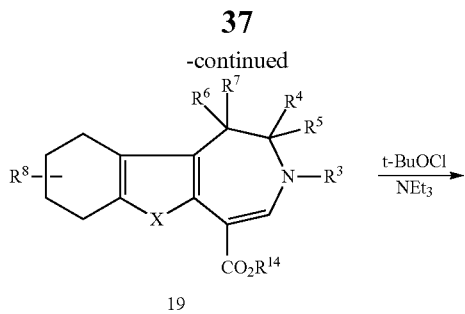

19

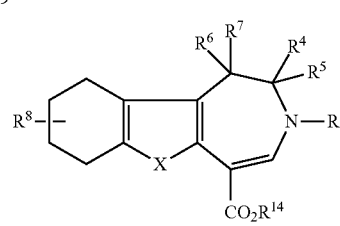

20

X = NR$^9$, O or S(O)$_t$
where t is 0 to 2

The following schemes depict the formation of variously substituted azepino[4,5-b]indoles (18, X=NR$^9$), azepino[4,5-b]benzofurans (18, X=O) and azepino[4,5-b]benzothiophenes (18, X=S), all of which can undergo the reduction step mediated by the Adams catalyst followed by the oxidation step by tert-butyl hypochlorite to reinstall the double bond to yield the corresponding compound 20.

Scheme 7 generally depicts the synthesis of azepino[4,5-b]indoles (22, X=NR$^9$), azepino[4,5-b]benzofurans (22, X=O) and azepino[4,5-b]benzothiophenes (22, X=S) from heteroar-3-yl-2-ethylamines (1c, X=NR$^9$, O or S) and haloketones (2) (e.g. R$^1$ and R$^2$=alkyl or aryl).

SCHEME 7

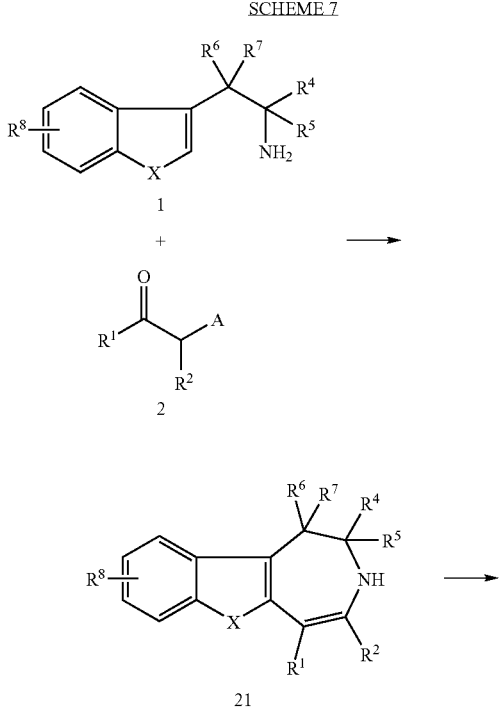

Haloketones (2) or halopyruvates (2a) in Schemes 6 or 7 are either commercially available or may be prepared readily via common literature procedures. In particular, 3-halopyruvates (2a, R$^2$=H) can be prepared by esterification of the corresponding alcohols (R$^1$OH) with 3-halopyruvic chloride (23) (Teague, et al, *Bioorg. & Med. Chem. Lett.* 1995, 5, 2341-2346) as depicted in Scheme 8.

SCHEME 8

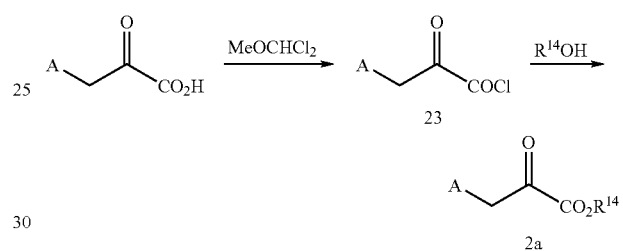

A = Cl or Br

As depicted in Scheme 9, higher 3-halopyruvates (2b) (e.g. R$^2$=alkyl) can be synthesized via oxidative bromination of α-hydroxyesters (24) (*Heterocycles* 1991, 32, 693). While the non-hydrogen R$^2$ substituent can be incorporated into the final azepine products (22), the following Schemes will feature examples that have been simplified by omission of R$^2$.

SCHEME 9

Some substituted tryptamines (28, X=NR$^9$) are commercially available, though many can be prepared from indoles (25, X=NR$^9$) as depicted in Scheme 10. For example, indoles (25) can be formylated to give aldehydes (26, X=NR$^9$) (Mor et al. *J. Med. Chem.* 1998, 41, 3831-3844). These 3-formylindoles (26) can undergo a Henry reaction (Rosini *Comp. Org. Syn.* 1991, 2, 321-340) with 1-nitroalkanes to afford nitroalkenes (27, X=NR$^9$), which can be reduced (i.e., catalytic hydrogenation or lithium aluminum hydride) and then treated with HCl to yield tryptamine hydrochlorides (28). Likewise, other substituted heteroar-3-yl-2-ethylamines (28, X=O or S) can be synthesized from their corresponding heterocycle (25), i.e. benzofurans and benzothiophenes. A variety of indoles also can be prepared via Fischer indole synthesis (Smith & March, *March's Advanced Organic Chemistry*, 5$^{th}$ Ed., John Wiley and Sons:NY, 2001, pp1453-24).

SCHEME 10

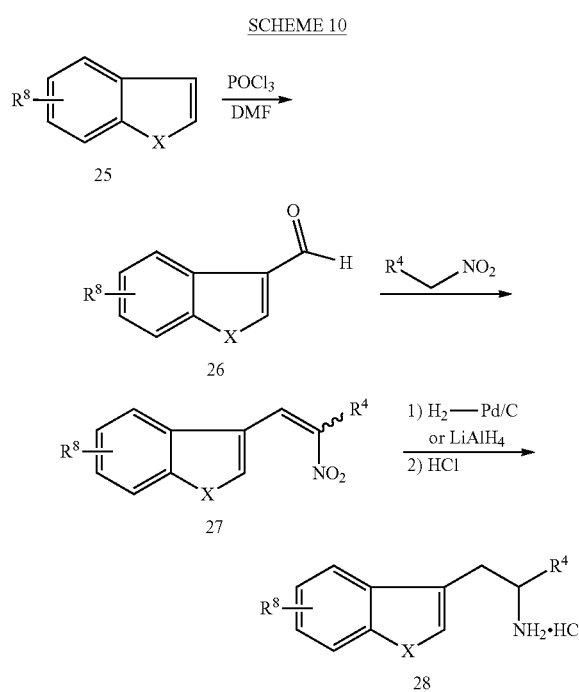

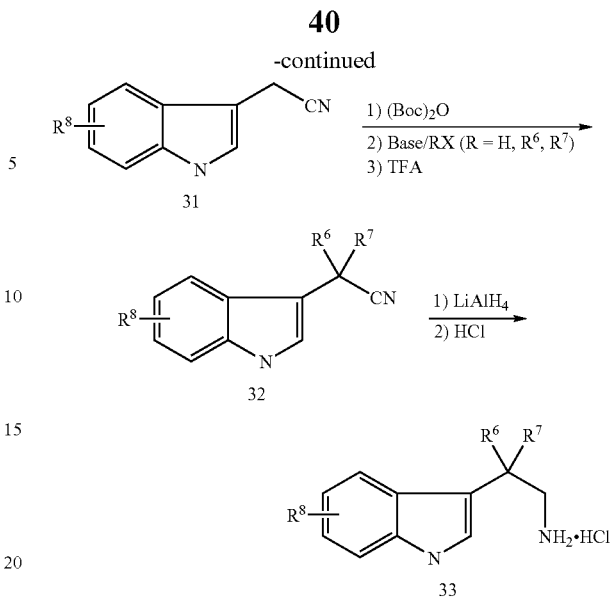

As depicted in Scheme 11, other substituted tryptamines (33) also can be prepared. Protection of 3-indolylacetonitriles (31), for example, with Boc (tert-butoxycarbonyl) followed by mono- or dialkylation, and then deprotection can yield substituted 3-indolylacetonitriles (32). Reduction of 32, e.g. with lithium aluminum hydride, followed by treatment with HCl affords tryptamine hydrochlorides 33. Thus, for example, monoalkyl species (32, R=H, $R^6$) can be prepared by addition of 1 equiv of alkyl halide. Gem-dialkyl species (32, R=$R^6$=$R^7$) can be prepared from 2 equiv of alkyl halide and hetero-dialkyl species (32, R=$R^6$,$R^7$) can be prepared upon sequential addition of 1 equiv each of two alkyl halides. Intermediates (31) can be prepared readily from gramines (30), which are either commercially available or synthesized from indoles (29) (Brown and Garrison, *J. Chem. Chem. Soc.* 1955, 77, 3839-3842). In general, gramines (30) can be treated with methyl iodide to form a quaternary ammonium salt, which can be displaced with cyanide to give 3-indolylacetonitriles (31). Benzofuran-3-yl and benzo[b]thiophene-3-yl ethylamines (28, X=O or S) can be prepared using similar methods, in which protection and deprotection steps are not required.

SCHEME 11

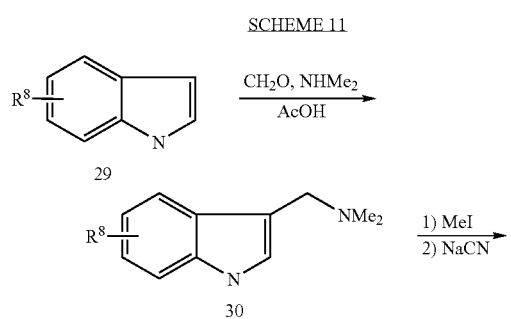

Preparation of spirocyclic analogs (35) of tryptamine also can be achieved as depicted in Scheme 12. For example, intermediate 31 can be protected with benzyl bromide followed by alkylation with an alkyl dihalide, e.g. 1,4-dibromobutane, to afford the corresponding intermediate (34, n=2). Subsequently 34 can be reduced, deprotected (e.g. with sodium metal in liquid ammonia) and treated with HCl to yield the spiro-substituted tryptamine hydrochloride 35.

SCHEME 12

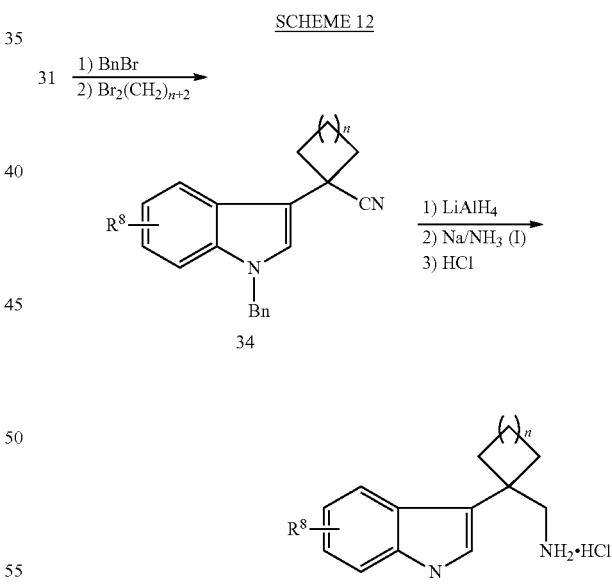

As depicted in Scheme 13, substituted tryptamines (38, X=$NR^9$) can also be prepared by Knoevenagel condensation of 3-indolylacetonitrile (36, X=$NR^9$) with an aldehyde to afford acrylonitriles (37, X=$NR^9$). Subsequent reduction, e.g. Raney nickel, and treatment with HCl can yield tryptamine hydrochlorides (38). Analogous benzofuran-3yl and benzo[b]thiophene-3-yl ethylamines (38, X=O or S) also can be prepared using similar methods.

SCHEME 13

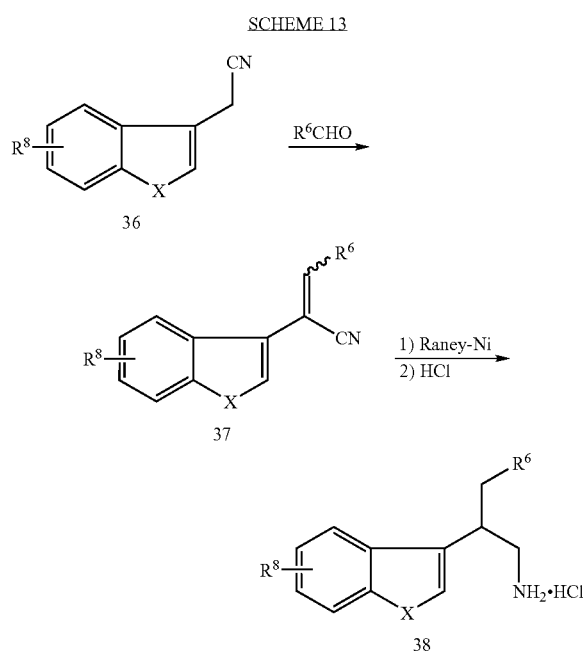

Scheme 14, depicts the synthesis of hexahydroazepino compounds (40) via reduction of azepines (39). For example, tetrahydroazepino[4,5-b]indoles 39 (X=NR⁹) can be reduced with NaBH₃CN to give hexahydroazepino[4,5-b]indoles 40 (Kuehne et al. (1985) *J. Org. Chem.* 50:919-924), which can be treated with an electrophile, e.g. acyl chloride, to afford the corresponding azepine product (41).

SCHEME 14

Scheme 15 depicts the conversion of 5-esters 40 to 5-amides (44) via a multi-step reaction sequence starting with the hexahydroazepino compounds (40). For example, tetrahydroazepino[4,5-b]indoles (17, A=NR⁹) can be reduced with NaBH₃CN to give hexahydroazepino[4,5-b]indoles 40 (Kuehne et al. (1985) *J. Org. Chem.* 50:919-924), which can be treated with various amines to give the corresponding amides (42), which can then be reacted with an electrophile, e.g. an acyl chloride, to afford the corresponding amide (43). Oxidation of 43 with tert-butyl hypochlorite (Kuehne et a. (1985) *J. Org. Chem.* 50:919-924) then can yield the azepine product (44).

SCHEME 15

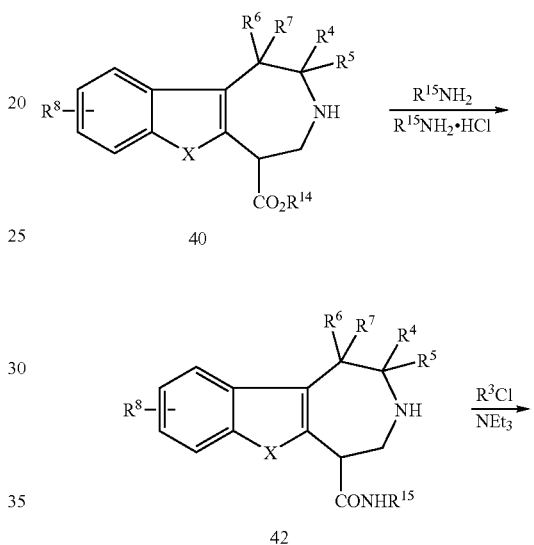

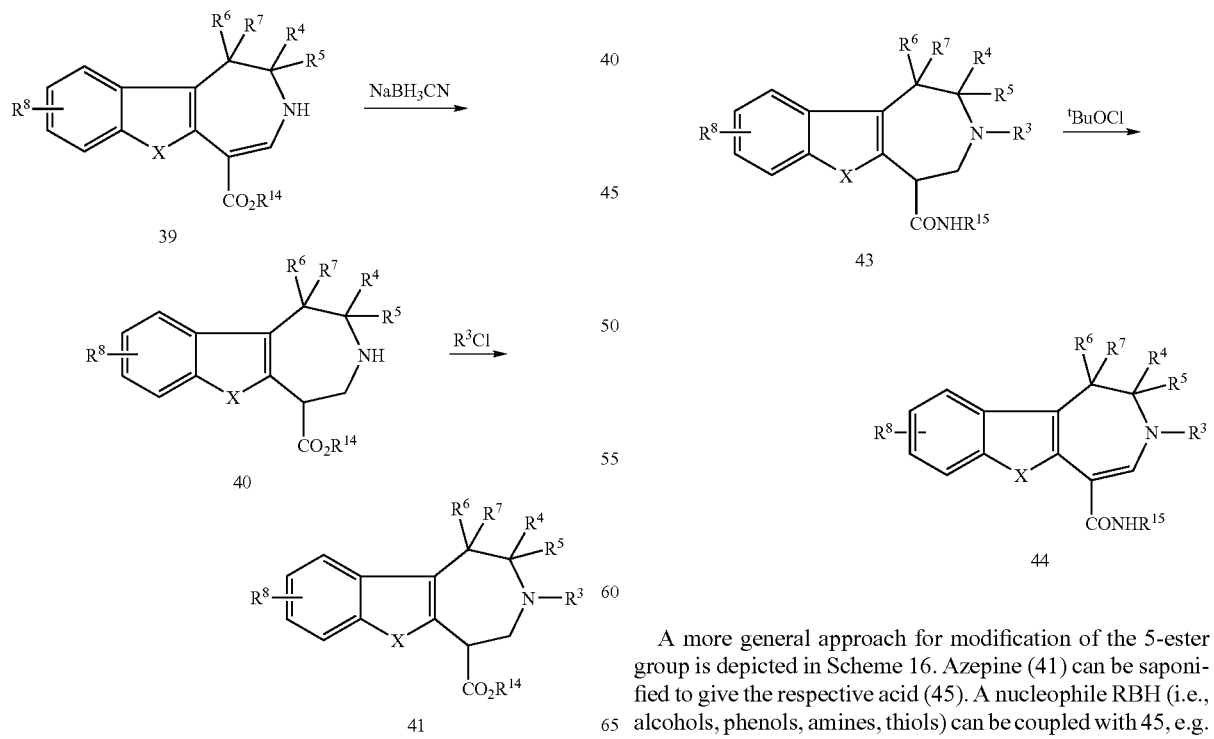

A more general approach for modification of the 5-ester group is depicted in Scheme 16. Azepine (41) can be saponified to give the respective acid (45). A nucleophile RBH (i.e., alcohols, phenols, amines, thiols) can be coupled with 45, e.g. using carbonyldiimidazole (CDI), followed by oxidation with tert-butyl hypochlorite to yield azepine (47).

SCHEME 16

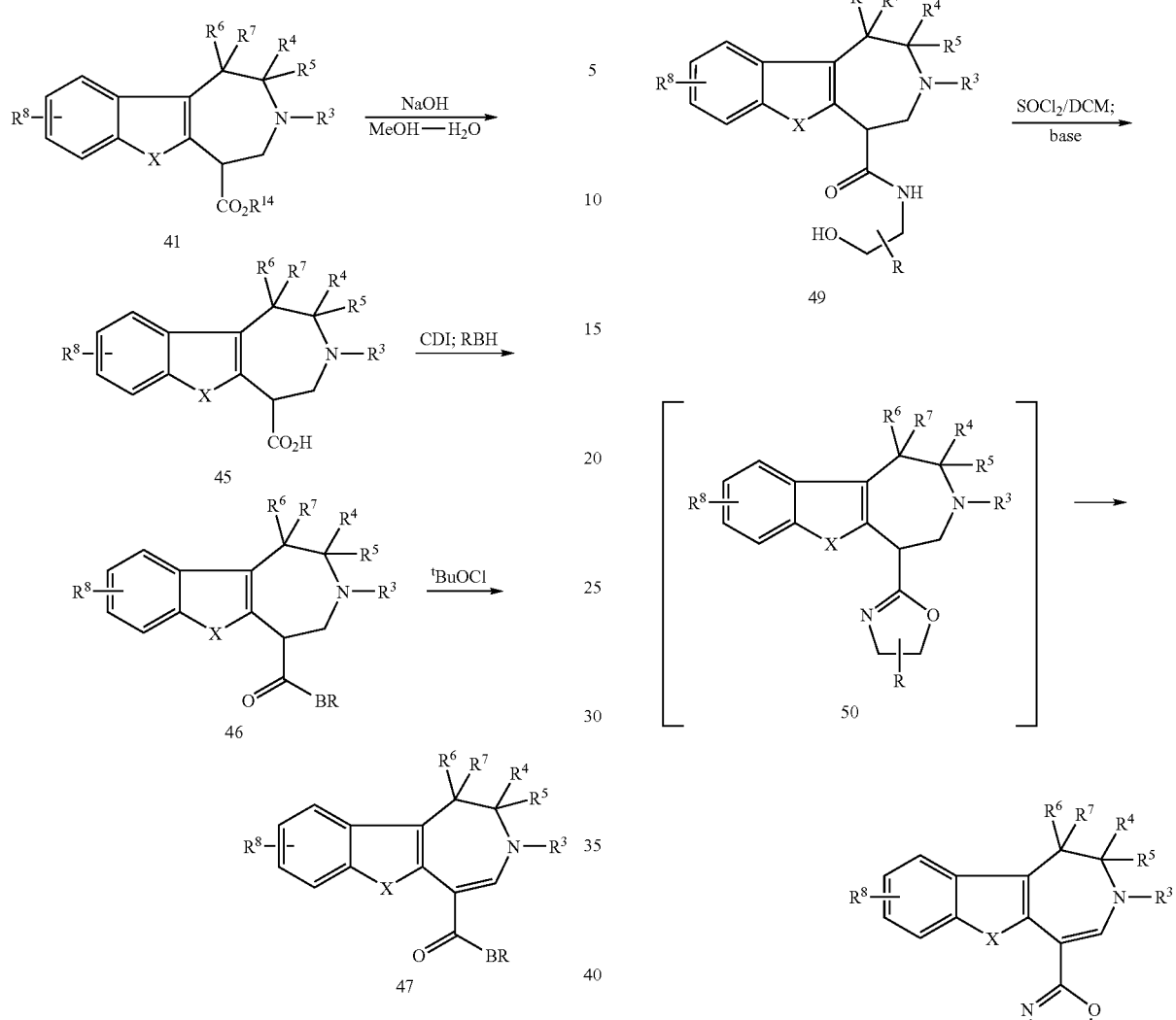

Heterocyclyl groups can be introduced at the 5-position from acid (45). For example, as depicted in Scheme 17 oxazolines are prepared by formation of amides (49) from respective amino alcohols and acid (45). The resulting amides (49) then can be cyclized, e.g. via treatment with thionyl chloride followed by strong base, to afford the corresponding heterocycle (51). Halogenation and subsequent dehydrohalogenation of intermediate (50) (not isolated) can occur under the reaction conditions. Similar reactions can be envisaged for other heterocycles, i.e. imidazolines and thiazolines. Also further oxidation would afford the corresponding heteroaromatic product, e.g. oxazole.

The 5-ester group of 17 can be hydrolyzed to give 5-carboxylic acid (53). However, direct hydrolysis affords 53 in low yield. Accordingly, as depicted in Scheme 18, azepine (17) was transformed into the 3-Boc-protected compound (52, which can be hydrolyzed under the standard basic conditions with Boc elimination to afford acid (53).

SCHEME 17

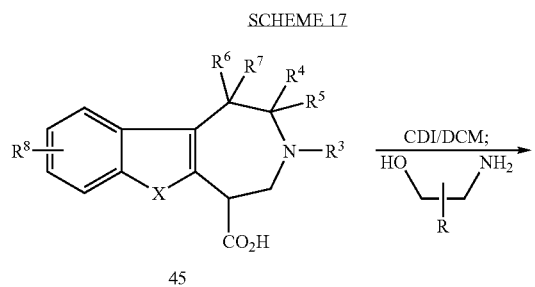

SCHEME 18

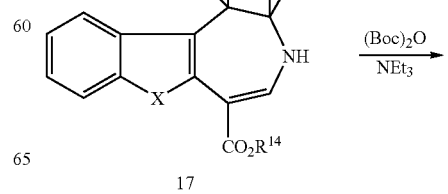

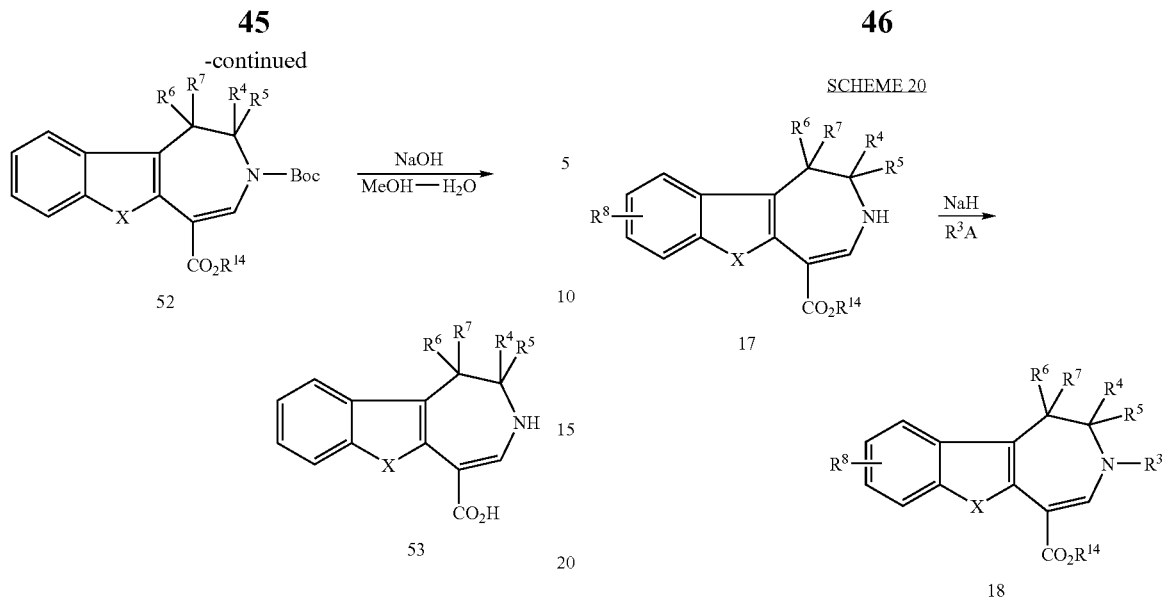

As depicted in Scheme 19, azepine (17) can be treated with Lawesson's reagent (Curphey, et al, *J. Org. Chem.* 2002, 67, 6461-6473) to afford O-alkyl thioester (54) which can be, for example, acylated to yield the azepine product (55).

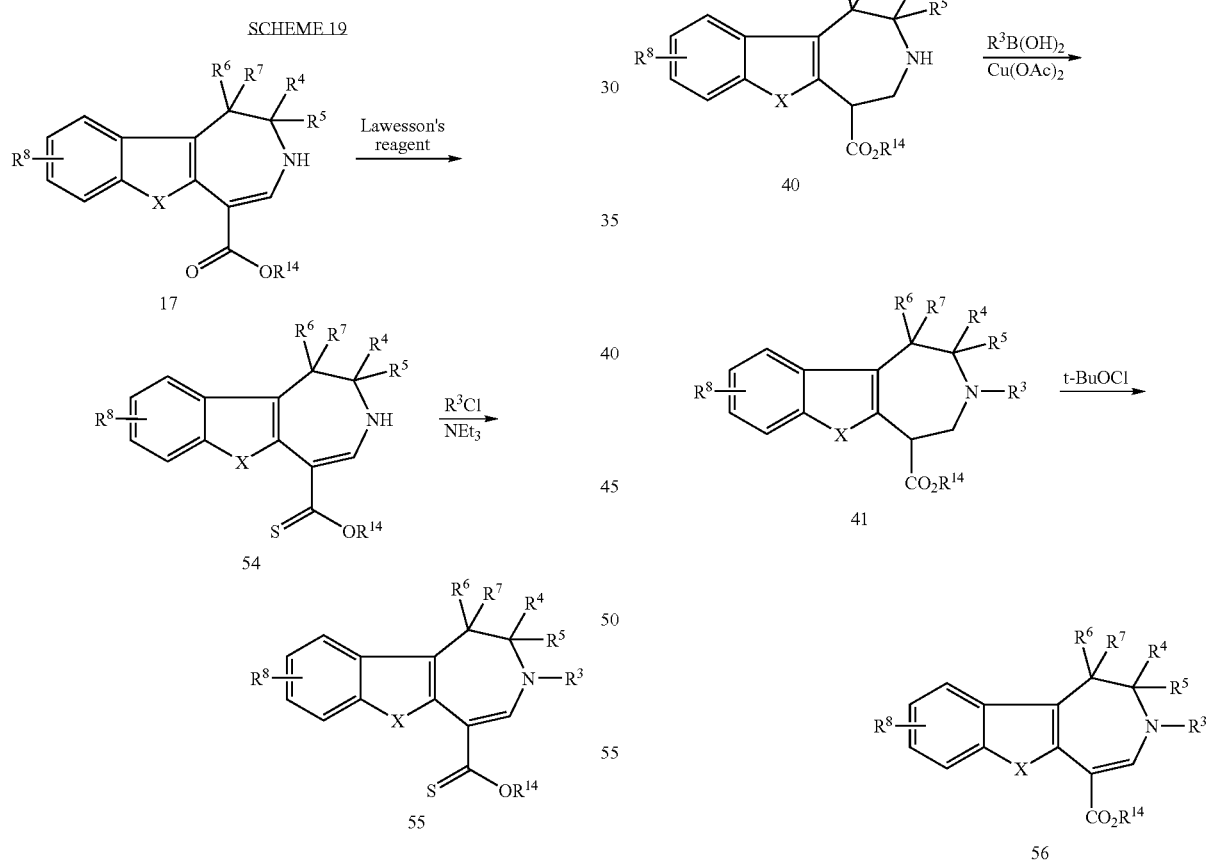

Scheme 20 depicts the incorporation of 3-alkyl/aryl groups. For example, azepine (17) can be treated with a base, e.g. NaH, and then an alkyl halide ($R^3A$) to yield a 3-alkyl azepine (18). An aryl or heteroaryl group ($R^3$) can be introduced via coupling of 41 with boronic acids (Lam, et al, *Tetrahedron Lett.* 2001, 42, 3415-3418), followed by oxidation of intermediate (41) to give the corresponding azepine product (56).

Derivatization of 2-substituted azepines (57) is depicted in Scheme 21. Diester (57) can be partially hydrolyzed to give acid (58), which can be transformed 15 into amides (59), e.g. using CDI. Intermediates (59) can be further substituted upon addition of an electrophile, e.g. acyl chloride, to give the corresponding diamides (60).

SCHEME 21

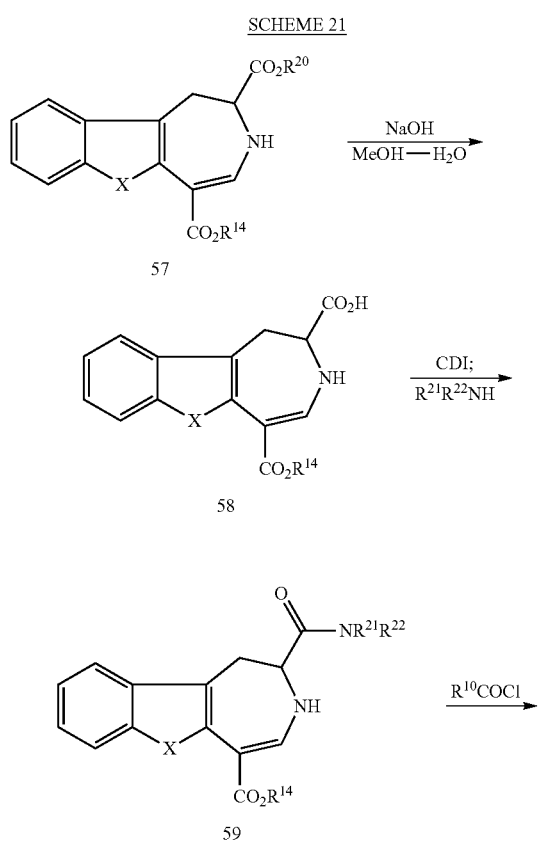

SCHEME 22

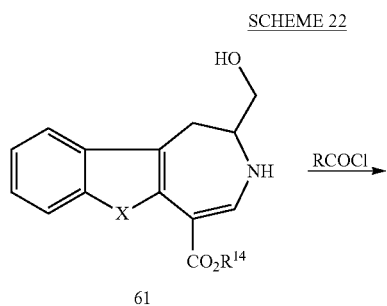

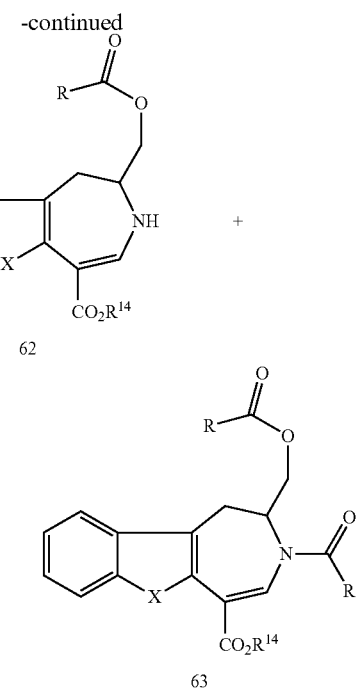

As depicted in Scheme 22, alcohol (61) can be derivatized by addition of an electrophile (i.e. acyl chloride, chloroformate or isocyanate). For example, 61 can be esterified in the presence of base to yield diester (62), though a mixture containing diester-amide (63) may result.

As depicted in Scheme 23, 1-oxoazepines (65) can be employed as key intermediates for introduction of other functional groups. For example, azepine (64) can be oxidized, e.g. with DDQ, to yield 1-oxoazepine 65, which can be reduced to give the corresponding alcohol (66). Treatment of 66 with trifluoromethanesulfonic anhydride followed by addition of nucleophiles RYH (alcohols, thiols, amines, hydroxylamines and hydrazines) can yield the corresponding azepine products (67).

SCHEME 23

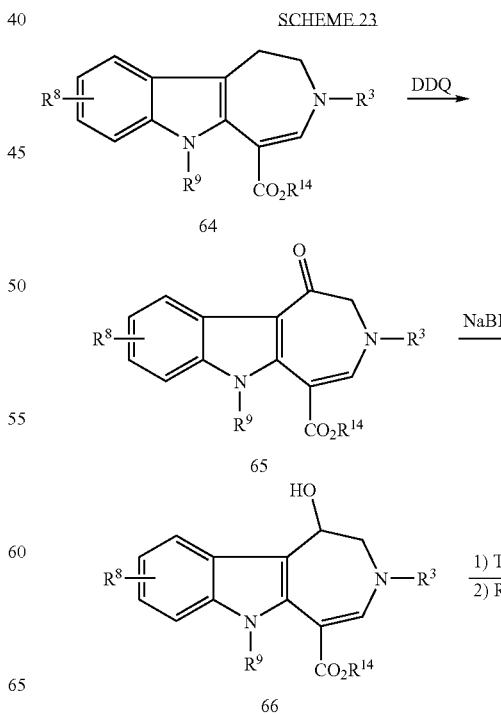

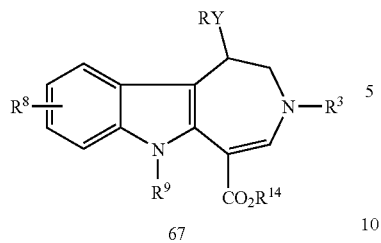

67

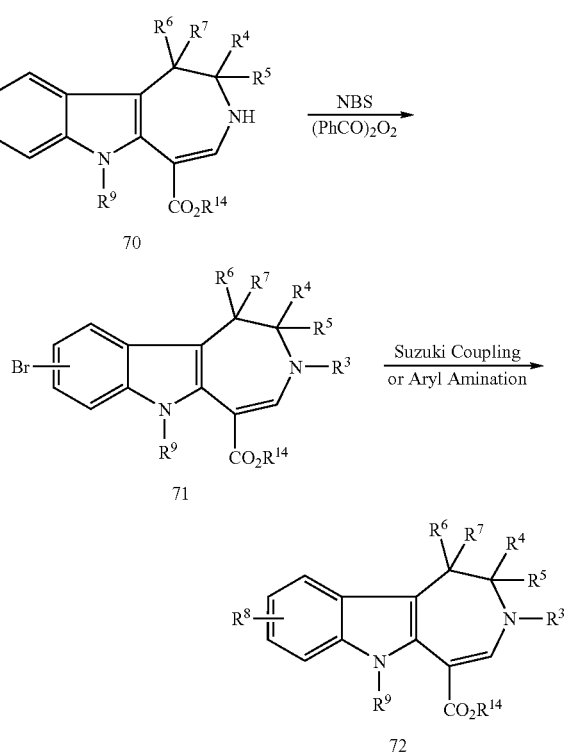

SCHEME 25

70

71

72

Likewise, as depicted in Scheme 24, 1-oxoazepine 65 can be treated with ethylene glycol under acid-catalysis to form cyclic acetal (68). Also 65 can be treated with amines, hydroxylamines and hydrazines to give imines (69, YR=NR$^{15}$), oximes (69, YR=NOR$^{14}$) and hydrazones (69, YR=NNR$^{15}$R$^{16}$), respectively. Furthermore 65 can undergo a Wittig or Horner-Wadsworth-Emmons reaction (Maercker (1965) *Org. React* 14:270-490; Wadsworth, Jr. (1977) *Org. React.* 25:73-253) to yield exocyclic alkylidenes (69, e.g. YR=CRR').

SCHEME 24

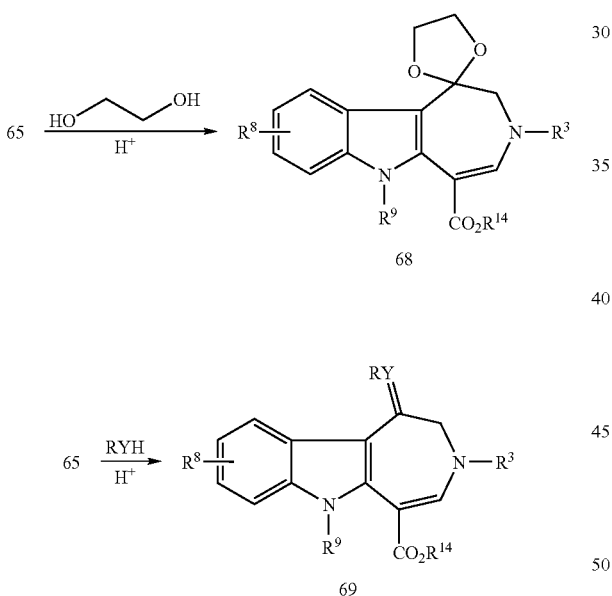

68

69

As depicted in Scheme 26, other transformations of functional groups can be achieved, for example, on the indole ring of azepine (73). Protective groups, such as alkyl and aryl groups, on oxygen, sulfur or nitrogen containing substituents of azepine 73 can be removed under suitable conditions to yield azepine (74). Treatment of 74 with electrophiles, such as carbamoyl chlorides, can yield the corresponding azepines (75), for which the substituent R$^8$ is C(O)NR$^{24}$R$^{25}$ in this representative example.

As depicted in Scheme 25, substituents on the indole ring can be introduced, i.e. via Suzuki cross-coupling and aryl amination reactions from the corresponding aryl bromides (71). Bromo-substituted indoles 71 can be prepared via direct bromination of indoles (70) with NBS or from commercially available tryptamine. These intermediates (71) can be used in Suzuki cross-coupling reactions (Miyaura, et al, *Chem. Rev.* 1995,956, 2457-2483) with boronic acids to afford, for example, aryl-substituted products (72, R$^8$=aryl) and in aryl amination reactions (Wolfe, et at, *J. Org. Chem.* 2000, 65, 1144-1157) to afford amino-substituted products (72, R$^8$=NR$^{28}$R$^{29}$).

SCHEME 27

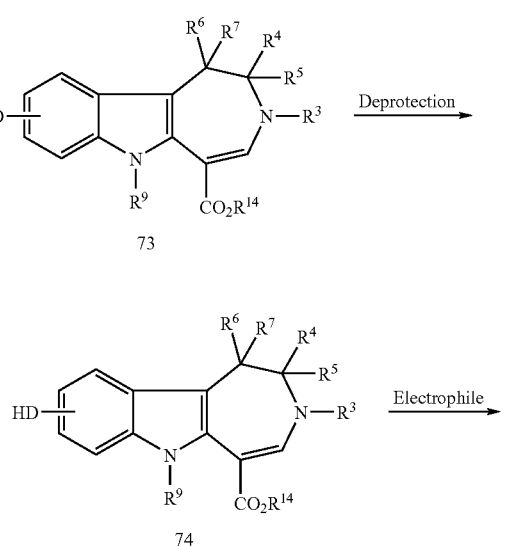

73

74

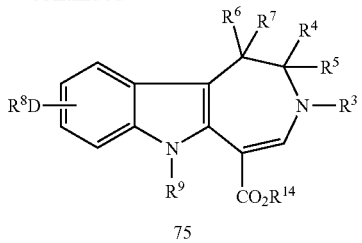

D = NR²⁸ or O
Pg = Protecting group

As depicted in Scheme 27, substituents at 6N-position of azepine (76) can be introduced, for example, via alkylation with a base and alkyl halide, to give the corresponding azepine (77).

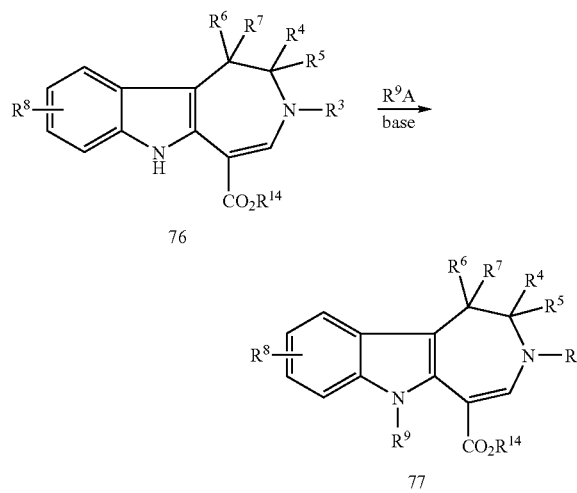

D. Formulation of Pharmaceutical Compositions

The pharmaceutical compositions provided herein contain therapeutically effective amounts of one or more of the nuclear receptor activity modulators provided herein that are useful in the prevention, treatment, or amelioration of one or more of the symptoms of diseases or disorders associated with nuclear receptor activity, including the farnesoid X receptor and/or orphan nuclear receptor activity. Such diseases or disorders include, but are not limited to, hypercholesterolemia, hyperlipoproteinemia, hypertriglyceridemia, lipodystrophy, hyperglycemia, diabetes mellitus, dyslipidemia, atherosclerotic disease events, gallstone disease, acne vulgaris, acneiform skin conditions, type II diabetes, Parkinson's disease, cancer, Alzheimer's disease, inflammation, immunological disorders, lipid disorders, obesity, conditions characterized by a perturbed epidermal barrier function, hyperlipidemia, cholestasis, peripheral occlusive disease, ischemic stroke, conditions of disturbed differentiation or excess proliferation of the epidermis or mucous membrane, and cardiovascular disorders.

Further the pharmaceutical compositions provided herein contain therapeutically effective amounts of one or more of the nuclear receptor activity modulators provided herein that are useful in the prevention, treatment, or amelioration of one or more of the symptoms of diseases or disorders that are not directly associated with a nuclear receptor, but for which a complication of the disease or disorder is treatable with claimed compounds and compositions. By way of example, without limitation, Cystic Fibrosis is not typically associated with a nuclear receptor activity, but can result in cholestasis, which may be treated with the subject compounds and compositions.

The compositions contain one or more compounds provided herein. The compounds are preferably formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. Typically the compounds described above are formulated into pharmaceutical compositions using techniques and procedures well known in the art (see, e.g., Ansel Introduction to Pharmaceutical Dosage Forms, Fourth Edition 1985, 126).

In the compositions, effective concentrations of one or more compounds or pharmaceutically acceptable derivatives is (are) mixed with a suitable pharmaceutical carrier or vehicle. The compounds may be derivatized as the corresponding salts, esters, enol ethers or esters, acids, bases, solvates, hydrates or prodrugs prior to formulation, as described above. The concentrations of the compounds in the compositions are effective for delivery of an amount, upon administration, that treats, prevents, or ameliorates one or more of the symptoms of diseases or disorders associated with nuclear receptor activity or in which nuclear receptor activity is implicated. Such diseases or disorders include, but are not limited to, hypercholesterolemia, hyperlipoproteinemia, hypertriglyceridemia, lipodystrophy, hyperglycemia, diabetes mellitus, dyslipidemia, atherosclerotic disease events, gallstone disease, acne vulgaris, acneiform skin conditions, type II diabetes, Parkinson's disease, cancer, Alzheimer's disease, inflammation, immunological disorders, lipid disorders, obesity, conditions characterized by a perturbed epidermal barrier function, hyperlipidemia, cholestasis, peripheral occlusive disease, ischemic stroke, conditions of disturbed differentiation or excess proliferation of the epidermis or mucous membrane, and cardiovascular disorders.

Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients. Liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The active compound is included in the pharmaceutically acceptable carrier in an amount sufficient to exert a therapeutically useful effect in the absence of undesirable side effects on the patient treated. The therapeutically effective concentration may be determined empirically by testing the compounds using in vitro and in vivo systems described herein and in International Patent Application Publication Nos. 99/27365 and 00/25134 and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders associated with nuclear receptor activity or in which nuclear receptor activity is implicated, as described herein.

Typically a therapeutically effective dosage should produce a serum concentration of active ingredient of from about 0.1 ng/ml to about 50-100 µg/ml. The pharmaceutical compositions typically should provide a dosage of from about 0.001 mg to about 2000 mg of compound per kilogram of body weight per day. Pharmaceutical dosage unit forms are prepared to provide from about 1 mg to about 1000 mg and preferably from about 10 to about 500 mg of the essential active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Pharmaceutically acceptable derivatives include acids, bases, enol ethers and esters, salts, esters, hydrates, solvates and prodrug forms. The derivative is selected such that its pharmacokinetic properties are superior to the corresponding neutral compound.

Thus, effective concentrations or amounts of one or more of the compounds described herein or pharmaceutically acceptable derivatives thereof are mixed with a suitable pharmaceutical carrier or vehicle for systemic, topical or local administration to form pharmaceutical compositions. Compounds are included in an amount effective for ameliorating one or more symptoms of, or for treating or preventing diseases or disorders associated with nuclear receptor activity or in which nuclear receptor activity is implicated, as described herein. The concentration of active compound in the composition will depend on absorption, inactivation, excretion rates of the active compound, the dosage schedule, amount administered, particular formulation as well as other factors known to those of skill in the art.

The compositions are intended to be administered by a suitable route, including orally, parenterally, rectally, topically and locally. For oral administration, capsules and tablets are presently preferred. The compositions are in liquid, semi-liquid or solid form and are formulated in a manner suitable for each route of administration. Preferred modes of administration include parenteral and oral modes of administration. Oral administration is presently most preferred.

Solutions or suspensions used for parenteral, intradermal, subcutaneous, or topical application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampoules, disposable syringes or single or multiple dose vials made of glass, plastic or other suitable material.

In instances in which the compounds exhibit insufficient solubility, methods for solubilizing compounds may be used. Such methods are known to those of skill in this art, and include, but are not limited to, using co-solvents, such as dimethylsulfoxide (DMSO), using surfactants, such as TWEEN®, or dissolution in aqueous sodium bicarbonate. Derivatives of the compounds, such as prodrugs of the compounds may also be used in formulating effective pharmaceutical compositions.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are typically formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

The composition can contain along with the active ingredient: a diluent such as lactose, sucrose, dicalcium phosphate, or carboxymethylcellulose; a lubricant, such as magnesium stearate, calcium stearate and talc; and a binder such as starch, natural gums, such as gum acacia gelatin, glucose, molasses, polyvinylpyrrolidone, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, acetate, sodium citrate, cyclodextrin derivatives, sorbitan monolaurate, triethanolamine sodium acetate, triethanolamine oleate, and other such agents. Actual methods of preparing such dosage forms are known, or will be apparent, to those skilled in this art; for example, see Remington's Pharmaceutical Sciences, Mack Publishing Company, Easton, Pa., 15th Edition, 1975. The composition or formulation to be administered will, in any event, contain a quantity of the active compound in an amount sufficient to alleviate the symptoms of the treated subject.

Dosage forms or compositions containing active ingredient in the range of 0.005% to 100% with the balance made up from non-toxic carrier may be prepared. For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions may contain 0.001%-100% active ingredient, preferably 0.1-85%, typically 75-95%.

The active compounds or pharmaceutically acceptable derivatives may be prepared with carriers that protect the compound against rapid elimination from the body, such as time release formulations or coatings. The compositions may include other active compounds to obtain desired combinations of properties. The compounds provided herein, or pharmaceutically acceptable derivatives thereof as described herein, may also be advantageously administered for therapeutic or prophylactic purposes together with another pharmacological agent known in the general art to be of value in treating one or more of the diseases or medical conditions referred to hereinabove, such as diseases or disorders associated with nuclear receptor activity or in which nuclear receptor activity is implicated. It is to be understood that such combination therapy constitutes a further aspect of the compositions and methods of treatment provided herein.

1. Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms, preferably capsules or tablets. The tablets, pills, capsules, troches and the like can contain any of the following ingredients, or compounds of a similar nature: a binder; a diluent; a disintegrating agent; a lubricant; a glidant; a sweetening agent; and a flavoring agent.

Examples of binders include microcrystalline cellulose, gum tragacanth, glucose solution, acacia mucilage, gelatin solution, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

If oral administration is desired, the compound could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

Pharmaceutically acceptable carriers included in tablets are binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets are compressed tablets to which different layers of pharmaceutically acceptable substances are applied. Film-coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar-coated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration. Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. No. Re 28,819 and U.S. Pat. No.4,358,603. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

2. Injectable, Solutions and Emulsions

Parenteral administration, generally characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol or ethanol. In addition, if desired, the pharmaceutical compositions to be administered may also contain minor amounts of non-oxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. Typically a therapeutically effective dosage is formulated to contain a concentration of at least about 0.1% w/w up to about 90% w/w or more, preferably more than 1% w/w of the active compound to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

3. Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage (10-1000 mg, preferably 100-500 mg) or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, about 1-50 mg, preferably 5-35 mg, more preferably about 9-30 mg of lyophilized powder, is added per mL of sterile water or other suitable carrier. The precise amount depends upon the selected compound. Such amount can be empirically determined.

4. Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns, preferably less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% isotonic solutions, pH about 5-7, with appropriate salts.

5. Compositions for other Routes of Administration Other routes of administration, such as topical application, transdermal patches, and rectal administration are also contemplated herein.

Transdermal patches, including iotophoretic and electrophoretic devices, are well known to those of skill in the art. For example, such patches are disclosed in U.S. Pat. Nos. 6,267,983, 6,261,595, 6,256,533, 6,167,301, 6,024,975, 6,010715, 5,985,317, 5,983,134, 5,948,433, and 5,860,957.

Pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm.

Tablets and capsules for rectal administration are manufactured using the same pharmaceutically acceptable substance and by the same methods as for formulations for oral administration.

6. Targeted Formulations

The compounds provided herein, or pharmaceutically acceptable derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLVs) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

7. Articles of Manufacture

The compounds or pharmaceutically acceptable derivatives may be packaged as articles of manufacture containing packaging material, a compound or pharmaceutically acceptable derivative thereof provided herein, which is effective for modulating the activity of nuclear receptors, including the farnesoid X receptor and/or orphan nuclear receptors, or for treatment, prevention or amelioration of one or more symptoms of nuclear receptor, including the farnesoid X receptor and/or orphan nuclear receptor, mediated diseases or disorders, or diseases or disorders in which nuclear receptor activity, including the farnesoid X receptor and/or orphan nuclear receptor activity, is implicated, within the packaging material, and a label that indicates that the compound or composition, or pharmaceutically acceptable derivative thereof, is used for modulating the activity of nuclear receptors, including the farnesoid X receptor and/or orphan nuclear receptors, or for treatment, prevention or amelioration of one or more symptoms of nuclear receptor, including the farnesoid X receptor and/or orphan nuclear receptor, mediated diseases or disorders, or diseases or disorders in which nuclear receptor activity, including the farnesoid X receptor and/or orphan nuclear receptor activity, is implicated.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease or disorder in which nuclear receptor activity, including the farnesoid X receptor and/or orphan nuclear receptor activity, is implicated as a mediator or contributor to the symptoms or cause.

E. Evaluation of the Activity of the Compounds

Standard physiological, pharmacological and biochemical procedures are available for testing the compounds to identify those that possess biological activities that modulate the activity or nuclear receptors, including the farnesoid X receptor and/or orphan nuclear receptors. Such assays include, for example, biochemical assays such as binding assays, fluorescence polarization assays, FRET based coactivator recruitment assays (see generally Glickman et al., *J. Biomolecular Screening*, 7 No. 1 3-10 (2002)), as well as cell based assays including the co-transfection assay, the use of LBD-Gal 4 chimeras and protein-protein interaction assays (see, Lehmann. et al., *J. Biol Chem.*, 272(6) 3137-3140 (1997).

High throughput screening systems are commercially available (see, e.g., Zymark Corp., Hopkinton, Mass.; Air Technical Industries, Mentor, Ohio; Beckman Instruments Inc., Fullerton, Calif.; Precision Systems, Inc., Natick, Mass.) that enable these assays to be run in a high throughput mode. These systems typically automate entire procedures, including all sample and reagent pipetting, liquid dispensing timed incubations, and final readings of the microplate in detector(s) appropriate for the assay. These configurable systems provide high throughput and rapid start up as well as a high degree of flexibility and customization. The manufacturers of such systems provide detailed protocols for various high throughput systems. Thus, for example, Zymark Corp. provides technical bulletins describing screening systems for detecting the modulation of gene transcription, ligand binding, and the like.

Assays that do not require washing or liquid separation steps are preferred for such high throughput screening systems and include biochemical assays such as fluorescence polarization assays (see for example, Owicki, J., Biomol Screen October 2000;5(5):297) scintillation proximity assays (SPA) (see for example, Carpenter et al., Methods Mol Biol 2002;190:31-49) and fluorescence resonance energy transfer energy transfer (FRET) or time resolved FRET based coactivator recruitment assays (Mukherjee et al., J Steroid Biochem Mol Biol July 2000;81(3):217-25; (Zhou et al., Mol Endocrinol. October 1998;12(10):1594-604). Generally such assays can be preformed using either the full length receptor, or isolated ligand binding domain (LBD). In the case of the farnesoid X receptor, the LBD comprises amino acids 244 to 472 of the full length sequence.

If a fluorescently labeled ligand is available, fluorescence polarization assays provide a way of detecting binding of compounds to the nuclear receptor of interest by measuring changes in fluorescence polarization that occur as a result of the displacement of a trace amount of the label ligand by the compound. Additionally this approach can also be used to monitor the ligand dependent association of a fluorescently labeled coactivator peptide to the nuclear receptor of interest to detect ligand binding to the nuclear receptor of interest.

The ability of a compound to bind to a receptor, or heterodimer complex with RXR, can also be measured in a homogeneous assay format by assessing the degree to which the compound can compete off a radiolabelled ligand with known affinity for the receptor using a scintillation proximity assay (SPA). In this approach, the radioactivity emitted by a radiolabelled compound generates an optical signal when it is brought into close proximity to a scintillant such as a Ysi-copper containing bead, to which the nuclear receptor is bound. If the radiolabelled compound is displaced from the nuclear receptor the amount of light emitted from the nuclear receptor bound scintillant decreases, and this can be readily detected using standard microplate liquid scintillation plate readers such as, for example, a Wallac MicroBeta reader.

The heterodimerization of the farnesoid X receptor with RXRA can also be measured by fluorescence resonance energy transfer (FRET), or time resolved FRET, to monitor the ability of the compounds provided herein to bind to the farnesoid X receptor or other nuclear receptors. Both approaches rely upon the fact that energy transfer from a donor molecule to an acceptor molecule only occurs when donor and acceptor are in close proximity. Typically the purified LBD of the nuclear receptor of interest is labeled with biotin then mixed with stoichiometric amounts of europium labeled streptavidin (Wallac Inc.), and the purified LBD of RXRα is labeled with a suitable fluorophore such as CY5™. Equimolar amounts of each modified LBD are mixed together and allowed to equilibrate for at least 1 hour prior to addition to either variable or constant concentrations of the sample for which the affinity is to be determined. After equilibration, the time-resolved fluorescent signal is quantitated using a fluorescent plate reader. The affinity of the compound can then be estimated from a plot of fluorescence versus concentration of compound added.

This approach can also be exploited to measure the ligand dependent interaction of a co-activator peptide with a nuclear receptor in order to characterize the agonist or antagonist activity of the compounds disclosed herein. Typically the assay in this case involves the use a recombinant Glutathione-S-transferase (GST)-nuclear receptor ligand binding domain (LBD) fusion protein and a synthetic biotinylated peptide sequenced derived from the receptor interacting domain of a co-activator peptide such as the steroid receptor coactivator 1 (SRC-1). Typically GST-LBD is labeled with a europium chelate (donor) via a europium-tagged anti-GST antibody, and the coactivator peptide is labeled with allophycocyanin via a streptavidin-biotin linkage.

In the presence of an agonist for the nuclear receptor, the peptide is recruited to the GST-LBD bringing europium and allophycocyanin into close proximity to enable energy transfer from the europium chelate to the allophycocyanin. Upon excitation of the complex with light at 340 nm excitation energy absorbed by the europium chelate is transmitted to the allophycocyanin moiety resulting in emission at 665 nm. If the europium chelate is not brought in to close proximity to the allophycocyanin moiety there is little or no energy transfer and excitation of the europium chelate results in emission at 615 nm. Thus the intensity of light emitted at 665 nm gives an indication of the strength of the protein-protein interaction. The activity of a nuclear receptor antagonist can be measured by determining the ability of a compound to competitively inhibit (i.e., $IC_{50}$) the activity of an agonist for the nuclear receptor.

In addition a variety of cell based assay methodologies may be successfully used in screening assays to identify and profile the specificity of compounds of the present invention. These approaches include the co-transfection assay, translocation assays, complementation assays and the use of gene activation technologies to over express endogenous nuclear receptors.

Three basic variants of the co-transfection assay strategy exist, co-transfection assays using full-length nuclear receptor, co transfection assays using chimeric nuclear receptors comprising the ligand binding domain of the nuclear receptor of interest fused to a heterologous DNA binding domain, and assays based around the use of the mammalian two hybrid assay system.

The basic co-transfection assay is based on the co-transfection into the cell of an expression plasmid to express the nuclear receptor of interest in the cell with a reporter plasmid comprising a reporter gene whose expression is under the control of DNA sequence that is capable of interacting with that nuclear receptor. (See for example U.S. Pat. Nos. 5,071,773; 5,298,429, 6,416,957, WO 00/76523). Treatment of the transfected cells with an agonist for the nuclear receptor increases the transcriptional activity of that receptor which is reflected by an increase in expression of the reporter gene, which may be measured by a variety of standard procedures.

For those receptors that function as heterodimers with RXR, such as the farnesoid X receptor, the co-transfection assay typically includes the use of expression plasmids for both the nuclear receptor of interest and RXR. Typical co-transfection assays require access to the full-length nuclear receptor and suitable response elements that provide sufficient screening sensitivity and specificity to the nuclear receptor of interest.

Genes encoding the following full-length previously described proteins, which are suitable for use in the co-transfection studies and profiling the compounds described herein, include rat farnesoid X receptor (GenBank Accession No. NM_021745), human farnesoid X receptor (GenBank Accession No. NM_005123), human RXR α (GenBank Accession No. NM_002957), human RXR β (GenBank Accession No. XM_042579), human RXR.γ (GenBank Accession No. XM_053680), human LXR α (GenBank Accession No. NM_005693), human LXR β (GenBank Accession No. NM_007121), human PPARα (GenBank Accession No. NM_005036) and human PPAR δ (GenBank Accession No. NM_006238).

Reporter plasmids may be constructed using standard molecular biological techniques by placing cDNA encoding for the reporter gene downstream from a suitable minimal promoter. For example luciferase reporter plasmids may be constructed by placing cDNA encoding firefly luciferase immediately down stream from the herpes virus thymidine kinase promoter (located at nucleotides residues −105 to +51 of the thymidine kinase nucleotide sequence) which is linked in turn to the various response elements.

Numerous methods of co-transfecting the expression and reporter plasmids are known to those of skill in the art and may be used for the co-transfection assay to introduce the plasmids into a suitable cell type. Typically such a cell will not endogenously express nuclear receptors that interact with the response elements used in the reporter plasmid.

Numerous reporter gene systems are known in the art and include, for example, alkaline phosphatase Berger, J., et al. (1988) Gene 66 1-10; Kain, S. R. (1997) Methods. Mol. Biol. 63 49-60), β-galactosidase (See, U.S. Pat. No. 5,070,012, issued Dec., 3, 1991 to Nolan et al., and Bronstein, I., et al., (1989) J. Chemilum. Biolum. 4 99-111), chloramphenicol acetyltransferase (See Gorman et al., Mol Cell Biol. (1982) 2 1044-51), β-glucuronidase, peroxidase, β-lactamase (U.S. Pat. Nos. 5,741,657 and 5,955,604), catalytic antibodies, luciferases (U.S. Pat. Nos. 5,221,623; 5,683,888; 5,674,713; 5,650,289; 5,843,746) and naturally fluorescent proteins (Tsien, R. Y. (1998) Annu. Rev. Biochem. 67 509-44).

The use of chimeras comprising the ligand binding domain (LBD) of the nuclear receptor of interest to a heterologous DNA binding domain (DBD) expands the versatility of cell based assays by directing activation of the nuclear receptor in question to defined DNA binding elements recognized by defined DNA binding domain (see WO95/18380). This assay expands the utility of cell based co-transfection assays in cases where the biological response or screening window using the native DNA binding domain is not satisfactory.

In general the methodology is similar to that used with the basic co-transfection assay, except that a chimeric construct is used in place of the full-length nuclear receptor. As with the full-length nuclear receptor, treatment of the transfected cells with an agonist for the nuclear receptor LBD increases the transcriptional activity of the heterologous DNA binding domain which is reflected by an increase in expression of the reporter gene as described above. Typically for such chimeric constructs, the DNA binding domains from defined nuclear receptors, or from yeast or bacterially derived transcriptional regulators such as members of the GAL 4 and Lex A/Umud super families are used.

A third cell based assay of utility for screening compounds of the present invention is a mammalian two-hybrid assay that measures the ability of the nuclear hormone receptor to interact with a cofactor in the presence of a ligand. (See for example, U.S. Pat. Nos. 5,667,973, 5,283,173 and 5,468,614). The basic approach is to create three plasmid constructs that enable the interaction of the nuclear receptor with the interacting protein to be coupled to a transcriptional readout within a living cell. The first construct is an expression plasmid for expressing a fusion protein comprising the interacting protein, or a portion of that protein containing the interacting domain, fused to a GAL4 DNA binding domain. The second expression plasmid comprises DNA encoding the nuclear receptor of interest fused to a strong transcription activation domain such as VP16, and the third construct comprises the reporter plasmid comprising a reporter gene with a minimal promoter and GAL4 upstream activating sequences.

Once all three plasmids are introduced into a cell, the GAL4 DNA binding domain encoded in the first construct allows for specific binding of the fusion protein to GAL4 sites upstream of a minimal promoter. However because the GAL4 DNA binding domain typically has no strong transcriptional activation properties in isolation, expression of the reporter gene occurs only at a low level. In the presence of a ligand, the nuclear receptor-VP16 fusion protein can bind to the GAL4-interacting protein fusion protein bringing the strong transcriptional activator VP16 in close proximity to the GAL4 binding sites and minimal promoter region of the reporter gene. This interaction significantly enhances the transcription of the reporter gene, which can be measured for various reporter genes as described above. Transcription of the reporter gene is thus driven by the interaction of the interacting protein and nuclear receptor of interest in a ligand dependent fashion.

Any compound which is a candidate for activation of the farnesoid X receptor may be tested by these methods. Generally, compounds are tested at several different concentrations to optimize the chances that activation of the receptor will be detected and recognized if present. Typically assays are performed in triplicate and vary within experimental error by less than 15%. Each experiment is typically repeated three or more times with similar results.

Activity of the reporter gene can be conveniently normalized to the internal control and the data plotted as fold activation relative to untreated cells. A positive control compound (agonist) may be included along with DMSO as high and low controls for normalization of the assay data. Similarly, antagonist activity can be measured by determining the ability of a compound to competitively inhibit the activity of an agonist.

Additionally the compounds and compositions can be evaluated for their ability to increase or decrease the expression of genes known to be modulated by the farnesoid X receptor and other nuclear receptors in vivo, using Northern-blot, RT PCR or oligonucleotide microarray analysis to analyze RNA levels. Western-blot analysis can be used to measure expression of proteins encoded by farnesoid X receptor target genes. Genes that are known to be regulated by the farnesoid X receptor include cholesterol 7 α-hydroxylase (CYP7A1), the rate limiting enzyme in the conversion of cholesterol to bile acids, the small heterodimer partner-1 (SHP-1), the bile salt export pump (BSEP, ABCB11), canalicular bile acid export protein, sodium taurocholate cotransporting polypeptide (NTCP, SLC10A1) and intestinal bile acid binding protein (I-BABP).

Established animal models exist for a number of diseases of direct relevance to the claimed compounds and these can be used to further profile and characterize the claimed compounds. These model systems include diabetic dislipidemia using Zucker (fa/fa) rats or (db/db) mice, spontaneous hyperlipidemia using apolipoprotein E deficient mice (ApoE$^{-/-}$), diet-induced hyperlipidemia, using low density lipoprotein receptor deficient mice (LDR$^{-/-}$) and atherosclerosis using both the Apo E($^{-/-}$) and LDL($^{-/-}$) mice fed a western diet, (21% fat, 0.05% cholesterol). Additionally farnesoid X receptor or LXR animal models (e.g., knockout mice) can be used to further evaluate the present compounds and compositions in vivo (see, for example, Sinai, et al., *Cell*, 102: 731-744 (2000), Peet, et al., *Cell*, 93:693-704 (1998)).

F. Methods of Use of the Compounds and Compositions

Methods of use of the compounds and compositions provided herein are also provided. The methods involve both in vitro and in vivo uses of the compounds and compositions for altering nuclear receptor activity, including the farnesoid X receptor and/or orphan nuclear receptor activity, and for treatment, prevention, or amelioration of one or more symptoms of diseases or disorder that are modulated by nuclear receptor activity, including the farnesoid X receptor and/or orphan nuclear receptor activity, or in which nuclear receptor activity, including the farnesoid X receptor and/or orphan nuclear receptor activity, is implicated. Such compounds or compositions will typically exhibit farnesoid X receptor agonist, partial agonist, partial antagonist or antagonist activity in one of the in vitro assays described herein.

Methods of altering nuclear receptor activity, including the farnesoid X receptor, and/or orphan nuclear receptor activity, by contacting the receptor with one or more compounds or compositions provided herein, are provided.

Methods of reducing plasma cholesterol levels and of directly or indirectly modulating cholesterol metabolism, catabolism, synthesis, absorption, re-absorption, secretion or excretion are provided through administering the claimed compounds and compositions provided herein. Methods of reducing dietary cholesterol absorption (see, e.g., International Patent Application Publication No. 00/40965) using the compounds and compositions are provided herein. Also provided, are methods of increasing the expression of ATP-Binding Cassette (ABCA1), thereby increasing reverse cholesterol transport in mammalian cells using the claimed compounds and compositions (see, e.g., International Patent Application Publication No. WO 00/78972).

Methods of reducing plasma triglyceride levels and of directly or indirectly modulating triglyceride metabolism, catabolism, synthesis, absorption, re-absorption, secretion or excretion are provided through administering the claimed compounds and compositions provided herein.

Methods of reducing bile acid levels and of directly or indirectly modulating bile acid metabolism, catabolism, synthesis, absorption, re-absorption, secretion, excretion, or bile acid pool size or composition are provided through administering the claimed compounds and compositions provided herein.

Methods of treatment, prevention, or amelioration of one or more symptoms of a disease or disorder affecting cholesterol, triglyceride, or bile acid levels, or any combination thereof, are provided using the compounds and/or compositions provided herein.

Methods are provided for the treatment, prevention, or amelioration of one or more symptoms of, as well as treating the complications of, hyperlipidemia, hypercholesterolemia, dyslipidemia and lipodystrophy, comprising the administration of the claimed compounds and composition to a subject in need thereof.

The term "hyperlipidemia" refers to the presence of an abnormally elevated level of lipids in the blood. Hyperlipidemia can appear in at least three forms: (1) hypercholesterolemia, i.e., an elevated LDL cholesterol level (120 mg/dL and above); (2) hypertriglyceridemia, i.e., an elevated triglyceride level; (150 mg/dL and above) and (3) combined hyperlipidemia, i.e., a combination of hypercholesterolemia and hypertriglyceridemia.

The term "dyslipidemia" refers to abnormal levels of lipoproteins in blood plasma including both depressed and/or elevated levels of lipoproteins (e.g., elevated levels of Low Density Lipoprotein, (LDL), Very Low Density Lipoprotein (VLDL) and depressed levels of High Density Lipoprotein (HDL) (less than 40 mg/dL)).

Methods are also provided for the treatment, prevention, or amelioration of one or more symptoms of atherosclerosis, atherosclerotic disease, atherosclerotic disease events and atherosclerotic cardiovascular diseases, comprising the administration of the claimed compounds and/or compositions to a subject in need thereof.

Atherosclerosis is the process in which deposits of fatty substances, cholesterol, cellular waste products, calcium and other substances build up in the inner lining of an artery. This buildup is called plaque. It initially affects large and medium-sized arteries. Some hardening of arteries often occurs when people grow older.

Plaques can grow large enough to significantly reduce the blood's flow through an artery. However significant damage to the body can also occur when the artery walls become fragile and rupture. Atherosclerotic plaques that rupture can cause blood clots to form that can block blood flow or break off and travel to another part of the body. If either happens and the blood clot blocks a blood vessel that feeds the heart, it can cause a heart attack. If the blood clot blocks a blood vessel that feeds the brain, it can cause a stroke. And if blood supply to the arms or legs is reduced, it can cause difficulty walking and eventually gangrene.

Accordingly atherosclerosis encompasses a range of vascular diseases and conditions that arise as a result of the primary disease modality. Atherosclerotic cardiovascular diseases can be recognized and understood by physicians practicing in the relevant fields of medicine and include the following: Restenosis following revascularization procedures, coronary heart disease (also known as coronary artery heart disease or ischemic heart disease), cerebrovascular disease including ischemic stroke, multi-infarct dementia, and peripheral vessel disease, including erectile dysfunction.

A compound or composition of the present invention may be administered to prevent or reduce the risk of occurrence, or recurrence where the potential exists, of coronary heart disease event, a cerebrovascular event, and/or intermittent claudication.

Coronary heart disease events are intended to include coronary heart disease death, myocardial infarction and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease.

The term "atherosclerotic disease event" as used herein is intended to encompass coronary heart disease events, cerebrovascular events, and intermittent claudication. It is intended that person who have previously experienced one or more non-fatal atherosclerotic disease events are those for whom the potential for recurrence of such an event exists.

Additionally, the instant invention also provides a method for preventing or reducing the risk of a first or subsequent occurrence of an atherosclerotic disease event comprising the administration of a prophylactically effective amount of a compound or composition of the present invention to a patient at risk for such an event. The patient may already have atherosclerotic disease at the time of administration, or may be at risk for developing it.

Risk factors for developing atherosclerotic disease events include increasing age (65 and over), male gender, a family history of atherosclerotic disease events, high blood cholesterol (especially LDL or "bad" cholesterol over 100 mg/dL), cigarette smoking and exposure to tobacco smoke, high blood pressure, Diabetes mellitus, obesity and physical inactivity.

In another aspect, the method of this invention also serves to remove cholesterol from tissue deposits such as atherosclerotic plaques or xanthomas in a patient with atherosclerotic disease manifest by clinical signs such as angina, claudication, bruits, one that has suffered a myocardial infarction or transient ischemic attack, or one diagnosed by angiography, sonography or MRI, through the administration of the claimed compounds and composition to a subject in need thereof.

Methods of treatment, prevention, or amelioration of one or more of the symptoms of diabetes mellitus, as well as treating the complications of diabetes mellitus, (see, e.g., International Patent Application Publication No. WO 01/82917) are also provided using the compounds and compositions provided herein.

Diabetes mellitus, commonly called diabetes, refers to a disease or condition that is generally characterized by metabolic defects in production and utilization of glucose which result in the failure to maintain appropriate blood sugar levels in the body (see, e.g., LeRoith, D. et al., (eds.), DIABETES MELLITUS (Lippincoft-Raven Publishers, Philadelphia, Pa. U.S.A. 1996)).

In the case of diabetes of the type 2 form, the disease is characterized by insulin resistance, in which insulin loses its ability to exert its biological effects across a broad range of concentrations. This resistance to insulin responsiveness results in insufficient insulin activation of glucose uptake, oxidation and storage in muscle and inadequate insulin repression of lipolysis in adipose tissue and of glucose production and secretion in liver (see, e.g., Reaven, G. M., J. Basic & Clin. Phys. & Pharm. (1998) 9: 387-406 and Flier, J. Ann Rev. Med. (1983) 34:145-60). The resulting condition is elevated blood glucose, which is called "hyperglycemia." Uncontrolled hyperglycemia is associated with increased and premature mortality due to an increased risk for microvascular and macrovascular diseases, including retinopathy (the impairment or loss of vision due to blood vessel damage in the eyes); neuropathy (nerve damage and foot problems due to blood vessel damage to the nervous system); and nephropathy (kidney disease due to blood vessel damage in the kidneys), hypertension, cerebrovascular disease and coronary heart disease. Therefore, control of glucose homeostasis is an important approach for the treatment of diabetes.

Methods of treatment, prevention, or amelioration of one or more of the symptoms of insulin insensitivity or resistance as well as treating the complications of insulin insensitivity or resistance (see, e.g., International Patent Application Publication No. WO 01/82917) are also provided using the compounds and compositions provided herein.

Methods of treatment, prevention, or amelioration of one or more of the symptoms of hyperglycemia as well as treating the complications of hyperglycemia (see, e.g., International Patent Application Publication No. WO 01/82917) are also provided using the compounds and compositions provided herein.

Insulin resistance has been hypothesized to unify the clustering of hypertension, glucose intolerance, hyperinsulinemia, increased levels of triglyceride and decreased HDL cholesterol, and central and overall obesity. The association of insulin resistance with glucose intolerance, an increase in plasma triglyceride and a decrease in high-density lipoprotein cholesterol concentrations, hypertension, hyperuricemia, smaller denser low-density lipoprotein particles, and higher circulating levels of plasminogen activator inhibitor-1, has been referred to as "Syndrome X" (see, e.g., Reaven, G. M., Physiol. Rev. (1995) 75: 473-486). Accordingly, methods of treatment, prevention, or amelioration of any disorders related to diabetes, hyperglycemia or insulin resistance including the cluster of disease states, conditions or disorders that make up "Syndrome X" are provided.

Additionally the instant invention also provides a method for preventing or reducing the risk of hyperglycemia, insulin resistance or diabetes development in a patient, comprising the administration of a prophylactically effective amount of a compound or composition of the present invention to a patient at risk for such an event. The patient may-already be obese, (BMI of 30.0 or greater), overweight (BMI of 25.0 to 30.0) or possess other risk factors for developing diabetes including age, family history and physical inactivity.

Further provided herein are methods for the treatment, prevention, or amelioration of one or more symptoms of cholestasis, as well as for the treatment of the complications of cholestasis by administering a compound or composition provided herein.

Cholestasis is typically caused by factors within the liver (intrahepatic) or outside the liver (extrahepatic) and leads to the accumulation of bile salts, bile pigment bilirubin, and lipids in the blood stream instead of being eliminated normally.

Intrahepatic cholestasis is characterized by widespread blockage of small ducts or by disorders, such as hepatitis, that impair the body's ability to eliminate bile. Intrahepatic cholestasis may also be caused by alcoholic liver disease, primary biliary cirrhosis, cancer that has spread (metastasized) from another part of the body, primary sclerosing cholangitis, gallstones, biliary colic and acute cholecystitis. It can also occur as a complication of surgery, serious injury, cystic fibrosis, infection, or intravenous feeding or be drug induced. Cholestasis may also occur as a complication of pregnancy and often develops during the second and third trimesters.

Extrahepatic cholestasis is most often caused by choledocholithiasis (Bile Duct Stones), benign biliary strictures (noncancerous narrowing of the common duct), cholangiocarcinoma (ductal carcinoma), and pancreatic carcinoma. Extrahepatic cholestasis can occur as a side effect of many medications.

Accordingly, compounds or compositions provided herein may be used for the treatment, prevention, or amelioration of one or more symptoms of intrahepatic or extrahepatic cholestasis, including without limitation, biliary artesia, obstetric cholestasis, neonatal cholestasis, drug induced cholestasis, cholestasis arising from Hepatitis C infection, chronic cholestatic liver disease such as primary biliary cirrhosis (PBC) and primary sclerosing cholangitis (PSC).

Further provided by this invention are methods for treating obesity, as well as treating the complications of obesity, by administering a compound or composition of the present invention. The terms "obese" and "obesity" refers to, according to the World Health Organization, a Body Mass Index (BMI) greater than 27.8 $kg/m^2$ for men and 27.3 $kg/m^2$ for women (BMI equals weight (kg)/height ($m^2$). Obesity is linked to a variety of medical conditions including diabetes and an atherosclerotic disease event. (See, e.g., Barrett-Conner, E., Epidemol. Rev. (1989) 11: 172-181; and Knowler, et al., Am. J Clin. Nutr. (1991) 53:1543-1551). Accordingly the claimed compounds or compositions that may be used for treating obesity or its complications, and can be identified, formulated, and administered as previously described above.

G. Combination Therapy

Also contemplated herein is combination therapy using one or more compounds or compositions provided herein, or a pharmaceutically acceptable derivative thereof, in combination with one or more of the following: antihyperlipidemic agents, plasma HDL-raising agents, antihypercholesterolemic agents, cholesterol biosynthesis inhibitors (such as HMG CoA reductase inhibitors, such as lovastatin, simvastatin, pravastatin, fluvastatin, atorvastatin and rivastatin), acyl-coenzyme A: cholesterol acytransferase (ACAT) inhibitors, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, anti-oxidant vitamins, β-blockers, anti-diabetes agents, angiotensin III antagonists, angiotensin converting enzyme inhibitors, platelet aggregation inhibitors, fibrinogen receptor antagonists, LXR α or β agonists, antagonists or partial agonists, aspirin or fibric acid derivatives. The compound or composition provided herein, or pharmaceutically acceptable derivative thereof, is administered simultaneously with, prior to, or after administration of one or more of the above agents. Pharmaceutical compositions containing a compound provided herein and one or more of the above agents are also provided.

Combination therapy includes administration of a single pharmaceutical dosage formulation which contains a compound of the present invention and one or more additional active agents, as well as administration of a compound of the present invention and each active agent in its own separate pharmaceutical dosage formulation. For example, a farnesoid X receptor agonist, partial agonist, partial antagonist, or antagonist of the present invention and an HMG-CoA reductase inhibitor can be administered to the patient together in a single oral dosage composition such as a tablet or capsule, or each agent administered in separate oral dosage formulations. Where separate dosage formulations are used, the compounds described herein and one or more additional active agents can be administered at essentially the same time, i.e., concurrently, or at separately staggered times, i.e., sequentially; combination therapy is understood to include all these regimens.

An example of combination therapy that modulates, or prevents the onset of the symptoms, or associated complications of atherosclerosis, is administered with one or more of the following active agents: an antihyperlipidemic agent; a plasma HDL-raising agent; an antihypercholesterolemic agent, such as a cholesterol biosynthesis inhibitor, e.g., an hydroxymethylglutaryl (HMG) CoA reductase inhibitor (also referred to as statins, such as lovastatin, simvastatin, pravastatin, fluvastatin, and atorvastatin), an HMG-CoA synthase inhibitor, a squalene epoxidase inhibitor, or a squalene synthetase inhibitor (also known as squalene synthase inhibitor); an acyl-coenzyme A cholesterol acyltransferase (ACAT) inhibitor, such as melinamide; probucol; nicotinic acid and the salts thereof and niacinamide; a cholesterol absorption inhibitor, such as β-sitosterol; a bile acid sequestrant anion exchange resin, such as cholestyramine, colestipol or dialkylaminoalkyl derivatives of a cross-linked dextran; an LDL (low density lipoprotein) receptor inducer; fibrates, such as clofibrate, bezafibrate, fenofibrate, and gemfibrizol; vitamin $B_6$ (also known as pyridoxine) and the pharmaceutically acceptable salts thereof, such as the HCl salt; vitamin $B_{12}$ (also known as cyanocobalamin); vitamin $B_3$ (also known as nicotinic acid and niacinamide, supra); anti-oxidant vitamins, such as vitamin C and E and beta carotene; a beta-blocker; LXR α or β agonists, antagonists, or partial agonists, an angiotensin II antagonist; an angiotensin converting enzyme inhibitor; and a platelet aggregation inhibitor, such as fibrinogen receptor antagonists (i.e., glycoprotein IIb/IIIa fibrinogen receptor antagonists) and aspirin.

A compound or composition of the present invention is preferably administered with a cholesterol biosynthesis inhibitor, particularly an HMG-CoA reductase inhibitor. The term HMG-CoA reductase inhibitor is intended to include all pharmaceutically acceptable salt, ester, free acid and lactone forms of compounds which have HMG-CoA reductase inhibitory activity and, therefore, the use of such salts, esters, free acids and lactone forms is included within the scope of this invention. Other HMG-CoA reductase inhibitors can be readily identified using assays well-known in the art. For instance, suitable assays are described or disclosed in U.S. Pat. No. 4,231,938 and WO 84102131. Examples of suitable HMG-CoA reductase inhibitors include, but are not limited to, lovastatin (MEVACOR®; see, U.S. Pat. No. 4,231,938); simvastatin (ZOCOR®; see, U.S. Pat. No. 4,444,784); pravastatin sodium (PRAVACHOL®; see, U.S. Pat. No. 4,346,227); fluvastatin sodium (LESCOL®; see, U.S. Pat. No. 5,354,772); atorvastatin calcium (LIPITOR®); see, U.S. Pat. No.5,273,995) and rivastatin (also known as cerivastatin; see, U.S. Pat. No. 5,177,080). The structural formulas of these and additional HMG-COA reductase inhibitors that can be used in the methods of the present invention are described at page 87 of M. Yalpani, "Cholesterol Lowering Drugs," *Chemistry & Industry*, pp. 85-89 (5 Feb. 1996). In one embodiment, the HMG-CoA reductase inhibitor is selected from lovastatin and simvastatin.

Dosage information for HMG-COA reductase inhibitors is well known in the art, since several HMG-CoA reductase inhibitors are marketed in the U.S. In particular, the daily dosage amounts of the HMG-CoA reductase inhibitor may be the same or similar to those amounts which are employed for anti-hypercholesterolemic treatment and which are described in the *Physicians' Desk Reference* (PDR). For example, see the 50th Ed. of the PDR, 1996 (Medical Economics Co); in particular, see at page 216 the heading "Hypolipidemics," sub-heading "HMG-CoA Reductase Inhibitors," and the reference pages cited therein. Preferably, the oral dosage amount of HMG-CoA reductase inhibitor is from about 1 to 200 mg/day and, more preferably, from about 5 to 160 mg/day. However, dosage amounts will vary depending on the potency of the specific HMG-CoA reductase inhibitor used as well as other factors as noted above. An HMG-CoA reductase inhibitor which has sufficiently greater potency may be given in sub-milligram daily dosages.

As examples, the daily dosage amount for simvastatin may be selected from 5 mg, 10 mg, 20 mg, 40 mg, 80 mg and 160 mg for lovastatin, 10 mg, 20 mg, 40 mg and 80 mg; for fluvastatin sodium, 20 mg, 40 mg and 80 mg; and for pravastatin sodium, 10 mg, 20 mg, and 40 mg. The daily dosage amount for atorvastatin calcium may be in the range of from 1 mg to 160 mg and, more particularly, from 5 mg to 80 mg. Oral administration may be in a single or divided doses of two, three, or four times daily, although a single daily dose of the HMG-CoA reductase inhibitor is preferred.

Diabetic patients are likely to suffer from premature development of atherosclerotic disease events and increased rate of cardiovascular and peripheral vascular diseases. Hyperlipidemia and dyslipidemia are important precipitating factors for these diseases. See, e.g., Wilson, J. et al.,-(ed.), Disorders of Lipid Metabolism, Chapter 23, Textbook of Endocrinology, 9th Edition, (W. B. Sanders Company, Philadelphia, Pa. U.S.A. 1998). Dyslipidemia is characterized by abnormal levels of lipoproteins in blood plasma (e.g. elevated levels of LDL, VLDL and depressed levels of HDL), and has been shown to be one of the main contributors to the increased incidence of coronary events and deaths among diabetic subjects (see, e.g., Joslin, E. Ann. Chim. Med. (1927) 5: 1061-1079). Epidemiological studies since then have confirmed the association and have shown a several-fold increase in coronary deaths among diabetic subjects when compared with non-diabetic subjects (see, e.g., Garcia, M. J. et al., Diabetes (1974) 23: 105-11 (1974); and Laakso, M. and Lehto, S., Diabetes Reviews (1997) 5(4): 294-315).

The methods of the present invention can be used effectively in combination with one or more additional active anti-diabetes agents depending on the desired target therapy (see, e.g., Turner, N. et al. Prog. Drug Res. (1998) 51: 33-94; Haffner, S. Diabetes Care (1998) 21: 160-178; and DeFronzo, R. et al. (eds.), Diabetes Reviews (1997) Vol. 5 No. 4).

A number of studies have investigated the benefits of combination therapies with oral agents (see, e.g., Mahler, R., J. Clin. Endocrinol. Metab. (1999) 84: 1165-71; United Kingdom Prospective Diabetes Study Group: UKPDS 28, Diabetes Care (1998) 21: 87-92; Bardin, C. W.,(ed.), CURRENT THERAPY IN ENDOCRINOLOGY AND METABOLISM, 6th Edition (Mosby—Year Book, Inc., St. Louis, Mo. 1997); Chiasson, J. et al., Ann. Intern. Med. (1994) 121: 928-935; Coniff, R. et al., Clin. Ther. (1997) 19: 16-26; Coniff, R. et al., Am. J. Med. (1995) 98: 443-451; and Iwamoto, Y. et al, Diabet. Med. (1996) 13 365-370; Kwiterovich, P. Am. J. Cardiol (1998) 82(12A): 3U-17U). These studies indicate that the modulation of hyperlipidemia associated with diabetes can further improve the treatment outcome of diabetics.

Accordingly, another combination therapy claimed herein is suitable for treating diabetes and its related symptoms, complications, and disorders, and includes the co-administration of the compounds or compositions provided herein with for example, sulfonylureas (such as chlorpropamide, tolbutamide, acetohexamide, tolazamide, glyburide, gliclazide, glynase, glimepiride, and glipizide), biguanides (such as mefformin), thiazolidinediones (such as ciglitazone, pioglitazone, troglitazone, and rosiglitazone); and related insulin sensitizers, such as selective and non-selective activators of PPARα, PPARβ, and PPARγ; LXR α or β agonists, antagonists and partial agonists, dehydroepiandrosterone (also referred to as DHEA or its conjugated sulphate ester, DHEA-$SO_4$); antiglucocorticoids; TNF α-inhibitors; α-glucosidase inhibitors (such as acarbose, miglitol, and voglibose), pramlintide (a synthetic analog of the human hormone amylin), other insulin secretogogues (such as repaglinide, gliquidone, and nateglinide), insulin, as well as the active agents discussed above for treating atherosclerosis.

Another example of combination therapy claimed herein is the co-administration of the claimed compounds or compositions provided herein with compounds or compositions for treating obesity or obesity-related disorders, wherein the claimed compounds can be effectively used in combination with, for example, phenylpropanolamine, phentermine, diethylpropion, mazindol; fenfluramine, dexfenfluramine, phentiramine, $β_3$ adrenoceptor agonist agents; sibutramine, gastrointestinal lipase inhibitors (such as orlistat), LXR α or β agonists, antagonists and partial agonists, and leptins. Other agents used in treating obesity or obesity-related disorders include neuropeptide Y, enterostatin, cholecytokinin, bombesin, amylin, histamine $H_3$ receptors, dopamine $D_2$ receptors, melanocyte stimulating hormone, corticotrophin releasing factor, galanin and gamma amino butyric acid (GABA).

Another example of a claimed combination therapy is the co-administration of the claimed compound or composition provided herein with compounds or compositions for treating cholestasis and its related symptoms, complications, and disorders. Such co-administered compounds include for example, Actigall (Ursodeoxycholic acid—UDCA), corticosteroids, anti-infective agents (Rifampin, Rifadin, Rimactane), anti-viral agents, Vitamin D, Vitamin A, phenobarbital, cholestyramine, UV light, antihistamines, oral opiate receptor antagonists and biphosphates, for the treatment, prevention, or amelioration of one or more symptoms of intrahepatic or extrahepatic cholestasis. Dosage information for these agents is well known in the art.

The following examples are provided for illustrative purposes only and are not intended to limit the scope of the invention.

EXAMPLE 1

Preparation of 3,6,7,8-tetrahydro-imidazo[4,5-D] azepine-4-carboxylic acid ethyl ester

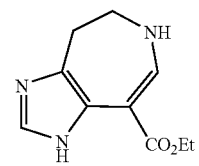

A mixture of histamine dihydrochloride (5.52 g, 30 mmol), ethyl bromopyruvate (5.0 mL, 36 mmol), and active carbon (500 mg) in anhydrous EtOH (80 mL) was refluxed under nitrogen for 24 hours. After cooling to room temperature, $Et_3N$ (30 mL) was added, and the mixture was refluxed at 90° C. for 6 hours. The active carbon was filtered off, and the filtrate was concentrated in vacuo. The residue was taken up in $CHCl_3$, and washed twice with water, then dried over $Na_2SO_4$, and evaporated in vacuo. The residual oil was purified by column chromatography on silica gel eluting with hexane-EtOAc (60:40) to give the title compound as a pale-yellow solid. $^1$H-NMR ($CDCl_3$): δ 7.49 (1H, d)), 7.00 (1H, s), 6.79 (1H, s), 4.85 (1H, br s), 4.30 (2H, q), 3.38 (2H, m), 3.06 (2H, m), 1.36 (3H, t); MS (ES): 208 ($MH^+$).

EXAMPLE 2

Preparation of 6-(4-fluoro-benzoyl)-3,6,7,8-tetrahydro-imidazo[4,5-D]azepine-4-carboxylic acid ethyl ester

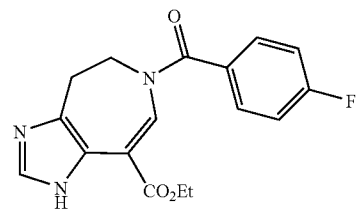 [SMILES: CCOC(=O)C1=CN(C(=O)c2ccc(F)cc2)CCc2nc[nH]c21]

4-fluorobenzoyl chloride was added dropwise to a stirred solution of 3,6,7,8-tetrahydro-imidazo[4,5-d]azepine-4-carboxylic acid ethyl ester (Example 1, 60 mg, 0.29 mmol) and $Et_3N$ (0.2 mL) in dry $CH_2Cl_2$ at 0° C. under nitrogen. The resulting mixture was allowed to warm to ambient temperature overnight. The solvent was removed in vacuo, and the residue was purified by column chromatography on silica gel eluting with hexane-EtOAc (80:20) to give the title compound as a yellow solid. $^1$H-NMR($CDCl_3$): δ 8.27-8.21 (3H, m), 7.16 (2H, t), 7.00 (1 H, s), 5.10 (1 H, br s), 4.35 (2H, q), 3.56 (2H, m), 3.14 (2H, t), 1.39 (3H, t); MS (ES): 330 (MH+).

EXAMPLE 3

Preparation of 6-(3,4-difluoro-benzoyl)-5,6-dihydro-4H-thieno[2,3-D]azepine-8-carboxylic acid ethyl ester

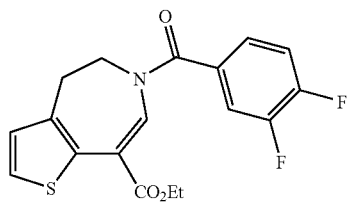 [SMILES: CCOC(=O)C1=CN(C(=O)c2ccc(F)c(F)c2)CCc2ccsc21]

A. To a solution of 3-thiopheneacetonitrile (5 g, 40.6 mmol) in anhydrous ether (100 mL) was added lithium aluminum hydride (3 g, 81.2 mmol) in portions at 0° C. under nitrogen. The suspension was stirred for 30 min at 20° C. and heated to reflux for 2 h with stirring under nitrogen. After cooling, the reaction mixture was quenched with 10% aqueous Rochelle's salt (Yamada, F. et al. *Heterocycles*, 1998, 49:451-457). Solid was removed by filtration and washed with ether and DCM. The filtrate was washed with brine and dried over MgSO$_4$. Evaporation of solvent gave an oil (4.73 g), which was used in the next step without purification. $^1$H-NMR(CDCl$_3$): δ7.27 (1H, m), 6.95-7.05 (2H, m), 2.96 (2H, t), 2.78 (2H, t).

B. The compound from the previous step was used in a manner similar to that described in Example 1 to prepare 5,6-dihydro-4H-thieno[2,3-d]azepine-8-carboxylic acid ethyl ester. MS (ES): 224 (MH+).

C. The title compound was prepared in a manner similar to that described in Example 2 by using 5,6-dihydro-4H-thieno[2,3-d]azepine-8-carboxylic acid ethyl ester and 3,4-difluoro-benzoyl chloride. $^1$H-NMR(CDCl$_3$): δ 8.01 (1 H, s), 7.47 (1 H, m), 7.36 (1H, m), 7.27 (2H, m), 6.85 (1H, d), 4.23 (2H, q), 4.13 (2H, m), 3.15 (2H, t), 1.23 (3H, t). MS (ES): 364 (MH+).

EXAMPLE 4

Preparation of ethyl 1,2,3,6-tetrahydroazepino[4,5-b]indole-5-carboxylate

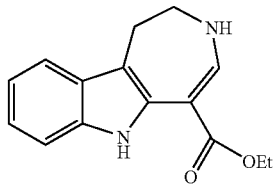 [SMILES: CCOC(=O)C1=CNCCc2c1[nH]c1ccccc21]

A mixture of tryptamine hydrochloride (1.96 g, 10 mmol), ethyl 3-bromopyruvate (1.67 mL, 1.2 equiv) and decolorizing charcoal (0.5 g) in absolute ethanol was heated to reflux under nitrogen overnight. TEA was added and the reaction mixture was heated to reflux for another 7.5 hours. After cooling, charcoal was removed by filtration and washed with ethanol. The filtrate was concentrated under vacuum and diluted with water (20 mL). It was then extracted with EtOAc (3×30 mL) and the combined organic layers were washed with brine and dried over MgSO$_4$. Evaporation of solvent and recrystallization from DCM-Hexane gave the title compound (1.17 g). $^1$H-NMR (CDCl$_3$): δ 10.49 (1 H, br s), 7.79 (1H, d), 7.43 (1 H, d), 7.43 (1 H, d). 7.06 (2H, m), 5.27 (1 H, br s), 4.29 (2H, q) 3.58 (2H, m), 3.17 (2H, m), 1.36 (3H, t); MS (ES): 257 (MH+).

EXAMPLE 5

Preparation of ethyl 3-(4-fluorobenzoyl)-1,2,3,6-tetrahydroazepino[4,5-b]indole-5-carboxylate

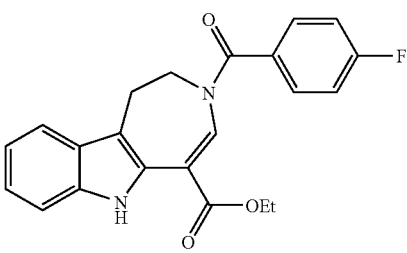 [SMILES: CCOC(=O)C1=CN(C(=O)c2ccc(F)cc2)CCc2c1[nH]c1ccccc21]

To a solution of ethyl 1,2,3,6-tetrahydroazepino[4,5-b]indole-5-carboxylate (Example 4, 52 mg, 0.2 mmol) in DCM was added 4-fluorobenzoyl chloride (36 μL, 0.2 mmol) and TEA (56 μL, 0.4 mmol) and the mixture was shaken overnight at 20° C. Trisamine resin (50 mg) was added and the suspension was shaken for 2 hours at 20° C. The resin was removed by filtration through a Florisil® cartridge. Evaporation of solvent gave a crude product, which was purified by trituration with methanol to give the title compound (28 mg); $^1$H-NMR (CDCl$_3$): δ 10.31 (1 H, br s), 7.79 (1 H, s), 7.41 (2H, m), 7.36 (1H, d), 6.90-7.04 (5H, m), 3.99-4.06 (4H, m), 3.06 (2H, t), 1.02 (3H, t); MS (ES): 379 (MH+).

EXAMPLE 6

Preparation of 3-(4-fluoro-benzoyl)-1,2,3,4,5,6,7,8,9,10-decahydro-azepino[4,5-b]indole-5-carboxylic acid ethyl ester

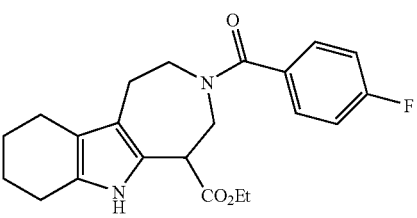 [SMILES: CCOC(=O)C1CN(C(=O)c2ccc(F)cc2)CCc2c1[nH]c1c2CCCC1]

A solution of 3-(4-fluoro-benzoyl)-1,2,3,6-tetrahydroazepino[4,5-b]indole-5-carboxylic acid ethyl ester (Example 5, 1.3 g, 3.4 mmol) in 60 mL of glacial acetic acid containing 500 mg of Adams catalyst was subjected to hydrogenation for 14 hours at room temperature and under 45psi of hydrogen. (Boekelheide, V. and Liu, C-T, *J. Am. Chem. Soc.* 1952, 74, 4920-4922). The catalyst was removed by filtration and the filtrate was concentrated in vacuo. The crude product was purified by preparative normal-phase HPLC eluting with 40% EtOAc-Hexane. $^1$H-NMR(CDCl$_3$): δ 7.99 (1H, s), 7.40-

7.37 (2H, m), 7.11-7.06 (2H, m), 4.22-4.15 (4H, m), 3.54 (1H, m), 2.75 (1H, m), 2.54-2.45 (2H, m), 2.31 (2H, m), 1.76 (4H, m), 1.61 (2H, m), 1.32 (3H, m); MS (ES): 385 (MH$^+$).

EXAMPLE 7 Preparation of 3-(4-fluoro-benzoyl)-1, 2,3,6,7,8,9,10-octahydro-azepino[4,5-b]indole-5-carboxylic acid ethyl ester

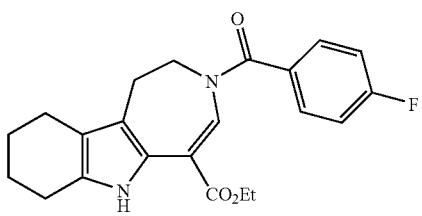 [SMILES: CCOC(=O)C1=CN(C(=O)c2ccc(F)cc2)CCc2c1[nH]c1c2CCCC1]

To a solution of 3-(4-fluoro-benzoyl)-1,2,3,4,5,6,7,8,9,10-decahydro-azepino[4,5-b]indole-5-carboxylic acid ethyl ester (Example 6, 60 mg, 0.16 mmol) in DCM (2 mL) was added TEA (45 µL, 0.32 mmol) and a solution of tert-butyl hypochlorite (19.2 mL, 0.16 mmol) in DCM (1 mL) at 0° C. and the mixture was stirred for 0.5 h at 0° C. Cold water was added to quench the reaction mixture and the aqueous layer was separated and extracted with DCM. The combined organic layer was washed with water and dried over MgSO$_4$. Evaporation of solvent gave a crude, which was purified by column chromatography on silica gel, eluting with MeOH-DCM (1:19) to give the title compound (6.5 mg) with some starting material (27 mg) recovered. $^1$H-NMR(CDCl$_3$): δ 10.07 (1H, s), 7.57 (2H, m), 7.52 (1H, s), 7.10 (2H, m), 4.19 (2H, q), 4.07 (2H, t), 2.89 (2H, t), 2.62 (2H, t), 2.43 (2H, t), 1.80 (4H, m), 1.19 (3H, t). MS (ES): 383 (MH$^+$).

EXAMPLE 8

A. Preparation of 2-(1-tert-butoxycarbonyl indol-3-yl)propionitrile

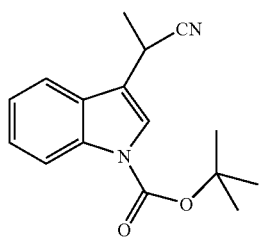 [SMILES: CC(C#N)c1cn(C(=O)OC(C)(C)C)c2ccccc12]

To a stirred solution of 3-indolylacetonitrile (3.9 g, 25 mmol) in DCM (100 mL, anhyd) was added BOC anhydride (6.5 g, 30 mmol), DMAP (3.6 g, 30 mmol) and TEA (4.2 mL, 30 mmol). After 2 h the reaction mixture was diluted with DCM (100 mL), washed with 1 N HCl (2×50 mL) and brine, then dried (Na$_2$SO$_4$), concentrated and chromatographed (silica gel, 6% EtOAc/Hex) to yield (1-tert-butoxycarbonyl indol-3-yl)acetonitrile (5.4 g, 84%) as a pale yellow solid. $^1$H-NMR (CDCl$_3$): δ 8.17 (1H, br d), 7.64 (1H, br s), 7.52 (1H, br d), 7.38 (1H, app t), 7.30 (1H, app t), 3.78 (2H, s), 1.68 (9H, s).

To a stirred solution of (1-tert-butoxycarbonyl indol-3-yl)acetonitrile (5.30 g, 20.7 mmol) in THF (20 mL, anhyd) chilled to −78° C. was added dropwise a 1.0M solution of LiHMDS in THF (21 mL, 21 mmol). After 40 min iodomethane (1.3 mL, 21 mmol) was added rapidly, and the reaction mixture was allowed to warm to ambient temperature. After 15 h the reaction was quenched by addition of 0.2N HCl (100 mL) and extracted with Et$_2$O (2×100 mL). The combined extracts were washed with brine, dried (Na$_2$SO$_4$), concentrated and chromatographed (silica gel, 6% EtOAc/Hex) to give the title compound (4.0 g, 71%) as a light yellow oil. $^1$H-NMR (CDCl$_3$): δ 8.17 (1H, br d), 7.60 (2H, m), 7.37 (1H, br d), 7.30 (1H, app t), 4.10 (1H, q), 1.76 (3H, d), 1.68 (9H, s).

B. Preparation of 2-(1 H-indol-3-yl)propylamine

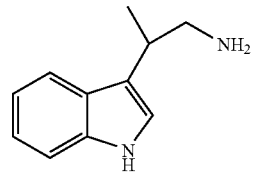

To a stirred solution of 2-(1-tert-butoxycarbonyl indol-3-yl)propionitrile (4.00 g, 14.8 mmol) in DCM (10 mL) was added TFA (10 mL) with caution. After 1 h the reaction was diluted with DCM (40 mL), washed with water (2×40 mL) and brine, then dried (Na$_2$SO$_4$), and concentrated under reduced pressure to give 2-(1H-indol-3-yl)propionitrile (2.5 g, 99%) as a pale brown solid. $^1$H-NMR (CDCl$_3$): δ 8.25 (1H, d), 7.69 (1H, s), 7.65 (1H, d), 7.45 (1H, app t), 7.37 (1H, app t), 4.12 (1H, q), 1.79 (3H, d).

To a stirred suspension of LAH (3.4 g, 90 mmol) in THF (40 mL, anhyd) chilled to 0° C. was added a solution of 2-(1H-indol-3-yl)propionitrile (2.5 g, 14.7 mmol) in THF (40 mL, anhyd). The reaction mixture was allowed to warm to ambient temperature and then heated at reflux. After 1 h the reaction mixture was cooled to 0° C. and quenched cautiously with wet THF (5-10% H$_2$O) until gas evolution had ceased. The resulting mixture was filtered through Celite™ and concentrated to give a brown residue. The filtering agent was rinsed with Et$_2$O (100 mL), which was combined with the residue, dried (Na$_2$SO$_4$), and concentrated under reduced pressure to yield the title compound (2.1 g, 82%) as a pale amber oil. $^1$H-NMR (CDCl$_3$): δ 8.28 (1 H, br s), 7.61 (1H, d), 7.36 (1H, d), 7.16 (1H, app t), 7.08 (1H, app t), 6.96 (1H, br s), 3.41 (2H, br s), 3.19 (1H, q), 2.95 (2H, app d), 1.35 (3H, d).

C. Preparation of ethyl 1-methyl-1,2,3,6-tetrahydroazepino[4,5-b]indole-5-carboxylate

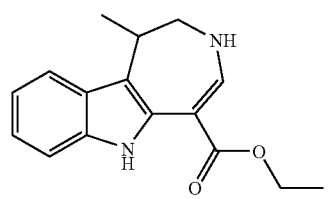 [SMILES: CCOC(=O)C1=CNCC(C)c2c1[nH]c1ccccc21]

In a manner similar to Example 1, the title compound was prepared from 2-(1H-indol-3-yl)propylamine and ethyl pyruvate. MS(ESI): 271 (MH$^+$).

D. Preparation of ethyl 3-(4-fluorobenzoyl)-1-methyl-1,2,3,6-tetrahydro-azepino[4,5-b]indole-5-carboxylate

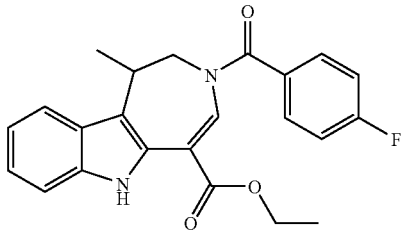 [SMILES: CCOC(=O)C1=CN(C(=O)c2ccc(F)cc2)CC(C)c2c1[nH]c1ccccc21]

In a manner similar to Example 2, the title compound was prepared from ethyl 1-methyl-1,2,3,6-tetrahydroazepino[4,5-b]indole-5-carboxylate and 4-fluorobenzoyl chloride. $^1$H-NMR (CDCl$_3$): δ 10.54 (1H, br s), 7.97 (1H, s), 7.63-7.68 (2H, m), 7.58 (1H, d), 7.39 (1H, d), 7.09-7.23 (4H, m), 5.28 (1H, dd), 4.25 (2H, m), 3.85 (1H, m), 3.18 (1H, d), 1.34 (3H, d), 1.22 (3H, t); MS(ESI): 393 (MH$^+$).

EXAMPLE 9

Preparation of ethyl 1,1-dimethyl-1,2,3,6-tetrahydro-azepino[4,5-b]indole-5-carboxylate

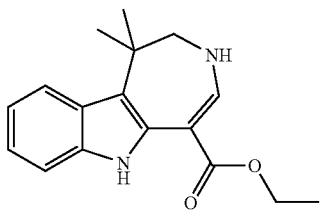 [SMILES: CCOC(=O)C1=CNCC(C)(C)c2c1[nH]c1ccccc21]

In a manner similar to Example 8, the title compound was prepared by using 2 equiv iodomethane during alkylation of (1-tert-butoxycarbonyl indol-3-yl)acetonitrile. MS(ESI): 285 (MH$^+$).

EXAMPLE 10

Preparation of ethyl 1,1-dimethyl-3-(4-fluorobenzoyl)-1,2,3,6-tetrahydro-azepino[4,5-b]indole-5-carboxylate

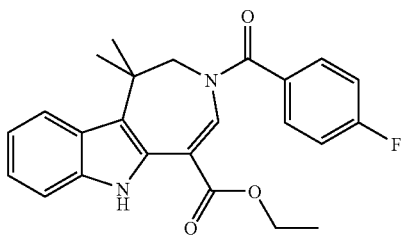 [SMILES: CCOC(=O)C1=CN(C(=O)c2ccc(F)cc2)CC(C)(C)c2c1[nH]c1ccccc21]

As described in Example 2, the title compound was prepared from ethyl 1,1-dimethyl-1,2,3,6-tetrahydro-azepino[4,5-b]indole-5-carboxylate and 4-fluorobenzoyl chloride.

$^1$H-NMR (DMSO-d$_6$): δ 10.82 (1H, s), 7.76 (1H, d), 7.65 (1H, s), 7.61 (2H, dd), 7.54 (1H, d), 7.35 (2H, app t), 7.09 (1 H, app t), 6.98 (1 H, app t), 4.22 (2H, q), 3.97 (2H, brs), 1.52 (6H, s), 1.17 (3H, t); MS(ESI): 407 (MH$^+$).

EXAMPLE 11

Preparation of 3-(4-fluoro-benzoyl)-1,1-dimethyl-1,2,3,6,7,8,9,10-octahydro-azepino[4,5-b]indole-5-carboxylic acid ethyl ester

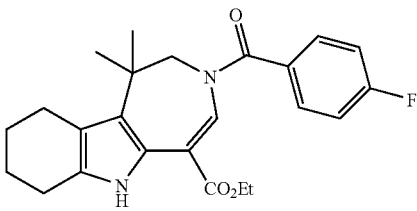 [SMILES: CCOC(=O)C1=CN(C(=O)c2ccc(F)cc2)CC(C)(C)c2c1[nH]c1c2CCCC1]

A solution of 3-(4-fluoro-benzoyl)-1,1-dimethyl-1,2,3,6-tetrahydro-azepino[4,5-b]indole-5-carboxylic acid ethyl ester (1.03 g) in 40 mL of glacial acetic acid containing 370 mg of Adams catalyst was subjected to hydrogenation under atmospheric pressure of hydrogen for 20 hours at room temperature. (Boekelheide, V. and Liu, C-T, J. Am. Chem. Soc. 1952, 74, 4920-4922). The catalyst was removed by filtration and the filtrate was concentrated in vacuo. The crude product was purified first by column chromatography on silica gel eluting with hexane/DCM and then by preparative normal phase HPLC eluting with hexane/DCM. The title compound was obtained as yellow solid (64 mg). $^1$H-NMR(CDCl$_3$):δ 10.18 (1H, s), 7.64-7.59 (2H, m), 7.41 (1H, s), 7.13-7.07 (2H, m), 4.18 (2H, q), 3.95 (2H, brs), 2.68-2.61 (4H, m), 1.78 (4H, m), 1.39 (6H, s), 1.18 (3H, t); MS (ES): 411 (MH$^+$).

EXAMPLE 12

Preparation of 6-(3,4-difluoro-benzoyl)-4,4-dimethyl-5,6-dihydro-4H-thieno[2,3-d]azepine-8-carboxylic acid ethyl ester

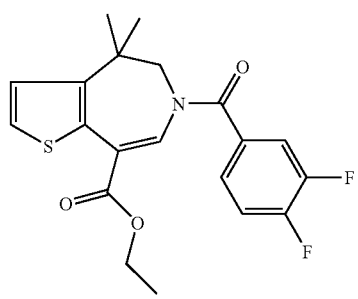 [SMILES: CCOC(=O)C1=CN(C(=O)c2ccc(F)c(F)c2)CC(C)(C)c2ccsc21]

To a solution of thiophene-3-acetonitrile (6.15 g, 50 mmol) and MeI (12.5 mL, 4 equiv) in DMF (200 mL) was added sodium hydride (6 g, 60%, 3 equiv) at 0° C. under nitrogen and the reaction mixture was stirred for 3 h at 0° C. It was then quenched with water and extracted with hexane (3×100 mL). The combined organic layer was washed with water and dried over MgSO$_4$. Evaporation of solvent afforded 2-methyl-2-thiophen-3-yl-propionitrile as an oil, which was used in next step without further purification. ¹H-NMR(CDCl₃): δ 8.02 (1H, m), 7.35 (1H, dd), 7.12 (1H, dd), 2.96 (3H, s), 2.89 (3H, s).

To a solution of 2-methyl-2-thiophen-3-yl-propionitrile in anhydrous ether (200 mL) was added lithium aluminumhydride (5.7 g, 3 equiv) at 0° C. under nitrogen. Stirring was continued for 0.5 h at 20° C. and 3 h at reflux under nitrogen. After cooling, it was quenched with 10% aqueous Rochelle's salt (Yamada, F. et al. *Heterocycles,* 1998, 49:451-457) and the solid was removed with filtration and washed with ether. The combined filtrate was washed with water and dried over MgSO₄. Evaporation of solvent afforded 2-methyl-2-thiophen-3-yl-propylamine as an oil (4.62 g). ¹H-NMR (CDCl₃): δ 7.29 (1H, dd), 7.03 (1H, dd), 6.99 (1H, dd), 2.74 (2H, s), 1.29 (6H, s).

2-methyl-2-thiophen-3-yl-propylamine was used in a manner similar to that described in Example 1 to prepare 4,4-dimethyl-5,6-dihydro-4H-thieno[2,3-d]azepine-8-carboxylic acid ethyl ester. MS (ES): 252 (MH⁺).

The title compound was prepared in a manner similar to that described in Example 2 by using 4,4-dimethyl-5,6-dihydro-4H-thieno[2,3-d]azepine-8-carboxylic acid ethyl ester. ¹H-NMR(CDCl₃): δ 7.82 (1H, s), 7.49 (1H, m), 7.37 (1H, m), 7.26 (2H, m), 7.05 (1H, d), 4.23 (2H, q), 3.95 (2H, t), 1.23 (3H, t). MS (ES): 392 (MH⁺)

EXAMPLE 13

Preparation of 6-(3,4-difluoro-benzoyl)-4,4-dimethyl-1,4,5,6-tetrahydro-pyrrolo[2,3-d]azepine-2,8-dicarboxylic acid dimethyl ester

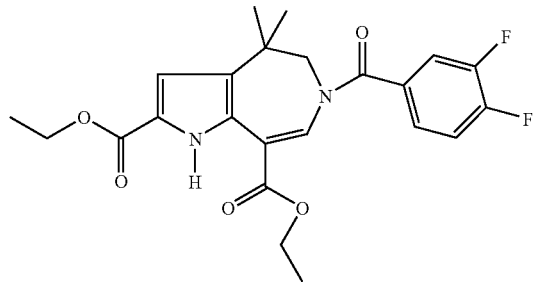 [SMILES: CCOC(=O)C1=CN(C(=O)c2ccc(F)c(F)c2)CC(C)(C)c2cc(C(=O)OCC)[nH]c21]

To a mixture of ethyl pyrrole-2-carboxylate (8.1 g, 58.3 mmol) and AlCl₃ (15.5 g, 2 equiv) in 1,2-dichloroethane-nitromethane (1:1, 120 ml) was added α,α,-dichloromethyl methyl ether (6.4 mL, 2 equiv) dropwise at −20° C. Stirring was continued for 1 h at −20° C. and the reaction mixture was stored at −20° C. overnight. It was then poured into ice. Organic layer was separated and aqueous layer was extracted with DCM. The combined organic layers were washed with water, aqueous NH₄OH and water and dried over Na₂SO₄. Evaporation of solvent afforded ethyl 4-formylpyrrole-2-carboxylate as a solid (8.8 g, 90%). ¹H-NMR(CDCl₃): δ 10.40 (1H, s), 8.95 (1H, s), 7.60 (1H, dd), 7.33 (1H, dd), 4.36 (2H, q), 1.39 (3H, t).

To a mixture of ethyl 4-formylpyrrole-2-carboxylate (8.8 g, 52.7 mmol) and dimethylamine (2 M in THF, 40 mL, 1.5 equiv) in methanol (60 mL) was added sodium cyanoborohydride (3.3 g, 1 equiv) in portions and the mixture was stirred for 3 h at 20° C. Water was added and the mixture was extracted with EtOAc. The combined organic layer was washed with water and dried over Na₂SO₄. Evaporation of solvent afforded a crude, which was purified by column chromatography on silica gel, eluted with MeOH-DCM (1:9) to afford ethyl 4-dimethylaminomethyl-pyrrole-2-carboxylate as a solid (7.8 g, 76%). MS (ES): 392 (MH⁺) 197.

To a solution of ethyl 4-dimethylaminomethyl-pyrrole-2-carboxylate (13.45 g, 68.6 mmol) in THF-DCM (1:1, 200 ml) was added MeI and the mixture was stirred for 1 h at 20° C. and stored in refrigerator overnight. Evaporation of solvent afforded a crude, which was used in next step without further purification.

To a solution of the above crude in ethanol (120 mL) was added sodium cyanide (3.4 g, 5 equiv) and the reaction mixture was heated to reflux for 80 h. After cooling, solvent was removed and the crude was dissolved in water and extracted with DCM. The combined organic layer was washed with water and dried over MgSO₄. Evaporation of solvent afforded ethyl 4-cyanomethylpyrrole-2-carboxylate as an oil (9.84 g, 81% for 2 steps). ¹H-NMR(CDCl₃): δ 9.30 (1H, s), 6.94 (1H, m), 6.86 (1H, d), 4.30 (2H, q), 3.60 (2H, s), 1.32 (3H, t).

To a mixture of ethyl 4-cyanomethylpyrrole-2-carboxylate (9.84 g, 55.3 mmol), di-tert-butyl dicarbonate (14.5 g, 1.2 equiv) and TEA (11.6 mL, 1.5 equiv) in DCM (250 mL) was added 4-dimethylaminopyridine (0.5 g, 4.4 mmol) and the reaction mixture was stirred for 1 h at 20° C. and then washed with 1 N HCl, water, saturated aqueous NaHCO₃, and water. After drying over Na₂SO4, solvent was evaporated to afford 4-(cyano-methylypyrrole-1,2-dicarboxylic acid 1-tert-butyl ester 2-ethyl ester as an oil (14.2 g). MS (ES): 392 (MH⁺) 279.

To a solution of 4-(cyanomethyl)-pyrrole-1,2-dicarboxylic acid 1-tert-butyl ester 2-ethyl ester (14.2 g, 51 mmol) and MeI (12.8 mL,4 equiv) in DMF (250 mL) was added NaH (6 g, 60%, 3 equiv) in portions at −50° C. Stirring was continued for 2 h at −5° C. The reaction mixture was quenched with brine and extracted with EtOAc three times. The combined organic layer was washed with brine and dried over MgSO₄. Evaporation of solvent afforded an oil, which was dissolved in a mixture of TFA-DCM (1:2, 150 mL) and stirring was continued for 1 h at 20° C. Solvent was removed and the crude was redissolved in DCM. It was then washed with saturated aqueous NaHCO₃. The aqueous layer was extracted with DCM. The combined organic layer was washed with brine and dried over MgSO₄. Evaporation of solvent afforded 4-(cyano-dimethyl-methyl)-pyrrole-2-carboxylic acid ethyl ester as an oil (10.2 g). MS (ES): 392 (MH⁺) 207.

To a solution of 4-(cyano-dimethyl-methyl)-pyrrole-2-carboxylic acid ethyl ester (10.2 g) in formic acid (80 mL) was added Raney nickel (prepared from Nickel-Aluminum alloy (1:1, 39 g)) and the suspension was heated to reflux under stirring for 1.5 h. Another portion of catalyst of the same amount was added and the mixture was refluxed for another 1.5 h. After cooling, catalyst was removed by filtration and washed with water and DCM. The aqueouslayer was separated and washed with DCM. 1 H HCl was added to the aqueous layer. Evaporation of water afforded 4-(2-amino-1,1-dimethyl-ethyl)-1-1H-pyrrole-2-carboxylic acid ethyl ester hydrochloric salt as a solid. MS (ES): (MH⁺ of the free base) 207.

4-(2-amino-1,1-dimethyl-ethyl)-1H-pyrrole-2-carboxylic acid ethyl ester hydrochloride salt was used in a manner similar to that described in Example 1 in the condensation reaction with ethyl 3-bromopyruvate to prepare 4,4-dimethyl-1,4,5,6-tetrahydro-pyrrolo[2,3-d]azepine-2,8-dicarboxylic acid diethyl ester. ¹H-NMR(CDCl₃): δ 11.05 (1H, s), 7.76 (1H, d), 6.80 (1H, m), 5.40 (1H, s), 4.26 (4H, m), 3.14 (2H, t), 1.30 (6H, m).

The title compound was prepared in a manner similar to that described in Example 2 by using 4,4-dimethyl-1,4,5,6-tetrahydro-pyrrolo[2,3-d]azepine-2,8-dicarboxylic acid diethyl ester and 3,4-difluoro-benzoyl chloride. $^1$H-NMR (CDCl$_3$): δ 11.11 (1H, s), 7.83 (1H, s), 7.48 (1H, m), 7.36 (1H, m), 6.87 (1H, d), 4.33 (2H, q), 4.24 (2H, q), 3.89 (2H, s), 1.36 (3H, t), 1.33 (6H, s), 1.22 (3H, t). MS (ES): 447 (MH$^+$).

EXAMPLE 14

Preparation of 6-(3,4-difluoro-benzoyl)-4,4-dimethyl-1,4,5,6-tetrahydro-pyrrolo[2,3-d]azepine-2,8-dicarboxylic acid 2-ethyl ester 8-isopropyl ester

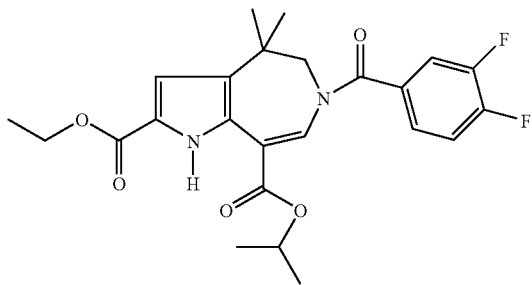

The title compound was prepared in a manner similar to that described in Example 13 by using iso-propyl 3-bromopyruvate in the condensation reaction with 4-(2-amino-1,1-dimethyl-ethyl)-1H-pyrrole-2-carboxylic acid ethyl ester hydrochloric salt to prepare 4,4-dimethyl-1,4,5,6-tetrahydro-pyrrolo[2,3-d]azepine-2,8-dicarboxylic acid 2ethyl ester 8-isopropyl ester. MS (ES): 321 (MH$^+$)

The title compound was prepared in a manner similar to that described in Example 2 by using 4,4-dimethyl-1,4,5,6-tetrahydro-pyrrolo[2,3-d]azepine-2,8-dicarboxylic acid 2-ethyl ester 8-isopropyl ester and 3,4-difluoro-benzoyl chloride. $^1$H-NMR(CDCl$_3$): δ 11.11 (1H, s), 7.83 (1H, s), 7.48 (1H, m), 7.27 (1H, m), 6.87 (1H, d), 5.10 (1H, m), 4.33 (2H, q), 3.92 (2H, s), 1.37 (3H, t), 1.33 (6H, s), 1.21 (6H, d). MS (ES): 461 (MH$^+$).

EXAMPLE 15

Preparation of 6-(3,4-difluoro-benzoyl)-1,4,4-trimethyl-1,4,5,6-tetrahydro-pyrrolo[2,3-d]azepine-2,8-dicarboxylic acid 2-ethyl ester 8-isopropyl ester

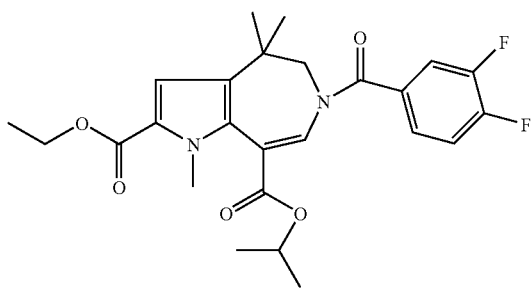 [SMILES: CCOC(=O)c1cc2c(n1C)C(C(=O)OC(C)C)=CN(C(=O)c1ccc(F)c(F)c1)CC2(C)C]

On one occasion, 4(cyano-dimethyl-methyl)-1-methyl-pyrrole-2-carboxylic acid ethyl ester was obtained as a by-product when 4-(cyano-dimethyl-methyl)-pyrrole-2-carboxylic acid ethyl ester was prepared, this mixture was carried on to the following reactions until the preparation of 4,4-dimethyl-1,4,5,6-tetrahydro-pyrrolo[2,3-d]azepine-2,8-dicarboxylic acid 2-ethyl ester 8-isopropyl ester as described in Example 13. At this point, 1,4,4-trimethyl-1,4,5,6-tetrahydro-pyrrolo[2,3-d]azepine-2,8-dicarboxylic acid 2-ethyl ester 8-isopropyl ester was isolated from the mixture. MS (ES): 335 (MH$^+$).

The title compound was prepared in a manner similar to that described in Example 2 by using 1,4,4-trimethyl-1,4,5,6-tetrahydro-pyrrolo[2,3-d]azepine-2,8-dicarboxylic acid 2-ethyl ester 8-isopropyl ester and 3,4-difluoro-benzoyl chloride. $^1$H-NMR(CDCl$_3$): δ 7.75 (1H, s), 7.43 (1H, m), 7.28 (2H, m), 6.86 (1H, d), 5.06 (1H, m), 4.28 (2H, q), 3.87 (2H, s), 3.66 (3H, s), 1.35 (3H, 3), 1.33 (6H, s), 1.21 (6H, d). MS (ES): 475 (MH$^+$).

EXAMPLE 16

Time Resolved Fluoroscence Resonance Energy Transfer (TR-FRET) Assay

The TR-FRET assay was performed by incubating 8 nM of GST-farnesoid X receptor -LBD (comprising glutathione-S-transferase fused in frame to the farnesoid X receptor ligand binding domain, (amino acids 244-471 of the human farnesoid X receptor)), 8 nM of Europium-labeled anti-GST antibody (Wallac/PE Life Sciences Cat#AD0064),16 nM biotin-SRC-1 peptide [5'-biotin-CPSSHSSLTERHKILHRLLQEGSPS-CONH2], 20 nM APC-SA [allophycocyanin conjugated streptavidin] (Wallac/PE Life Sciences, Cat# AD0059A) in FRET assay buffer (20 mM KH$_2$PO$_4$/K$_2$HPO$_4$ (pH 7.3),150 mM NaCl, 2 mM CHAPS, 2 mM EDTA, 1 mM DTT) in the presence of the test compound(s) for 2-4 hours at room temperature in a 384 well assay plate. Data was collected using an LJL Analyst using the standard operating instructions and conditions with readings at emission wavelengths of 615 nm and 665 nm after a delay of 65 μs and an excitation wavelength of 330 nm.

EXAMPLE 17

Co-Transfection Assay

The basic co-transfection protocol for measuring the farnesoid X receptor activity is as follows. CV-1 African Green Monkey Kidney cells were plated 24 hours before transfection to achieve approximately 70-80 percent confluency. Cells were transfected with the following expression vectors, CMX-farnesoid X receptor (full length human farnesoid X receptor), CMX-RXRα (full length human RXR), Luc12 ((ECREx7-Tk-Luciferase) luciferase reporter gene construct. (See WO 00/76523, Venkateswaran et al., (2000) J. Biol. Chem. 275 14700-14707). A CMX-β-Galactosidase expression vector was used as a transfection control. The transfection reagent used was DOTAP (Boehringer Mannheim). Cells were incubated with the DOTAP/DNA mixture for 5 hours after which the cells were harvested and plated onto either 96 well or 384 well plates containing the appropriate concentration of test compound. The assay was allowed to continue for an additional 18-20 hours, after which the cells were lysed, with lysis buffer (1% triton X 100, 10% glycerol, 5 mM Dithiothreitol, 1 mM EGTA, 25 mM Tricine, pH 7.8) and the luciferase activity measured in the presence of Luciferase assay buffer (0.73 mM ATP, 22.3 mM Tricine, 0.11 mM EGTA, 0.55 mM Luciferin, 0.15 mM Coenzyme A, 0.5 mM HEPES, 10 mM Magnesium sulphate) on a standard luminomter plate reader (PE Biosystems, NorthStar Reader), using recommended operating instructions and conditions.

RESULTS OF EXAMPLE 18 AND 19

Both the farnesoid X receptor/ECREx7 co-transfection assay (Example 10) and the TR-FRET assay (Example 9) can be used to establish the $EC_{50}/IC_{50}$ values for potency and percent activity or inhibition for efficacy. Efficacy defines the activity of a compound relative to a high control (chenodeoxycholic acid, CDCA) or a low control (DMSO/vehicle). The dose response curves are generated from an 8 point curve with concentrations differing by ½ LOG units. Each point represents the average of 4 wells of data from a 384 well plate. The curve for the data is generated by using the equation:

$$Y=\text{Bottom}+(\text{Top}-\text{Bottom})/(1+10^{((\log EC50-X)*HillSlope)})$$

The $EC_{50}/IC_{50}$ is therefore defined as the concentration at which an agonist or antagonist elicits a response that is half way between the Top (maximum) and Bottom (baseline) values. The $EC_{50}/IC_{50}$ values represented are the averages of at least 3 independent experiments. The determination of the relative efficacy or % control for an agonist is by comparison to the maximum response achieved by chenodeoxycholic acid that is measured individually in each dose response experiment.

For the antagonist assay, CDCA is added to each well of a 384 well plate to elicit a response. The % inhibition for each antagonist is therefore a measurement of the inhibition of the activity of CDCA. In this example, 100% inhibition would indicate that the activity of CDCA has been reduced to baseline levels, defined as the activity of the assay in the presence of DMSO only.

Most of the compounds disclosed herein and tested exhibited activity in at least one of the above assays ($EC_{50}$ or $IC_{50}$ less than 10 µM). Most showed activity at or below 1 µM. For example, the following compound exhibited agonist activity at or less than 1 µM $EC_{50}$ with greater than 100% efficacy as measured via the co-transfection assay:

3-(4-Fluoro-benzoyl)-1,2,3,6,7,8,9,10-octahydro-azepino[4,5-b]indole-5-carboxylic acid ethyl ester.

The following compound exhibited agonist activity at or less than 100 nM $EC_{50}$ with greater than 100% efficacy as measured via the co-transfection assay:

3-(4-Fluoro-benzoyl)-1,1-dimethyl-1,2,3,4,5,6,7,8,9,10-decahydro-azepino[4,5-b]indole-5-carboxylic acid ethyl ester;

3-(4-Fluoro-benzoyl)-1,1-dimethyl-1,2,3,6,7,8,9,10-octahydro-azepino[4,5-b]indole-5-carboxylic acid ethyl ester;

6-(3,4-Difluoro-benzoyl)-4,4-dimethyl-5,6-dihydro-4H-thieno[2,3-d]azepine-8-carboxylic acid ethyl ester;

6-(3,4-Difluoro-benzoyl)-4,4-dimethyl-1,4,5,6-tetrahydro-pyrrolo[2,3-d]azepine-2,8-dicarboxylic acid diethyl ester;

6-(3,4-Difluoro-benzoyl)-4,4-dimethyl-1,4,5,6-tetrahydro-pyrrolo[2,3-d]azepine-2,8-dicarboxylic acid 2-ethyl ester 8-isopropyl ester; and 6-(3,4-Difluoro-benzoyl)-1,4,4-trimethyl-1,4,5,6-tetrahydro-pyrrolo[2,3-d]azepine-2,8-dicarboxylic acid 2-ethyl ester 8-isopropyl ester.

Since modifications will be apparent to those of skill in this art, it is intended that this invention be limited only by the scope of the appended claims.

What is claimed is:
1. A compound having the formula (I):

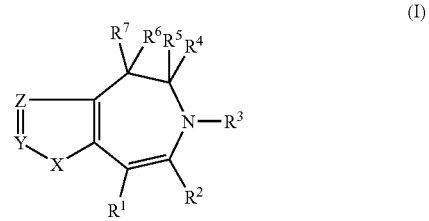

wherein:
X is $NR^9$, or S;
Y is $CR^{30}$;
Z is $CR^{31}$ or N;
$R^{30}$ and $R^{31}$ are each independently selected from the group consisting of halo, hydrogen, optionally substituted alkyl, optionally substituted alkenyl, optionally substituted alkynyl, optionally substituted aryl, optionally substituted heteroaryl, optionally substituted cycloalkyl, optionally substituted cycloalkylalkyl, optionally substituted heterocyclyl, optionally substituted heterocyclylalkyl, optionally substituted aralkyl, optionally substituted heteroaralkyl, —$OR^{32}$, —$SR^{32}$, —$N(R^{33})R^{34}$, —$N(R^{33})S(O)_2R^{23}$; —$N(R^{35})N(R^{33})R^{34}$, —$N(R^{35})N(R^{33})S(O)_2R^{23}$, —$C(O)R^{36}$, —$C(O)OR^{32}$, —$C(S)OR^{32}$, —$C(O)SR^{32}$, —$C(O)N(R^{33})R^{34}$, —$C(S)N(R^{33})R^{34}$, —$C(O)N(R^{33})S(O)_2R^{23}$, —$C(S)N(R^{33})S(O)_2R^{23}$, —$C(O)N(R^{35})N(R^{33})R^{34}$, —$C(S)N(R^{35})N(R^{33})R^{34}$ and —$C(O)N(R^{35})N(R^{33})S(O)_2R^{23}$; or
$R^{30}$ and $R^{31}$ together with the carbon atoms to which they are attached, form an optionally substituted cycloalkyl ring, or optionally substituted nonaromatic cycloalkenyl ring;
$R^{32}$, $R^{33}$, $R^{34}$, $R^{35}$ and $R^{36}$ are selected as in (a) or (b) as follows: (a) $R^{32}$, $R^{33}$, $R^{34}$, $R^{35}$ and $R^{36}$ are each independently hydrogen, optionally substituted alkyl, optionally substituted alkenyl, optionally substituted alkynyl, optionally substituted cycloalkyl, optionally substituted aryl, optionally substituted aralkyl, optionally substituted heterocyclyl, optionally substituted heteroaryl, or optionally substituted heteroaralkyl; or (b) $R^{33}$ and $R^{34}$, together with the nitrogen atom to which they are attached, form an optionally substituted heterocyclyl ring, or an optionally substituted heteroaryl ring, and $R^{32}$, $R^{35}$ and $R^{36}$ are selected as in (a) above,
$R^1$ is selected from a group consisting of —$OR^{41}$, —$SR^{14}$, —$N(R^{15})R^{16}$, —$N(R^{15})S(O)_2R^{23}$; —$N(R^{17})N(R^{15})R^{16}$, —$N(R^{17})N(R^{15})S(O)_2R^{23}$, —$C(O)R^{18}$, —$C(O)R^{14}$, —$C(S)OR^{14}$, —$C(O)SR^{14}$, —$C(O)N(R^{15})R^{16}$, —$C(O)N(R^{15})S(O)_2R^{23}$, —$C(O)N(R^{15})N=R^{16}$, —$C(O)N(R^{17})N(R^{15})R^{16}$ and —$C(O)N(R^{17})N(R^{15})S(O)_2R^{23}$;
$R^2$ is hydrogen;
$R^3$ is hydrogen, —$C(O)R^{10}$, —$C(O)OR^{10}$, —$S(O)_2R^{10}$, —$C(O)N(R^{11})R^{12}$, —$C(O)N(R^{11})S(O)_2R^{23}$, —$C(O)N(R^{13})N(R^{11})R^{12}$, —$C(O)N(R^{11})S(O)_2R^{23}$, —$N(R^{13})C(O)R^{10}$, —$N(R^{13})C(O)N(R^{11})R^{12}$, —$N(R^{13})C(O)N(R^{11})S(O)_2R^{23}$, —$N(R^{10}C(O)N(R^{13})N(R^{11})R^{12}$, —$N(R^{10})C(O)N(R^{13})N(R^{11})S(O)_2R^{23}$, —$N(R^{13})C(O)OR^{10}$, —$P(O)OR^{10}$, or —$P(O)(OR^{19})OR^{12}$;
$R^4$, $R^5$, $R^6$ and $R^7$ are each independently selected from a group consisting of hydrogen, halo, optionally substituted alkyl, optionally substituted alkenyl, or optionally substituted alkynyl;

$R^9$ is hydrogen, or optionally substituted alkyl;

$R^{10}$, $R^{11}$, $R^{12}$, $R^{13}$ and $R^{19}$ are selected as in (a) or (b) as follows: (a) $R^{10}$, $R^{11}$, $R^{12}$, $R^{13}$ and $R^{19}$ each independently hydrogen, optionally substituted alkyl, optionally substituted alkenyl, optionally substituted alkynyl, optionally substituted cycloalkyl, optionally substituted aryl, optionally substituted aralkyl, optionally substituted heterocyclyl, optionally substituted heteroaryl, or optionally substituted heteroaralkyl; or (b) $R^{11}$ and $R^{12}$ or $R^{12}$ and $R^{19}$, together with the atoms to which they are attached, form an optionally substituted heterocyclyl ring or an optionally substituted heteroaryl ring; and the others of $R^{10}$, $R^{11}$, $R^{12}$, $R^{13}$ and $R^{19}$ are selected as in (a), above;

$R^{14}$, $R^{15}$, $R^{16}$, $R^{17}$ and $R^{18}$ are selected as in (a) or (b) as follows: (a) $R^{14}$, $R^{15}$, $R^{16}$, $R^{17}$ and $R^{18}$ are each independently hydrogen, optionally substituted alkyl, optionally substituted alkenyl, optionally substituted alkynyl, optionally substituted cycloalkyl, optionally substituted aryl, optionally substituted aralkyl, optionally substituted heterocyclyl, optionally substituted heteroaryl, or optionally substituted heteroaralkyl; or (b) $R^{15}$ and $R^{16}$, together with the nitrogen atom to which they are attached, form an optionally substituted heterocyclyl ring, or an optionally substituted heteroaryl ring, and $R^{14}$, $R^{17}$ and $R^{18}$ are selected as in (a) above;

$R^{23}$ is optionally substituted alkyl, optionally substituted alkenyl, optionally substituted alkynyl, optionally substituted cycloalkyl, optionally substituted aryl, optionally substituted aralkyl, optionally substituted heterocyclyl, optionally substituted heteroaryl, or optionally substituted heteroaralkyl;

each of $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, and $R^{30}$, $R^{31}$, $R^{32}$, $R^{33}$, $R^{34}$, $R^{35}$ and $R^{36}$, when substituted, are substituted with one or more substituents, each independently selected from $Q^1$;

each $Q^1$ is independently selected from halo, pseudohalo, oxo, thioxo, cyano, thiocyano, isocyano, nitro, azido, alkyl, haloalkyl, alkenyl containing 1 to 2 double bonds, alkynyl containing 1 to 2 triple bonds, cycloalkyl, cycloalkenyl, cycloalkynyl, cycloalkylalkyl, heterocyclyl, heterocyclylalkyl, aryl, heteroaryl, aralkyl, aralkenyl, aralkynyl, heteroarylalkyl, alkylidene, arylalkylidene, aryloxyarylcarbonylamino, hydroxycarbonylalkylthio, halosulfonyl, —$OR^{70}$, —$SR^{70}$, —$R^{60}$—$C(J)R^{71}$, —$R^{60}$—$N(R^{70})C(J)R^{71}$, —$OC(O)R^{71}$, —$R^{60}$—$N(R^{75})(R^{76})$, —$P(R^{78})_2$, —$P(O)(R^{78})_2$, —$OP(O)(R^{78})_2$, —$N(R^{70})S(O)_2R^{71}$, —$S(O)_2R^{71}$, —$S(O)R^{82}$, —$OS(O)R^{83}$, —$OS(O)_2R^{83}$ or —$Si(R^{83})_3$;

two $Q^1$ groups, which substitute atoms in a 1,2 or 1,3 arrangement, together with the carbon atoms to which they are attached form a cycloalkyl ring, cycloalkenyl ring, cycloalkynyl ring or heterocyclyl ring; or each $Q^1$ is independently substituted or unsubstituted with one or more substituents each independently selected from $Q^2$;

each $Q^2$ is independently selected from halo, pseudohalo, oxo, thioxo, cyano, thiocyano, isocyano, nitro, azido, alkyl, haloalkyl, alkenyl containing 1 to 2 double bonds, alkynyl containing 1 to 2 triple bonds, cycloalkyl, cycloalkenyl, cycloalkynyl, cycloalkylalkyl, heterocyclyl, heterocyclylalkyl, aryl, heteroaryl, aralkyl, aralkenyl, aralkynyl, heteroarylalkyl, alkylidene, arylalkylidene, aryloxyarylcarbonylamino, hydroxycarbonylalkylthio, halosulfonyl, —$OR^{70}$, —$SR^{70}$, —$R^{60}$—$C(J)R^{71}$, —$R^{60}$—$N(R^{70})C(J)R^{71}$, —$OC(O)R^{71}$, —$R^{60}$—$N(R^{75})(R^{76})$, —$P(R^{78})_2$, —$P(O)(R^{78})_2$, —$OP(O)(R^{78})_2$, —$N(R^{70})S(O)_2R^{71}$, —$S(O)_2R^{71}$, —$S(O)R^{82}$, —$OS(O)R^{83}$, —$OS(O)_2R^{83}$ or —$Si(R^{83})_3$;

two $Q^2$ groups, which substitute atoms in a 1,2 or 1,3 arrangement, together with the carbon atoms to which they are attached form a cycloalkyl ring, cycloalkenyl ring, cycloalkynyl ring or heterocyclyl ring;

each J is independently O, S or —$NR^{70}$;

each $R^{60}$ is independently a direct bond or alkylene;

each $R^{70}$ is independently hydrogen, alkyl, alkenyl, alkynyl, cycloalkyl, heterocyclyl, aryl, heteroaryl, aralkyl, haloalkyl, heterocyclylalkyl or heteroaralkyl;

each $R^{71}$ is independently hydrogen, alkyl, alkenyl, alkynyl, cycloalkyl, heterocyclyl, aryl, heteroaryl, aralkyl, haloalkyl, heterocyclylalkyl, heteroaralkyl, —$OR^{72}$ or —$N(R^{73})R^{74}$;

$R^{72}$, $R^{73}$ and $R^{74}$ are each independently hydrogen, alkyl, alkenyl, alkynyl, cycloalkyl, heterocyclyl, aryl, heteroaryl, aralkyl or heteroaralkyl; or $R^{73}$ and $R^{74}$, together with the nitrogen atom to which they are attached, form a heterocyclyl ring or heteroaryl ring;

$R^{75}$ and $R^{76}$ are each independently hydrogen, alkyl, alkenyl, alkynyl, aryl, aralkyl, heteroaryl, heteroaralkyl, heterocyclyl or heterocyclylalkyl; or $R^{75}$ and $R^{76}$, together with the nitrogen atom to which they are attached, form a heterocyclyl ring or heteroaryl ring;

$R^{78}$ is alkyl, heteroaryl, heterocyclyl, aryl, —$OR^{79}$ or —$N(R^{80})R^{81}$;

$R^{79}$ is hydrogen, alkyl, alkenyl, cycloalkyl, heterocyclyl, aryl, heteroaryl, aralkyl or heteroaralkyl;

$R^{80}$ and $R^{81}$ are each independently hydrogen, alkyl, alkenyl, alkynyl, cycloalkyl, heterocyclyl, aryl, heteroaryl, aralkyl or heteroaralkyl; or $R^{80}$ and $R^{81}$, together with the nitrogen atom to which they are attached, form a heterocyclyl ring or heteroaryl ring;

$R^{82}$ is alkyl, alkenyl, cycloalkyl, heterocyclyl, aryl, heteroaryl, aralkyl, heteroaralkyl or —$OR^{83}$; and each $R^{83}$ is independently alkyl, alkenyl, cycloalkyl, heterocyclyl, aryl, heteroaryl, aralkyl or heteroaralkyl;

as a single isomer, a mixture of isomers, or as a racemic mixture of isomers; or as a pharmaceutically acceptable salt thereof.

2. A compound of claim 1, wherein:

$R^1$ is —$C(O)OR^{14}$ or —$C(O)N(R^{15})R^{16}$.

3. The compound of claim 2, wherein $R^3$ is —$C(O)R^{10}$, —$C(O)OR^{10}$, —$S(O)_2R^{10}$ or —$C(O)N(R^{11})R^{12}$.

4. The compound of claim 3 wherein $R^4$, $R^5$, $R^6$ and $R^7$ are selected from a), b), c), and d) below:

a) $R^4$ and $R^5$ are each independently hydrogen or halo and $R^6$ and $R^7$ are optionally substituted alkyl;

b) $R^6$ and $R^7$ are each independently hydrogen or halo and $R^4$ and $R^5$ are optionally substituted alkyl;

c) $R^4$, $R^5$, $R^6$ and $R^7$ are each optionally substituted alkyl; and d) $R^4$, $R^5$, $R^6$ and $R^7$ are each independently hydrogen or halo.

5. A compound of claim 1 having the formula (II):

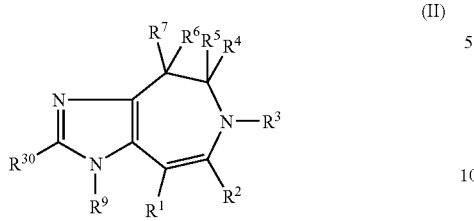

or a pharmaceutically acceptable salt thereof, wherein:
$R^1$ is —C(O)OR$^{14}$, or —C(O)N(R$^{15}$)R$^{16}$;
$R^2$ is hydrogen;
$R^3$ is —C(O)R$^{10}$;
$R^4$ and $R^5$ are each independently hydrogen or halo; or
$R^4$ and $R^5$ are each optionally substituted alkyl;
$R^6$ and $R^7$ are each independently hydrogen or halo; or
$R^6$ and $R^7$ are each optionally substituted alkyl; or
$R^9$ is hydrogen, or optionally substituted alkyl;
$R^{10}$ is an optionally substituted aryl or an optionally substituted heteroaryl;
$R^{14}$, $R^{15}$, $R^{16}$, $R^{17}$ and $R^{18}$ are each independently hydrogen, optionally substituted alkyl, optionally substituted alkenyl, optionally substituted alkynyl, optionally substituted cycloalkyl, optionally substituted aryl, optionally substituted aralkyl, optionally substituted heterocyclyl, optionally substituted heteroaryl, or optionally substituted heteroaralkyl;
$R^{23}$ is optionally substituted alkyl, optionally substituted alkenyl, optionally substituted alkynyl, optionally substituted cycloalkyl, optionally substituted aryl, optionally substituted aralkyl, optionally substituted heterocyclyl, optionally substituted heteroaryl, or optionally substituted heteroaralkyl; and
$R^{30}$ is halo, hydrogen, optionally substituted alkyl, optionally substituted alkenyl, optionally substituted alkynyl, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl, optionally substituted heteroaralkyl, —OR$^{32}$, —SR$^{32}$, —N(R$^{33}$)R$^{34}$, —N(R$^{33}$)S(O)$_2$R$^{23}$; —N(R$^{35}$)N(R$^{33}$)R$^{34}$, —N(R$^{35}$)N(R$^{33}$)S(O)$_2$R$^{23}$, —C(O)R$^{36}$, —C(O)OR$^{32}$, —C(S)OR$^{32}$, —C(O)SR$^{32}$, —C(O)N(R$^{33}$)R$^{34}$, —C(S)N(R$^{33}$)R$^{34}$, —C(O)N(R$^{33}$)S(O)$_2$R$^{23}$, —C(S)N(R$^{33}$)S(O)$_2$R$^{23}$, —C(O)N(R$^{35}$)N(R$^{33}$)R$^{34}$, —C(S)N(R$^{35}$)N(R$^{33}$)R$^{34}$ or —C(O)N(R$^{35}$)N(R$^{33}$)S(O)$_2$R$^{23}$.

6. The compound of claim 5 wherein:
$R^4$, $R^5$, $R^6$ and $R^7$ are each independently hydrogen or halo; and
$R^{30}$ is selected from the group consisting of hydrogen, halo, —C(O)R$^{36}$, —C(O)OR$^{32}$, —C(S)OR$^{32}$, —C(O)SR$^{32}$, —C(O)N(R$^{33}$)R$^{34}$, —C(S)N(R$^{33}$)R$^{34}$, —C(O)N(R$^{33}$)S(O)$_2$R$^{23}$, —C(S)N(R$^{33}$)S(O)$_2$R$^{23}$, —C(O)N(R$^{35}$)N(R$^{33}$)R$^{34}$, —C(S)N(R$^{35}$)N(R$^{33}$)R$^{34}$ and —C(O)N(R$^{35}$)N(R$^{33}$)S(O)$_2$R$^{23}$;
where $R^{23}$ is optionally substituted alkyl, optionally substituted alkenyl, optionally substituted alkynyl, optionally substituted cycloalkyl, optionally substituted aryl, optionally substituted aralkyl, optionally substituted heterocyclyl, optionally substituted heteroaryl, or optionally substituted heteroaralkyl; and where $R^{32}$, $R^{33}$, $R^{34}$, $R^{35}$ and $R^{36}$ are selected as in (a) or (b) as follows: (a) $R^{32}$, $R^{33}$, $R^{34}$, $R^{35}$ and $R^{36}$ are each independently hydrogen, optionally substituted alkyl, optionally substituted alkenyl, optionally substituted alkynyl, optionally substituted cycloalkyl, optionally substituted aryl, optionally substituted aralkyl, optionally substituted heterocyclyl, optionally substituted heteroaryl, or optionally substituted heteroaralkyl; or (b) $R^{33}$ and $R^{34}$, together with the nitrogen atom to which they are attached, form an optionally substituted heterocyclyl ring, or an optionally substituted heteroaryl ring, and the others of $R^{32}$, $R^{35}$ and $R^{36}$ are selected as in (a) above.

7. The compound of claim 6 wherein said compound is 6-(4-fluoro-benzoyl)-3,6,7,8-tetrahydro-imidazo[4,5-d]azepine-4-carboxylic acid ethyl ester.

8. The compound of claim 5 wherein:
$R^4$ and $R^5$ are each independently hydrogen or halo; and
$R^6$ and $R^7$ are optionally substituted alkyl.

9. The compound of claim 8 wherein
$R^9$ is hydrogen.

10. The compound of claim 9 wherein $R^{30}$ is selected from the group consisting of —C(O)R$^{36}$, —C(O)OR$^{32}$, —C(S)OR$^{32}$, —C(O)SR$^{32}$, —C(O)N(R$^{33}$)R$^{34}$, —C(S)N(R$^{33}$)R$^{34}$, —C(O)N(R$^{33}$)S(O)$_2$R$^{23}$, —C(S)N(R$^{33}$)S(O)$_2$R$^{23}$, —C(O)N(R$^{35}$)N(R$^{33}$)R$^{34}$, —C(S)N(R$^{35}$)N(R$^{33}$)R$^{34}$ and —C(O)N(R$^{35}$)N(R$^{33}$)S(O)$_2$R$^{23}$;
where $R^{23}$ is optionally substituted alkyl, optionally substituted alkenyl, optionally substituted alkynyl, optionally substituted cycloalkyl, optionally substituted aryl, optionally substituted aralkyl, optionally substituted heterocyclyl, optionally substituted heteroaryl, or optionally substituted heteroaralkyl; and
where $R^{32}$, $R^{33}$, $R^{34}$, $R^{35}$ and $R^{36}$ are selected as in (a) or (b) as follows: (a) $R^{32}$, $R^{33}$, $R^{34}$, $R^{35}$ and $R^{36}$ are each independently hydrogen, optionally substituted alkyl, optionally substituted alkenyl, optionally substituted alkynyl, optionally substituted cycloalkyl, optionally substituted aryl, optionally substituted aralkyl, optionally substituted heterocyclyl, optionally substituted heteroaryl, or optionally substituted heteroaralkyl; or (b) $R^{33}$ and $R^{34}$, together with the nitrogen atom to which they are attached, form an optionally substituted heterocyclyl ring, or an optionally substituted heteroaryl ring, and the others of $R^{32}$, $R^{35}$ and $R^{36}$ are selected as in (a) above.

11. The compound of claim 10 wherein $R^1$ is —C(O)OCH$_2$CH$_3$, —C(O)OCH$_3$, —C(O)OCH(CH$_3$)$_2$, —C(O)OH, —C(O)OCH$_2$CH$_2$CH$_3$, —C(O)NHCH$_3$, —C(O)NHCH$_2$CH$_3$, —C(O)NHCH (CH$_3$)$_2$, —C(O)NH(cyclopropyl), —C(O)NH(cyclopentyl), —C(O)NHCH(CH$_3$)(CH$_2$CH$_3$) or —C(O)N(CH$_3$)(cyclopropyl).

12. The compound of claim 4 wherein:
Z is CR$^{31}$; and
$R^{31}$ is independently selected from a group consisting of halo, hydrogen, optionally substituted alkyl, optionally substituted alkenyl, optionally substituted alkynyl, optionally substituted cycloalkyl, optionally substituted cycloalkylalkyl, optionally substituted heterocyclyl, optionally substituted heterocyclylalkyl, optionally substituted aryl, optionally substituted aralkyl, optionally substituted heteroaryl, optionally substituted heteroaralkyl, —OR$^{32}$, —SR$^{32}$, —N(R$^{33}$)R$^{34}$, —N(R$^{33}$)S(O)$_2$R$^{23}$; —N(R$^{35}$)N(R$^{33}$)R$^{34}$, —N(R$^{35}$)N(R$^{33}$)S(O)$_2$R$^{23}$, —C(O)R$^{36}$, —C(O)OR$^{32}$, —C(S)OR$^{32}$, —C(O)SR $^{32}$, —C(O)N(R$^{33}$)R$^{34}$, —C(S)N(R$^{33}$)R$^{34}$, —C(O)N(R$^{33}$)S(O)$_2$R$^{23}$, —C(S)N(R$^{33}$)S(O)$_2$R$^{23}$, —C(O)N(R$^{35}$)N(R$^{33}$)R$^{34}$, —C(S)N(R$^{35}$)N(R$^{33}$)R$^{34}$ and —C(O)N(R$^{35}$)N(R$^{33}$)S(O)$_2$R$^{23}$;

where R$^{23}$ is optionally substituted alkyl, optionally substituted alkenyl, optionally substituted alkynyl, optionally substituted cycloalkyl, optionally substituted aryl, optionally substituted aralkyl, optionally substituted heterocyclyl, optionally substituted heteroaryl, or optionally substituted heteroaralkyl; and where R$^{32}$, R$^{33}$, R$^{34}$, R$^{35}$ and R$^{36}$ are selected as in (a) or (b) as follows: (a) R$^{32}$, R$^{33}$, R$^{34}$, R$^{35}$ and R$^{36}$ are each independently hydrogen, optionally substituted alkyl, optionally substituted alkenyl, optionally substituted alkynyl, optionally substituted cycloalkyl, optionally substituted aryl, optionally substituted aralkyl, optionally substituted heterocyclyl, optionally substituted heteroaryl, or optionally substituted heteroaralkyl; or (b) R$^{33}$ and R$^{34}$, together with the nitrogen atom to which they are attached, form an optionally substituted heterocyclyl ring, or an optionally substituted heteroaryl ring, and the others of R$^{32}$, R$^{35}$ and R$^{36}$ are selected as in (a) above.

13. The compound of claim 12 wherein:
Z is CR$^{31}$; and
R$^{31}$ is independently selected from a group consisting of optionally substituted aryl, optionally substituted aralkyl, optionally substituted heteroaryl, optionally substituted heteroaralkyl, optionally substituted cycloalkyl, optionally substituted heterocyclyl, —C(O)R$^{36}$, —C(O)OR$^{32}$, —C(S)OR$^{32}$, —C(O)SR$^{32}$, —C(O)N(R$^{33}$)R$^{34}$, —C(S)N(R$^{33}$)R$^{34}$, —C(O)N(R$^{33}$)S(O)$_2$R$^{23}$, —C(S)N(R$^{33}$)S(O)$_2$R$^{23}$, —C(O)N(R$^{35}$)N(R$^{33}$)R$^{34}$, —C(S)N(R$^{35}$)N(R$^{33}$)R$^{34}$ and —C(O)N(R$^{35}$)N(R$^{33}$)S(O)$_2$R$^{23}$;

where R$^{23}$ is optionally substituted alkyl, optionally substituted alkenyl, optionally substituted alkynyl, optionally substituted cycloalkyl, optionally substituted aryl, optionally substituted aralkyl, optionally substituted heterocyclyl, optionally substituted heteroaryl, or optionally substituted heteroaralkyl; and where R$^{32}$, R$^{33}$, R$^{34}$, R$^{35}$ and R$^{36}$ are selected as in (a) or (b) as follows: (a) R$^{32}$, R$^{33}$, R$^{34}$, R$^{35}$ and R$^{36}$ are each independently hydrogen, optionally substituted alkyl, optionally substituted alkenyl, optionally substituted alkynyl, optionally substituted cycloalkyl, optionally substituted aryl, optionally substituted aralkyl, optionally substituted heterocyclyl, optionally substituted heteroaryl, or optionally substituted heteroaralkyl; or (b) R$^{33}$ and R$^{34}$, together with the nitrogen atom to which they are attached, form an optionally substituted heterocyclyl ring, or an optionally substituted heteroaryl ring, and the others of R$^{32}$, R$^{35}$ and R$^{36}$ are selected as in (a) above.

14. The compound of claim 12 wherein X is S.

15. The compound of claim 14 wherein R$^4$, R$^5$, R$^6$ and R$^7$ are each independently hydrogen or halo; and
R$^{30}$ is selected from the group consisting of hydrogen, halo, —C(O)R$^{36}$, —C(O)OR$^{32}$, —C(S)OR$^{32}$, —C(O)SR$^{32}$, —C(O)N(R$^{33}$)R$^{34}$, —C(S)N(R$^{33}$)R$^{34}$, —C(O)N(R$^{33}$)S(O)$_2$R$^{23}$, —C(S)N(R$^{33}$)S(O)$_2$R$^{23}$, —C(O)N(R$^{35}$)N(R$^{33}$)R$^{34}$, —C(S)N(R$^{35}$)N(R$^{33}$)R$^{34}$ and —C(O)N(R$^{35}$)N(R$^{33}$)S(O)$_2$R$^{23}$;

where R$^{23}$ is optionally substituted alkyl, optionally substituted alkenyl, optionally substituted alkynyl, optionally substituted cycloalkyl, optionally substituted aryl, optionally substituted aralkyl, optionally substituted heterocyclyl, optionally substituted heteroaryl, or optionally substituted heteroaralkyl; and where R$^{32}$, R$^{33}$, R$^{34}$, R$^{35}$ and R$^{36}$ are selected as in (a) or (b) as follows: (a) R$^{32}$, R$^{33}$, R$^{34}$, R$^{35}$ and R$^{36}$ are each independently hydrogen, optionally substituted alkyl, optionally substituted alkenyl, optionally substituted alkynyl, optionally substituted cycloalkyl, optionally substituted aryl, optionally substituted aralkyl, optionally substituted heterocyclyl, optionally substituted heteroaryl, or optionally substituted heteroaralkyl; or (b) R$^{33}$ and R$^{34}$, together with the nitrogen atom to which they are attached, form an optionally substituted heterocyclyl ring, or an optionally substituted heteroaryl ring, and the others of R$^{32}$, R$^{35}$ and R$^{36}$ are selected as in (a) above.

16. The compound of claim 1 wherein said compound is 6-(3,4-difluoro-benzoyl)-5,6-dihydro-4H-thieno[2,3-d]azepine-8-carboxylic acid ethyl ester.

17. The compound of claim 14 wherein:
R$^4$ and R$^5$ are each independently hydrogen or halo; and
R$^6$ and R$^7$ are optionally substituted alkyl.

18. The compound of claim 17 wherein:
R$^9$ is hydrogen.

19. The compound of claim 18 wherein R$^{30}$ is selected from the group consisting of —C(O)R$^{36}$, —C(O)OR$^{32}$, —C(S)OR$^{32}$, —C(O)SR$^{32}$, —C(O)N(R$^{33}$)R$^{34}$, —C(S)N(R$^{33}$)R$^{34}$, —C(O)N(R$^{33}$)S(O)$_2$R$^{23}$, —C(S)N(R$^{33}$)S(O)$_2$R$^{23}$, —C(O)N(R$^{35}$)N(R$^{33}$)R$^{34}$, —C(S)N(R$^{35}$)N(R$^{33}$)R$^{34}$ and —C(O)N(R$^{35}$)N(R$^{33}$)S(O)$_2$R$^{23}$;

where R$^{23}$ is optionally substituted alkyl, optionally substituted alkenyl, optionally substituted alkynyl, optionally substituted cycloalkyl, optionally substituted aryl, optionally substituted aralkyl, optionally substituted heterocyclyl, optionally substituted heteroaryl, or optionally substituted heteroaralkyl; and where R$^{32}$, R$^{33}$, R$^{34}$, R$^{35}$ and R$^{36}$ are selected as in (a) or (b) as follows: (a) R$^{32}$, R$^{33}$, R$^{34}$, R$^{35}$ and R$^{36}$ are each independently hydrogen, optionally substituted alkyl, optionally substituted alkenyl, optionally substituted alkynyl, optionally substituted cycloalkyl, optionally substituted aryl, optionally substituted aralkyl, optionally substituted heterocyclyl, optionally substituted heteroaryl, or optionally substituted heteroaralkyl; or (b) R$^{33}$ and R$^{34}$, together with the nitrogen atom to which they are attached, form an optionally substituted heterocyclyl ring, or an optionally substituted heteroaryl ring, and the others of R$^{32}$, R$^{35}$ and R$^{36}$ are selected as in (a) above.

20. The compound of claim 19 wherein R$^1$ is —C(O)OCH$_2$CH$_3$, —C(O)OCH$_3$, —C(O)OCH(CH$_3$)$_2$, —C(O)OH, —C(O)OCH$_2$CH$_2$CH$_3$, —C(O)NHCH$_3$, —C(O)NHCH$_2$CH$_3$, —C(O)NHCH (CH$_3$)$_2$, —C(O)NH(cyclopropyl), —C(O)NH(cyclopentyl), —C(O)NHCH(CH$_3$)(CH$_2$CH$_3$) or —C(O)N(CH$_3$)(cyclopropyl); and
R$^3$ is —C(O)R$^{10}$ wherein R$^{10}$ is optionally substituted aryl, optionally substituted heteroaryl, optionally substituted alkyl or optionally substituted aralkyl.

21. The compound of claim 1 wherein said compound is 6-(3,4-difluoro-benzoyl)-4,4-dimethyl-5,6-dihydro-4H-thieno[2,3-d]azepine-8-carboxylic acid ethyl ester.

22. The compound of claim 12 wherein
X is NR$^9$;
R$^9$ is hydrogen, or optionally substituted alkyl; and
R$^{18}$ and R$^{23}$ each independently optionally substituted alkyl, optionally substituted alkenyl, optionally substituted alkynyl, optionally substituted cycloalkyl, optionally substituted aryl, optionally substituted aralkyl, optionally substituted heterocyclyl, optionally substituted heteroaryl, or optionally substituted heteroaralkyl.

23. The compound of claim 22 wherein:
$R^4$ and $R^5$ are each independently hydrogen or halo; and
$R^6$ and $R^7$ are optionally substituted alkyl.

24. The compound of claim 23 wherein:
$R^9$ is hydrogen.

25. The compound of claim 24 wherein $R^{30}$ is selected from the group consisting of —C(O)$R^{36}$, —C(O)O$R^{32}$, —C(S)O$R^{32}$, —C(O)S$R^{32}$, —C(O)N($R^{33}$)$R^{34}$, —C(S)N($R^{33}$)$R^{34}$, —C(O)N($R^{33}$)S(O)$_2R^{23}$, —C(S)N($R^{33}$)S(O)$_2R^{23}$, —C(O)N($R^{35}$)N($R^{33}$)$R^{34}$, —C(S)N($R^{35}$)N($R^{33}$)$R^{34}$ and —C(O)N($R^{35}$)N($R^{33}$)S(O)$_2R^{23}$;
  where $R^{23}$ is optionally substituted alkyl, optionally substituted alkenyl, optionally substituted alkynyl, optionally substituted cycloalkyl, optionally substituted aryl, optionally substituted aralkyl, optionally substituted heterocyclyl, optionally substituted heteroaryl, or optionally substituted heteroaralkyl; and
  where $R^{32}$, $R^{33}$, $R^{34}$, $R^{35}$ and $R^{36}$ are selected as in (a) or (b) as follows: (a) $R^{32}$, $R^{33}$, $R^{34}$, $R^{35}$ and $R^{36}$ are each independently hydrogen, optionally substituted alkyl, optionally substituted alkenyl, optionally substituted alkynyl, optionally substituted cycloalkyl, optionally substituted aryl, optionally substituted aralkyl, optionally substituted heterocyclyl, optionally substituted heteroaryl, or optionally substituted heteroaralkyl; or (b) $R^{33}$ and $R^{34}$, together with the nitrogen atom to which they are attached, form an optionally substituted heterocyclyl ring, or an optionally substituted heteroaryl ring, and the others of $R^{32}$, $R^{35}$ and $R^{36}$ are selected as in (a) above.

26. The compound of claim 25 wherein $R^1$ is —C(O)OCH$_2$CH$_3$, —C(O)OCH$_3$, —C(O)OCH(CH$_3$)$_2$, —C(O)OH, —C(O)OCH$_2$CH$_2$CH$_3$, —C(O)NHCH$_3$, —C(O)NHCH$_2$CH$_3$, —C(O)NHCH(CH$_3$)$_2$, —C(O)NH(cyclopropyl), —C(O)NH(cyclopentyl), —C(O)NHCH(CH$_3$)(CH$_2$CH$_3$) or —C(O)N(CH$_3$)(cyclopropyl); and
$R^3$ is —C(O)$R^{10}$ wherein $R^{10}$ is optionally substituted aryl, optionally substituted heteroaryl, optionally substituted alkyl or optionally substituted aralkyl.

27. The compound of claim 26 wherein said compound is selected from the group consisting of:
  6-(3,4-difluoro-benzoyl)-4,4-dimethyl-1,4,5,6-tetrahydro-pyrrolo[2,3-d]azepine-2,8-dicarboxylic acid diethyl ester; and
  6-(3,4-difluoro-benzoyl)-4,4-dimethyl-1,4,5,6-tetrahydro-pyrrolo[2,3-d]azepine-2,8-dicarboxylic acid 2-ethyl ester 8-isopropyl ester.

28. The compound of claim 4 wherein:
$R^4$, $R^5$, $R^6$ and $R^7$ are each independently hydrogen or halo; and
$R^{30}$ is selected from the group consisting of hydrogen, halo, —C(O)$R^{36}$, —C(O)O$R^{32}$, —C(S)O$R^{32}$, —C(O)S$R^{32}$, —C(O)N($R^{33}$)$R^{34}$, —C(S)N($R^{33}$)$R^{34}$, —C(O)N($R^{33}$)S(O)$_2R^{23}$, —C(S)N($R^{33}$)S(O)$_2R^{23}$, —C(O)N($R^{35}$)N($R^{33}$)$R^{34}$, —C(S)N($R^{35}$)N($R^{33}$)$R^{34}$ and —C(O)N($R^{35}$)N($R^{33}$)S(O)$_2R^{23}$;
  where $R^{23}$ is optionally substituted alkyl, optionally substituted alkenyl, optionally substituted alkynyl, optionally substituted cycloalkyl, optionally substituted aryl, optionally substituted aralkyl, optionally substituted heterocyclyl, optionally substituted heteroaryl, or optionally substituted heteroaralkyl; and
  where $R^{32}$, $R^{33}$, $R^{34}$, $R^{35}$ and $R^{36}$ are selected as in (a) or (b) as follows: (a) $R^{32}$, $R^{33}$, $R^{34}$, $R^{35}$ and $R^{36}$ are each independently hydrogen, optionally substituted alkyl, optionally substituted alkenyl, optionally substituted alkynyl, optionally substituted cycloalkyl, optionally substituted aryl, optionally substituted aralkyl, optionally substituted heterocyclyl, optionally substituted heteroaryl, or optionally substituted heteroaralkyl; or (b) $R^{33}$ and $R^{34}$, together with the nitrogen atom to which they are attached, form an optionally substituted heterocyclyl ring, or an optionally substituted heteroaryl ring, and the others of $R^{32}$, $R^{35}$ and $R^{36}$ are selected as in (a) above.

29. The compound of claim 1 wherein said compound is 6-(3,4-difluoro-benzoyl)-1,4,4-trimethyl-1,4,5,6-tetrahydro-pyrrolo[2,3-d]azepine-2,8-dicarboxylic acid 2-ethyl ester 8-isopropyl ester.

30. The compound of claim 4 wherein:
Y is C$R^{30}$;
Z is C$R^{31}$; and
$R^{30}$ and $R^{31}$ together with the carbon atoms to which they are attached, form an optionally substituted cycloalkyl ring, or optionally substituted nonaromatic cycloalkenyl ring.

31. The compound of claim 30 wherein said optionally substituted cycloalkyl ring is optionally substituted cyclopentyl, optionally substituted cyclohexyl, optionally substituted cycloheptyl or optionally substituted cyclooctyl.

32. A compound having the formula (V):

(V)

or a pharmaceutically acceptable salt thereof, wherein:
n is 0 to 8;
$R^1$ is selected from a group consisting of —O$R^{14}$, —S$R^{14}$, —N($R^{15}$)$R^{16}$, —N($R^{15}$)S(O)$_2R^{23}$; —N($R^{17}$)N($R^{15}$)$R^{16}$, —N($R^{17}$)N($R^{15}$)S(O)$_2R^{23}$, —C(O)$R^{18}$, —C(O)O$R^{14}$, —C(S)O$R^{14}$, —C(O)S$R^{14}$, —C(O)N($R^{15}$)$R^{16}$, —C(O)N($R^{15}$)S(O)$_2R^{23}$, —C(O)N($R^{15}$)N=$R^{16}$, —C(O)N($R^{17}$)N($R^{15}$)$R^{16}$, and —C(O)N($R^{17}$)N($R^{15}$)S(O)$_2R^{23}$;
$R^2$ is hydrogen;
$R^3$ is hydrogen, —C(O)$R^{10}$, —C(O)O$R^{10}$, —S(O)$_2R^{10}$, —C(O)N($R^{11}$)$R^{12}$, —C(O)N($R^{11}$)S(O)$_2R^{23}$, —C(O)N($R^{13}$)N($R^{11}$)$R^{12}$, —C(O)N($R^{13}$)N($R^{11}$)S(O)$_2R^{23}$, —N($R^{13}$)C(O)$R^{10}$, —N($R^{13}$)C(O)N($R^{11}$)$R^{12}$, —N($R^{13}$)C(O)N($R^{11}$)S(O)$_2R^{23}$, —N($R^{10}$)C(O)N($R^{13}$)N($R^{11}$)$R^{12}$, —N($R^{10}$)C(O)N($R^{13}$)N($R^{11}$)S(O)$_2R^{23}$, —N($R^{13}$)C(O)O$R^{10}$, —P(O)O$R^{10}$, or —P(O)(O$R^{19}$)O$R^{12}$;
$R^4$, $R^5$, $R^6$ and $R^7$ are each independently selected from a group consisting of hydrogen, halo, optionally substituted alkyl, optionally substituted alkenyl, or optionally substituted alkynyl;
$R^9$ is hydrogen, or optionally substituted alkyl;
$R^{10}$, $R^{11}$, $R^{12}$, $R^{13}$ and $R^{19}$ are selected as in (a) or (b) as follows: (a) $R^{10}$, $R^{11}$, $R^{12}$, $R^{13}$ and $R^{19}$ each independently hydrogen, optionally substituted alkyl, optionally substituted alkenyl, optionally substituted alkynyl, optionally substituted cycloalkyl, optionally substituted aryl, optionally substituted aralkyl, optionally substituted heterocyclyl, optionally substituted heteroaryl, or optionally substituted heteroaralkyl; or (b) $R^{11}$ and $R^{12}$ or $R^{12}$ and $R^{19}$, together with the atoms to which they are attached, form an optionally substituted heterocyclyl ring or an optionally substituted heteroaryl ring; and the others of $R^{10}$, $R^{11}$, $R^{12, R13}$, and $R^{19}$ are selected as in (a), above;

$R^{14}$, $R^{15}$, $R^{16}$, $R^{17}$ and $R^{18}$ are selected as in (a) or (b) as follows: (a) $R^{14}$, $R^{15}$, $R^{16}$, $R^{17}$ and $R^{18}$ are each independently hydrogen, optionally substituted alkyl, optionally substituted alkenyl, optionally substituted alkynyl, optionally substituted cycloalkyl, optionally substituted aryl, optionally substituted aralkyl, optionally substituted heterocyclyl, optionally substituted heteroaryl, or optionally substituted heteroaralkyl; or (b) $R^{15}$ and $R^{16}$, together with the nitrogen atom to which they are attached, form an optionally substituted heterocyclyl ring, or an optionally substituted heteroaryl ring, and $R^{14}$, $R^{17}$ and $R^{18}$ are selected as in (a) above;

$R^{23}$ is optionally substituted alkyl, optionally substituted alkenyl, optionally substituted alkynyl, optionally substituted cycloalkyl, optionally substituted aryl, optionally substituted aralkyl, optionally substituted heterocyclyl, optionally substituted heteroaryl, or optionally substituted heteroaralkyl;

each of $R^4$, $R^5$, $R^6$, $R^7$, $R^9$, $R^{10}$, $R^{11}$, $R^{12}$, $R^{13}$, $R^{14}$, $R^{15}$, $R^{16}$, $R^{17}$, $R^{18}$ and $R^{19}$, when substituted, are substituted with one or more substituents, each independently selected from $Q^1$;

each $Q^1$ is independently selected from halo, pseudohalo, oxo, thioxo, cyano, thiocyano, isocyano, nitro, azido, alkyl, haloalkyl, alkenyl containing 1 to 2 double bonds, alkynyl containing 1 to 2 triple bonds, cycloalkyl, cycloalkenyl, cycloalkynyl, cycloalkylalkyl, heterocyclyl, heterocyclylalkyl, aryl, heteroaryl, aralkyl, aralkenyl, aralkynyl, heteroarylalkyl, alkylidene, arylalkylidene, aryloxyarylcarbonylamino, hydroxycarbonylalkylthio, halosulfonyl, —$OR^{70}$, —$SR^{70}$, —$R^{60}$—C(J)$R^{71}$, —$R^{60}$—N($R^{70}$)C(J)$R^{71}$, —OC(O)$R^{71}$, —$R^{60}$—N($R^{75}$)($R^{76}$), —P($R^{78}$)$_2$, —P(O)($R^{78}$)$_2$, —OP(O)($R^{78}$)$_2$, —N($R^{70}$)S(O)$_2$$R^{71}$, —S(O)$_2$$R^{71}$, —S(O)$R^{82}$, —OS(O)$R^{83}$, —OS(O)$_2$$R^{83}$ or —Si($R^{83}$)$_3$;

two $Q^1$ groups, which substitute atoms in a 1,2 or 1,3 arrangement, together with the carbon atoms to which they are attached form a cycloalkyl ring, cycloalkenyl ring, cycloalkynyl ring or heterocyclyl ring; or each $Q^1$ is independently substituted or unsubstituted with one or more substituents each independently selected from $Q^2$;

each $Q^2$ is independently selected from halo, pseudohalo, oxo, thioxo, cyano, thiocyano, isocyano, nitro, azido, alkyl, haloalkyl, alkenyl containing 1 to 2 double bonds, alkynyl containing 1 to 2 triple bonds, cycloalkyl, cycloalkenyl, cycloalkynyl, cycloalkylalkyl, heterocyclyl, heterocyclylalkyl, aryl, heteroaryl, aralkyl, aralkenyl, aralkynyl, heteroarylalkyl, alkylidene, arylalkylidene, aryloxyarylcarbonylamino, hydroxycarbonylalkylthio, halosulfonyl, —$OR^{70}$, —$SR^{70}$, —$R^{60}$—C(J)$R^{71}$, —$R^{60}$—N($R^{70}$)C(J)$R^{71}$, —OC(O)$R^{71}$, —$R^{60}$—N($R^{75}$)($R^{76}$), —P($R^{78}$)$_2$, —P(O)($R^{78}$)$_2$, —OP(O)($R^{78}$)$_2$, —N($R^{70}$)S(O)$_2$$R^{71}$, —S(O)$_2$$R^{71}$, —S(O)$R^{82}$, —OS(O)$R^{83}$, —OS(O)$_2$$R^{83}$ or —Si($R^{83}$)$_3$;

two $Q^2$ groups, which substitute atoms in a 1,2 or 1,3 arrangement, together with the carbon atoms to which they are attached form a cycloalkyl ring, cycloalkenyl ring, cycloalkynyl ring or heterocyclyl ring;

each J is independently O, S or —$NR^{70}$;

each $R^{60}$ is independently a direct bond or alkylene;

each $R^{70}$ is independently hydrogen, alkyl, alkenyl, alkynyl, cycloalkyl, heterocyclyl, aryl, heteroaryl, aralkyl, haloalkyl, heterocyclylalkyl or heteroaralkyl;

each $R^{71}$ is independently hydrogen, alkyl, alkenyl, alkynyl, cycloalkyl, heterocyclyl, aryl, heteroaryl, aralkyl, haloalkyl, heterocyclylalkyl, heteroaralkyl, —$OR^{72}$ or —N($R^{73}$)$R^{74}$;

$R^{72}$, $R^{73}$ and $R^{74}$ are each independently hydrogen, alkyl, alkenyl, alkynyl, cycloalkyl, heterocyclyl, aryl, heteroaryl, aralkyl or heteroaralkyl; or $R^{73}$ and $R^{74}$, together with the nitrogen atom to which they are attached, form a heterocyclyl ring or heteroaryl ring;

$R^{75}$ and $R^{76}$ are each independently hydrogen, alkyl, alkenyl, alkynyl, aryl, aralkyl, heteroaryl, heteroaralkyl, heterocyclyl or heterocyclylalkyl; or $R^{75}$ and $R^{76}$, together with the nitrogen atom to which they are attached, form a heterocyclyl ring or heteroaryl ring;

$R^{78}$ is alkyl, heteroaryl, heterocyclyl, aryl, —$OR^{79}$ or —N($R^{80}$)$R^{81}$;

$R^{79}$ is hydrogen, alkyl, alkenyl, cycloalkyl, heterocyclyl, aryl, heteroaryl, aralkyl or heteroaralkyl;

$R^{80}$ and $R^{81}$ are each independently hydrogen, alkyl, alkenyl, alkynyl, cycloalkyl, heterocyclyl, aryl, heteroaryl, aralkyl or heteroaralkyl; or $R^{80}$ and $R^{81}$, together with the nitrogen atom to which they are attached, form a heterocyclyl ring or heteroaryl ring;

$R^{82}$ is alkyl, alkenyl, cycloalkyl, heterocyclyl, aryl, heteroaryl, aralkyl, heteroaralkyl or —$OR^{83}$; and each $R^{83}$ is independently alkyl, alkenyl, cycloalkyl, heterocyclyl, aryl, heteroaryl, aralkyl or heteroaralkyl.

33. The compound of claim 32 wherein:
$R^3$ is —C(O)$R^{10}$;
wherein $R^{10}$ is optionally substituted aryl, optionally substituted heteroaryl, optionally substituted alkyl or optionally substituted aralkyl.

34. The compound of claim 33 wherein:
$R^1$ is —C(O)$R^{18}$, —C(O)O$R^{14}$ or —C(O)N($R^{15}$)$R^{16}$, where $R^{14}$ and $R^{15}$ are optionally substituted alkyl, optionally substituted cycloalkyl, or optionally substituted heterocyclyl, $R^{16}$ is hydrogen, and $R^{18}$ is optionally substituted alkyl.

35. The compound of claim 34 wherein:
$R^9$ is hydrogen or optionally substituted alkyl.

36. The compound of claim 35 wherein $R^4$, $R^5$, $R^6$ and $R^7$ are selected from a), b), c), and d) below:
a) $R^4$ and $R^5$ are each independently hydrogen or halo and $R^6$ and $R^7$ are optionally substituted alkyl;
b) $R^6$ and $R^7$ are each independently hydrogen or halo and $R^4$ and $R^5$ are optionally substituted alkyl;
c) $R^4$, $R^5$, $R^6$ and $R^7$ are each optionally substituted alkyl; and
d) $R^4$, $R^5$, $R^6$ and $R^7$ are each independently hydrogen or halo.

37. The compound of claim 36 wherein:
$R^4$ and $R^5$ are each independently hydrogen or halo; and
$R^6$ and $R^7$ are optionally substituted alkyl.

38. The compound of claim 32 wherein $R^1$ is —C(O)OCH$_2$CH$_3$, —C(O)OCH$_3$, —C(O)OCH(CH$_3$)$_2$, —C(O)OH, —C(O)OCH$_2$CH$_2$CH$_3$, —C(O)NHCH$_3$, —C(O)NHCH$_2$CH$_3$, —C(O)NHCH(CH$_3$)$_2$, —C(O)NH(cyclopropyl), —C(O)NH(cyclopentyl), —C(O)NHCH(CH$_3$)(CH$_2$CH$_3$) or —C(O)N(CH$_3$)(cyclopropyl);

$R^3$ is —C(O)$R^{10}$ wherein $R^{10}$ is optionally substituted aryl, optionally substituted heteroaryl, optionally substituted alkyl or optionally substituted aralkyl;

$R^4$ and $R^5$ are each independently hydrogen or halo; and
$R^6$ and $R^7$ are optionally substituted alkyl;
$R^9$ is hydrogen.

39. The compound of claim 38 wherein said compound is 3-(4-fluoro-benzoyl)-1,1-dimethyl-1,2,3,6,7,8,9,10-octahydro-azepino[4,5-b]indole-5-carboxylic acid ethyl ester.

40. The compound of claim 36 wherein $R^4$, $R^5$, $R^6$ and $R^7$ are each independently hydrogen or halo.

41. The compound of claim 40 wherein said compound is 3-(4-fluoro-benzoyl)-1,2,3,6,7,8,9,10-octahydro-azepino[4,5-b]indole-5-carboxylic acid ethyl ester.

42. A pharmaceutical composition comprising a pharmaceutical carrier or vehicle and a compound having the formula (I):

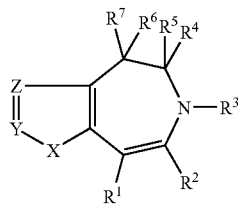

wherein:
X is $NR^9$, or S;
Y is $CR^{30}$;
Z is $CR^{31}$ or N;
$R^{30}$ and $R^{31}$ are each independently selected from the group consisting of halo, hydrogen, optionally substituted alkyl, optionally substituted alkenyl, optionally substituted alkynyl, optionally substituted aryl, optionally substituted heteroaryl, optionally substituted cycloalkyl, optionally substituted cycloalkylalkyl, optionally substituted heterocyclyl, optionally substituted heterocyclylalkyl, optionally substituted aralkyl, optionally substituted heteroaralkyl, —$OR^{32}$, —$SR^{32}$, —$N(R^{33})R^{34}$, —$N(R^{33})S(O)_2R^{23}$; —$N(R^{35})N(R^{33})R^{34}$, —$N(R^{35})N(R^{33})S(O)_2R^{23}$, —$C(O)R^{36}$, —$C(O)OR^{32}$, —$C(S)OR^{32}$, —$C(O)SR^{32}$, —$C(O)N(R^{33})R^{34}$, —$C(S)N(R^{33})R^{34}$, —$C(O)N(R^{33})S(O)_2R^{23}$, —$C(S)N(R^{33})S(O)_2R^{23}$, —$C(O)N(R^{35})N(R^{33})R^{34}$, —$C(S)N(R^{35})N(R^{33})R^{34}$ and —$(O)N(R^{35})N(R^{33})S(O)_2R^{23}$; or
$R^{30}$ and $R^{31}$ together with the carbon atoms to which they are attached, form an optionally substituted cycloalkyl ring, or optionally substituted nonaromatic cycloalkenyl ring;
$R^{32}$, $R^{33}$, $R^{34}$, $R^{35}$ and $R^{36}$ are selected as in (a) or (b) as follows: (a) $R^{32}$, $R^{33}$, $R^{34}$, $R^{35}$ and $R^{36}$ are each independently hydrogen, optionally substituted alkyl, optionally substituted alkenyl, optionally substituted alkynyl, optionally substituted cycloalkyl, optionally substituted aryl, optionally substituted aralkyl, optionally substituted heterocyclyl, optionally substituted heteroaryl, or optionally substituted heteroaralkyl; or (b) $R^{33}$ and $R^{34}$, together with the nitrogen atom to which they are attached, form an optionally substituted heterocyclyl ring, or an optionally substituted heteroaryl ring, and $R^{32}$, $R^{35}$ and $R^{36}$ are selected as in (a) above,
$R^1$ is selected from a group consisting of —$OR^{14}$, —$SR^{14}$, —$N(R^{15})R^{16}$, —$N(R^{15})S(O)_2R^{23}$; —$N(R^{17})N(R^{15})R^{16}$, —$N(R^{17})N(R^{15})S(O)_2R^{23}$, —$C(O)R^{18}$, —$C(O)OR^{14}$, —$C(S)OR^{14}$, —$C(O)SR^{14}$, —$C(O)N(R^{15})R^{16}$, —$C(O)N(R^{15})S(O)_2R^{23}$, —$C(O)N(R^{15})N=R^{16}$, —$C(O)N(R^{17})N(R^{15})R^{16}$ and —$C(O)N(R^{17})N(R^{15})S(O)_2R^{23}$;
$R^2$ is hydrogen;
$R^3$ is hydrogen, —$C(O)R^{10}$, —$C(O)OR^{10}$, —$S(O)_2R^{10}$, —$C(O)N(R^{11})R^{12}$, —$C(O)N(R^{11})S(O)_2R^{23}$, —$C(O)N(R^{13})N(R^{11})R^{12}$, —$C(O)N(R^{13})N(R^{11})S(O)_2R^{23}$, —$N(R^{13})C(O)R^{10}$, —$N(R^{13})C(O)N(R^{11})R^{12}$, —$N(R^{13})C(O)N(R^{11})S(O)_2R^{23}$, —$N(R^{10})C(O)N(R^{13})N(R^{11})R^{12}$, —$N(R^{10})C(O)N(R^{13})N(R^{11})S(O)_2R^{23}$, —$N(R)^{13}C(O)OR^{10}$, —$P(O)OR^{10}$, or —$P(O)(OR^{19})OR^{12}$;
$R^4$, $R^5$, $R^6$ and $R^7$ are each independently selected from a group consisting of hydrogen, halo, optionally substituted alkyl, optionally substituted alkenyl, or optionally substituted alkynyl;
$R^9$ is hydrogen, or optionally substituted alkyl;
$R^{10}$, $R^{11}$, $R^{12}$, $R^{13}$ and $R^{19}$ are selected as in (a) or (b) as follows: (a) $R^{10}$, $R^{11}$, $R^{12}$, $R^{13}$ and $R^{19}$ each independently hydrogen, optionally substituted alkyl, optionally substituted alkenyl, optionally substituted alkynyl, optionally substituted cycloalkyl, optionally substituted aryl, optionally substituted aralkyl, optionally substituted heterocyclyl, optionally substituted heteroaryl, or optionally substituted heteroalkyl; or (b) $R^{10}$ and $R^{12}$ or $R^{12}$ and $R^{19}$, together with the atoms to which they are attached, form an optionally substituted heterocyclyl ring or an optionally substituted heteroaryl ring; and the others of $R^{10}$, $R^{11}$, $R^{12}$, $R^{13}$ and $K^{19}$ are selected as in (a), above;
$R^{14}$, $R^{15}$, $R^{16}$, $R^{17}$ and $R^{18}$ are selected as in (a) or (b) as follows: (a) $R^{14}$, $R^{15}$, $R^{16}$, $R^{17}$ and $R^{18}$ are each independently hydrogen, optionally substituted alkyl, optionally substituted alkenyl, optionally substituted alkynyl, optionally substituted cycloalkyl, optionally substituted aryl, optionally substituted aralkyl, optionally substituted heterocyclyl, optionally substituted heteroaryl, or optionally substituted heteroaralkyl; or (b) $R^{15}$ and $R^{16}$, together with the nitrogen atom to which they are attached, form an optionally substituted heterocyclyl ring, or an optionally substituted heteroaryl ring, and $R^{14}$, $R^{17}$ and $R^{18}$ are selected as in (a) above;
$R^{23}$ is optionally substituted alkyl, optionally substituted alkenyl, optionally substituted alkynyl, optionally substituted cycloalkyl, optionally substituted aryl, optionally substituted aralkyl, optionally substituted heterocyclyl, optionally substituted heteroaryl, or optionally substituted heteroaralkyl;
each of $R^4$, $R^5$, $R^6$, $R^7$, $R^9$, $R^{10}$, $R^{11}$, $R^{12}$, $R^{13}$, $R^{14}$, $R^{15}$, $R^{16}$, $R^{17}$, $R^{18}$, $R^{19}$, and $R^{30}$, $R^{31}$, $R^{32}$, $R^{33}$, $R^{34}$, $R^{35}$ and $R^{36}$, when substituted, are substituted with one or more substituents, each independently selected from $Q^1$;
each $Q^1$ is independently selected from halo, pseudohalo, oxo, thioxo, cyano, thiocyano, isocyano, nitro, azido, alkyl, haloalkyl, alkenyl containing 1 to 2 double bonds, alkynyl containing 1 to 2 triple bonds, cycloalkyl, cycloalkenyl, cycloalkynyl, cycloalkylalkyl, heterocyclyl, heterocyclylalkyl, aryl, heteroaryl, aralkyl, aralkenyl, aralkynyl, heteroarylalkyl, alkylidene, arylalkylidene, aryloxyarylcarbonylamino, hydroxycarbonylalkylthio, halosulfonyl, —$OR^{70}$, —$SR^{70}$, —$R^{60}$—$C(J)R^{71}$, —$R^{60}$—$N(R^{70})C(J)R^{71}$, —$OC(O)R^{71}$, —$R^{60}$—$N(R^{75})(R^{76})$, —$P(R^{78})_2$, —$P(O)(R^{78})_2$, —$OP(O)(R^{78})_2$, —$N(R^{70})S(O)_2R^{71}$, —$S(O)_2R^{71}$, —$S(O)R^{82}$, —$OS(O)R^{83}$, —$OS(O)_2R^{83}$ or —$Si(R^{83})_3$;

two $Q^1$ groups, which substitute atoms in a 1,2 or 1,3 arrangement, together with the carbon atoms to which they are attached form a cycloalkyl ring, cycloalkenyl ring, cycloalkynyl ring or heterocyclyl ring; or each $Q^1$ is independently substituted or unsubstituted with one or more substituents each independently selected from $Q^2$;

each $Q^2$ is independently selected from halo, pseudohalo, oxo, thioxo, cyano, thiocyano, isocyano, nitro, azido, alkyl, haloalkyl, alkenyl containing 1 to 2 double bonds, alkynyl containing 1 to 2 triple bonds, cycloalkyl, cycloalkenyl, cycloalkynyl, cycloalkylalkyl, heterocyclyl, heterocyclylalkyl, aryl, heteroaryl, aralkyl, aralkenyl, aralkynyl, heteroarylalkyl, alkylidene, arylalkylidene, aryloxyarylcarbonylamino, hydroxycarbonylalkylthio, halosulfonyl, —$OR^{70}$, —$SR^{70}$, —$R^{60}$—$C(J)R^{71}$, —$R^{60}$—$N(R^{70})C(J)R^{71}$, —$OC(O)R^{71}$, —$R^{60}$—$N(R^{75})(R^{76})$, —$P(R^{78})_2$, —$P(O)(R^{78})_2$, —$OP(O)(R^{78})_2$, —$N(R^{70})S(O)_2R^{71}$, —$S(O)_2R^{71}$, —$S(O)R^{82}$, —$OS(O)R^{83}$, —$OS(O)_2R^{83}$ or —$Si(R^{83})_3$;

two $Q^2$ groups, which substitute atoms in a 1,2 or 1,3 arrangement, together with the carbon atoms to which they are attached form a cycloalkyl ring, cycloalkenyl ring, cycloalkynyl ring or heterocyclyl ring;

each J is independently O, S or —$NR^{70}$;

each $R^{60}$ is independently a direct bond or alkylene;

each $R^{70}$ is independently hydrogen, alkyl, alkenyl, alkynyl, cycloalkyl, heterocyclyl, aryl, heteroaryl, aralkyl, haloalkyl, heterocyclylalkyl or heteroaralkyl;

each $R^{71}$ is independently hydrogen, alkyl, alkenyl, alkynyl, cycloalkyl, heterocyclyl, aryl, heteroaryl, aralkyl, haloalkyl, heterocyclylalkyl, heteroaralkyl, —$OR^{72}$ or —$N(R^{73})R^{74}$;

$R^{72}$, $R^{73}$ and $R^{74}$ are each independently hydrogen, alkyl, alkenyl, alkynyl, cycloalkyl, heterocyclyl, aryl, heteroaryl, aralkyl or heteroaralkyl; or $R^{73}$ and $R^{74}$, together with the nitrogen atom to which they are attached, form a heterocyclyl ring or heteroaryl ring;

$R^{75}$ and $R^{76}$ are each independently hydrogen, alkyl, alkenyl, alkynyl, aryl, aralkyl, heteroaryl, heteroaralkyl, heterocyclyl or heterocyclylalkyl; or $R^{75}$ and $R^{76}$, together with the nitrogen atom to which they are attached, form a heterocyclyl ring or heteroaryl ring;)

$R^{78}$ is alkyl, heteroaryl, heterocyclyl, aryl, —$OR^{79}$ or —$N(R^{80})R^{81}$;

$R^{79}$ is hydrogen, alkyl, alkenyl, cycloalkyl, heterocyclyl, aryl, heteroaryl, aralkyl or heteroaralkyl;

$R^{80}$ and $R^{81}$ are each independently hydrogen, alkyl, alkenyl, alkynyl, cycloalkyl, heterocyclyl, aryl, heteroaryl, aralkyl or heteroaralkyl; or $R^{80}$ and $R^{81}$, together with the nitrogen atom to which they are attached, form a heterocyclyl ring or heteroaryl ring;

$R^{82}$ is alkyl, alkenyl, cycloalkyl, heterocyclyl, aryl, heteroaryl, aralkyl, heteroaralkyl or —$OR^{83}$; and each $R^{83}$ is independently alkyl, alkenyl, cycloalkyl, heterocyclyl, aryl, heteroaryl, aralkyl or heteroaralkyl;

as a single isomer, a mixture of isomers, or as a racemic mixture of isomers; or as a pharmaceutically acceptable salt thereof.

43. A method of treating or ameliorating one or more symptoms of a disease or disorder wherein the disease or disorder is selected from hyperlipidemia, hypercholesterolemia, hypertriglyceridemia, dyslipidemia, lipodystrophy, atherosclerosis, atherosclerotic disease, atherosclerotic disease events, atherosclerotic cardiovascular disease, Syndrome X, diabetes mellitus, type II diabetes, insulin insensitivity, hyperglycemia, cholestasis and obesity comprising administering to a subject in need thereof an effective amount of a compound or composition of any one claims 1-3, 4, 5-34 35-37, and 38-42.

* * * * *